United States Patent [19]
Belley et al.

[11] Patent Number: 5,565,473
[45] Date of Patent: Oct. 15, 1996

[54] UNSATURATED HYDROXYALKYLQUINOLINE ACIDS AS LEUKOTRIENE ANTAGONISTS

[75] Inventors: Michel L. Belley, Pierrefonds; Serge Leger, Dollard des Ormeaux; Marc Labelle, Ville d'Ile Perrot; Patrick Roy; Yi B. Xiang, both of Pierrefonds; Daniel Guay, Montreal, all of Canada

[73] Assignee: Merck Frosst Canada, Inc., Kirkland, Canada

[21] Appl. No.: 392,592

[22] Filed: Feb. 23, 1995

Related U.S. Application Data

[63] Continuation of Ser. No. 774,414, Oct. 10, 1991, abandoned, which is a continuation-in-part of Ser. No. 741,888, Aug. 8, 1991, abandoned, which is a continuation-in-part of Ser. No. 596,887, Oct. 12, 1990, abandoned.

[51] Int. Cl.$^6$ .................. A01N 43/42; C07D 215/36; C07D 215/12
[52] U.S. Cl. .................. 514/313; 514/314; 514/826; 514/924; 546/162; 546/167; 546/171; 546/172; 546/174; 546/175; 546/176
[58] Field of Search .................. 514/313, 314, 514/826, 924; 541/162, 167, 171, 172, 174, 175, 176

[56] References Cited

FOREIGN PATENT DOCUMENTS 8912629  12/1989  WIPO .................. 546/172

*Primary Examiner*—C. Warren Ivy
*Assistant Examiner*—Raymond Covington
*Attorney, Agent, or Firm*—Mollie M. Yang; David L. Rose

[57] ABSTRACT

Compounds having the formula I:

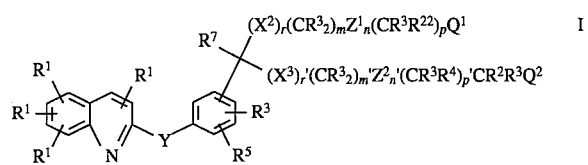

are leukotriene antagonists and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

23 Claims, No Drawings

UNSATURATED HYDROXYALKYLQUINOLINE ACIDS AS LEUKOTRIENE ANTAGONISTS

CROSS-REFERENCE

This is a continuation of application Ser. No. 07/774,414, now abandoned, filed Oct. 10, 1991, which is a CIP of U.S. Ser. No. 741,888, Aug. 8, 1991, abandoned, which is a CIP of U.S. Ser. No. 596,887, Oct. 12, 1990, now abandoned.

BACKGROUND OF THE INVENTION

The leukotrienes constitute a group of locally acting hormones, produced in living systems from arachidonic acid. The major leukotrienes are Leukotriene $B_4$ ($LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in *Leukotrienes and Lipoxygenases*, ed. J. Rokach, Elsevier, Amsterdam (1989). The actions of the leukotrienes in living systems and their contribution to various diseases states are also discussed in the book by Rokach.

The art describes certain quinoline-containing compounds as having activity as antagonists of the actions of the leukotrienes. Thus, EP 318,093 (Merck) describes compounds of structure A. Structure B is disclosed in WO 89/12629 (Rorer).

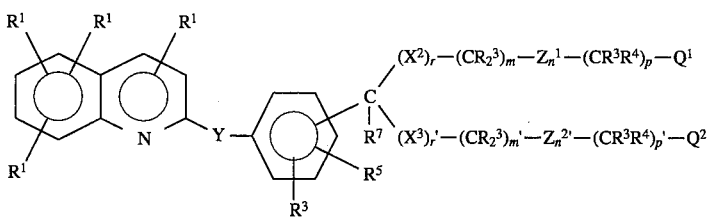

EP 318,093 (Merck)

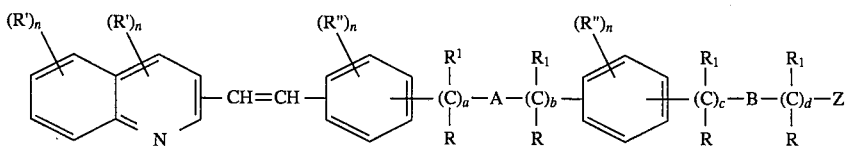

WO 89/12629 (Rorer)

SUMMARY OF THE INVENTION

The present invention relates to unsaturated hydroxyalkylquinoline acids having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compounds of this invention are best realized by Formula I:

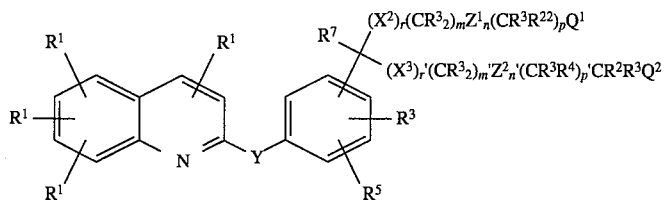

wherein:

$R^1$ is H, halogen, —$CF_3$, —CN, —$NO_2$, or $N_3$;

$R^2$ is lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon may form a ring of up to 8 members containing 0–2 heteroatoms chosen from O, S, and N;

$R^3$ is H or $R^2$;

$CR^3R^{22}$ may be the radical of a standard amino acid;

$R^4$ is halogen, —$NO_2$, —CN, —$OR^3$, —$SR^3$, $NR^3R^3$, $NR^3C(O)R^7$ or $R^3$;

$R^5$ is H, halogen, —$NO_2$, —$N_3$, —CN, —$SR^2$, —$NR^3R^3$, —$OR^3$, lower alkyl, or —$C(O)R^3$;

$R^6$ is $(CH_2)_s$—$C(R^7R^7)$—$(CH_2)_s$—$R^8$ or —$CH_2C(O)NR^{12}R^{12}$;

$R^7$ is H or $C_1$–$C_4$ alkyl;

$R^8$ is
A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W—$R^9$;

$R^9$ contains up to 20 carbon atoms and is (1) an alkyl group or (2) an alkylcarbonyl group of an organic acyclic or monocyclic carboxylic acid containing not more than 1 heteroatom in the ring;

$R^{10}$ is —$SR^{11}$, —$OR^{12}$, or —$NR^{12}R^{12}$;

$R^{11}$ is lower alkyl, —$C(O)R^{14}$, unsubstituted phenyl, or unsubstituted benzyl;

$R^{12}$ is H, $R^{11}$ or two $R^{12}$ groups joined to the same N may form a ring of 5 or 6 members containing 1–2 heteroatoms chosen from O, S, and N;

$R^{13}$ is lower alkyl, lower alkenyl, lower alkynyl, —$CF_3$ or substituted or unsubstituted phenyl, benzyl, or 2-phenethyl;

$R^{14}$ is H or $R^{13}$;

$R^{16}$ is H, $C_1$–$C_4$ alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —$CF_3$ or substituted or unsubstituted phenyl, benzyl, or 2-phenethyl;

$R^{19}$ is lower alkyl, lower alkenyl, lower alkynyl, —$CF_3$ or substituted or unsubstituted phenyl, benzyl, or 2-phenethyl;

$R^{20}$ is H, $C_1$–$C_4$ alkyl, substituted or unsubstituted phenyl, benzyl, phenethyl, or pyridinyl or two $R^{20}$ groups joined to the same N may form a saturated ring of 5 or 6 members containing 1–2 heteroatoms chosen from O, S, and N;

$R^{21}$ is H or $R^{17}$;

$R^{22}$ is $R^4$, $CHR^7OR^3$, or $CHR^7SR^2$;

m and m' are independently 0–8;

n and m' are independently 0 or 1, p and p' are independently 0–8;

m+n+p is 1–10 when r is 1 and $X^2$ is O, S, S(O), or $S(O)_2$;

m+n+p is 0–10 when r is 1 and $X^2$ is $CR^3R^{16}$;

m+n+p is 0–10 when r is O;

m'+m'+p' is 0–10;

r and r' are independently 0 or 1;

s is 0–3;

$Q^1$ is —$C(O)OR^3$, 1H (or 2H)-tetrazol-5-yl, —$C(O)OR^6$, —$C(O)NHS(O)_2R^{13}$, —CN, —$C(O)NR^{12}R^{12}$, —$NR^{21}S(O)_2R^{13}$, —CN, —$NR^{12}C(O)NR^{12}R^{12}$, —$NR^{21}C(O)R^{18}$, —$OC(O)NR^{12}R^{12}$, —$C(O)R^{19}$, —$S(O)R^{18}$, —$S(O)_2R^{18}$, —$S(O)_2NR^{12}R^{12}$, —$NO_2$, —$NR^{21}C(O)OR^{17}$, —$C(NR^{12}R^{12})$=$NR^{12}$, —$C(R^{13})$=NOH; or if $Q^1$ is —C(O)OH and $R^{22}$ is —OH, —SH, —$CHR^7OH$ or —$NHR^3$, then $Q^1$ and $R^{22}$ and the carbons through which they are attached may form a heterocyclic ring by loss of water;

$Q^2$ is OH or $NR^{20}R^{20}$;

W is O, S, or $NR^3$;

$X^2$ and $X^3$ are independently O, S, S(O), $S(O)_2$, or $CR^3R^{16}$;

Y is —$CR^3$=$CR^3$— or —C≡C—;

$Z^1$ and $Z^2$ are independently —HET(—$R^3$—$R^5$)—;

HET is the diradical of a benzene, a pyridine, a furan, or a thiophene;

and the pharmaceutically acceptable salts thereof.

Definitions

The following abbreviations have the indicated meanings:

Et=ethyl

Me=methyl

Bz=benzyl

Ph=phenyl t-Bu=tert-butyl i-Pr=isopropyl n-Pr=normal propyl c-Hex=cyclohexyl c-Pr=cyclopropyl 1,1-c-Bu=1,1-bis-cyclobutyl 1,1-c-Pr=1,1-bis-cyclopropyl (e.g., $HOCH_2$ (1,1-c-Pr)$CH_2CO_2Me$ is methyl 1-(hydroxymethyl)cyclopropaneacetate)

c-=cyclo

Ac=acetyl

Tz=1H (or 2H)-tetrazol-5-yl

Th=2- or 3-thienyl $C_3H_5$=allyl c-Pen=cyclopentyl c-Bu=cyclobutyl phe=benzenediyl pye=pyridinediyl fur=furandiyl thio=thiophenediyl DEAD=diethyl azocarboxylate DHP=dihydropyran DIAD=diisopropyl azodicarboxylate r.t.=room temperature Alkyl, alkenyl, and alkynyl are intended to include linear, branched, and cyclic structures and combinations thereof.

"Alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl- 4 -propylnonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

"Lower alkenyl" groups means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

"Lower alkynyl" means alkynyl groups of 2 to carbon atoms. Examples of lower alkynyl groups include ethynyl, propargyl, 3-methyl-1-pentynyl, 2-heptynyl, and the like.

"Alkylcarbonyl" means alkylcarbonyl groups of 1 to 20 carbon atom of a straight, branched or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex-$(CH_2)_{10}$—C(O)—.

Substituted phenyl, benzyl, 2-phenethyl and pyridinyl means structures with 1 or 2 substituents on the aromatic ring selected from lower alkyl, $R^{10}$, $NO_2$, $SCF_3$, halogen, —C(O)$R^7$, —C(O)$R^{10}$, CN, $CF_3$, and $CN_4H$.

Halogen means F, Cl, Br and I.

The prodrug esters of $Q^1$ (i.e., when $Q^1$=—C(O)O$R^6$) are intended to mean the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987). Within the definition of $R^8$, some representative monocyclic or bicyclic heterocyclic radicals are:

2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

When $Q^1$ and $R^{22}$ and the carbons through which they are attached form a ring, the rings thus formed include lactones, lactams, and thiolactones.

It is intended that the definitions of any substituent (e.g., $R^1$, $R^2$, m, X, etc.) in a particular molecule be independent of its definitions elsewhere in the molecule. Thus, —N$R^3R^3$ represents —NHH, —NHCH$_3$, —NHC$_6$H$_5$, etc.

The heterocycles formed when two $R^3$, $R^{12}$, or $R^{20}$ groups join through N include pyrrolidine, piperidine, morpholine, thiamorpholine, piperazine, and N-methylpiperazine.

"Standard amino acids", the radical of which may be $CR^3R^{22}$, means the following amino acids: alanins, asparagine, aspattic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, Symposium of the Society of Experimental Biology, 12, 140 (1958)).

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:

$R^1$ is H, halogen, $CF_3$ or —CN;

$R^2$ is $C_1$–$C_4$ alkyl, —$CF_3$, —$CHF_2$, —$CH_2F$, or two $R^2$ groups joined to the same carbon may form a ring of up to 6 carbons;

$R^3$ is H or $R^2$;

$CR^3R^{22}$ may be the radical of a standard amino acid;

$R^4$ is —O$R^3$, —S$R^3$, N$R^3R^3$, NHC(O)CH$_3$, or $R^3$;

$R^5$ is H or halogen;

$R^6$ is $(CH_2)_s$—C($R^7R^7$)—$(CH_2)_s$—$R^8$ or —CH$_2$C(O)N$R^{12}R^{12}$;

$R^7$ is H or $C_1$–$C_4$ alkyl;

$R^8$ is
A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W—$R^9$;

$R^9$ contains up to 20 carbon atoms and is (1) an alkyl group or (2) an alkylcarbonyl group;

$R^{10}$ is —S$R^{11}$, —O$R^{12}$, or —N$R^{12}R^{12}$;

$R^{11}$ is lower alkyl, —C(O)$R^{14}$, unsubstituted phenyl, or unsubstituted benzyl;

$R^{12}$ is M, $R^{11}$, or two $R^{12}$ groups joined to the same N may form a ring of 5 or 6 members containing 1–2 heteroatoms chosen from O, S, and N;

$R^{13}$ is lower alkyl, —$CF_3$, or substituted or unsubstituted phenyl, benzyl, or 2-phenethyl;

$R^{14}$ H or $R^{13}$;

$R^{16}$ is H, $C_1$–$C_4$ alkyl, or OH;

$R^{22}$ is $R^4$, —CH$_2$O$R^3$, or —CH$_2$S$R^2$;

m and m' are independently 0–4;

n and m' are independently 0 or 1;

p and p' are independently 0–4;

m+n+p is 1–9 when r is 1 and $X^2$ is O or S;

m+n+p is 0–9 when r is 1 and $X^2$ is $CR^3R^{16}$;

m+n+p is 0–9 when r is 0;

m'+m'+p' is 1–9;

r and r' are independently 0 or 1;

s is 0–3;

$Q^1$ is —C(O)O$R^3$, 1H (or 2H)-tetrazol-5-yl, —C(O)O$R^6$, —C(O)NHS(O)$_2R^{13}$, —C(O)N$R^{12}R^{12}$, —NHS(O)$_2R^{13}$; or if $Q^1$ is C(O)OH and $R^{22}$ is —OH, —SH, —CH$_{20}$H or —NH$R^3$ then $Q^1$ and $R^{22}$ and the carbons through which they are attached may form a heterocyclic ring by loss of water;

$Q^2$ is OH;

W is O, S, or NH;

$X^2$ and $X^3$ are independently O, S, or $CR^3R^{16}$;

Y is (E)—CH=CH—;

$Z^1$ and $Z^2$ are independently —HET(—$R^3$—$R^5$)—;

HET is the diradical of a benzene, pyridine, furan, or thiophene;

and the pharmaceutically acceptable salts thereof.

Another group of preferred compounds are those wherein the $R^{22}$ α to $Q^1$ is lower alkyl, $CF_3$, or substituted or unsubstituted phenyl.

More preferred compounds of Formula I are represented by Formula Ia:

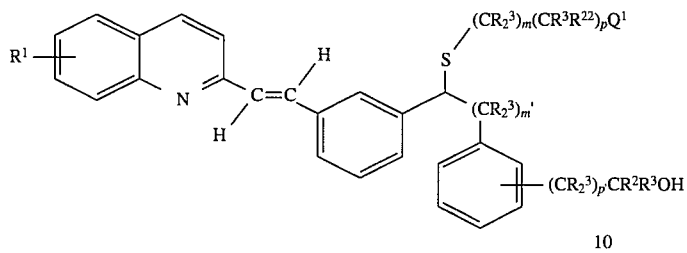

wherein:

$R^1$ is H, halogen, $CF_3$, or CN;

$R^{22}$ is $R^3$, $-CH_2O^3$, or $-CH_2SR^2$;

$Q^1$ is $-C(O)OH$, 1H(or 2H)-tetrazol-5-yl, $-C(O)NHS(O)_2R^{13}$, $-C(O)NR^{12}R^{12}$, or $-NHS(O)_2R^{13}$;

m' is 2 or 3;

p' is 0 or 1;

m+p is 1–5;

the remaining definitions are as in Formula I;

and the pharmaceutically acceptable salts thereof.

Another group of more preferred compounds are as in Formula Ia, wherein:

m' is 0;

and the remaining definitions are as in Formula Ia.

The most preferred compounds of Formula Ia also have a lower alkyl on the carbon α to the group $Q^1$.

Another group of more preferred compounds of Formula I are represented by Formula Ib:

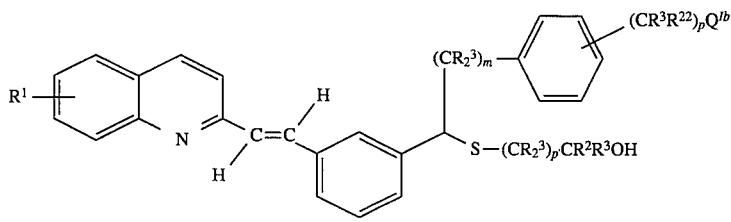

wherein:

$R^1$ is H, halogen, $CF_3$, or CN;

$R^{22}$ is $R^3$, $-CH_2O^3$, or $-CH_2SR^2$;

$Q^1$ is $-C(O)OH$, 1H(or 2H)-tetrazol-5-yl, $-C(O)NHS(O)_2R^{13}$, $-C(O)NR^{12}R^{12}$, or $-NHS(O)_2R^{13}$;

m is 0, 2, or 3;

p is 0 or 1;

p' is 1–4;

m+p is 0–4;

the remaining definitions are as in Formula I;

and the pharmaceutically acceptable salts thereof.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) the propionic acid derivatives;

(2) the acetic acid derivatives;

(3) the fenamic acid derivatives;

(4) the oxicams; and (5) the biphenylcarboxylic acid derivatives;

or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂C⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

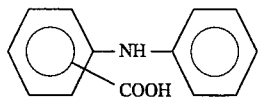

which can bear a variety of substituents and in which the free —COOH group can be in the form of a pharmaceutically acceptable salt group, e.g., —COO⁻Na⁺. The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

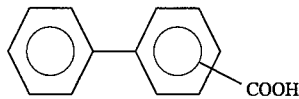

which can bear a variety of substituents and in which the free -C₀₀H group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

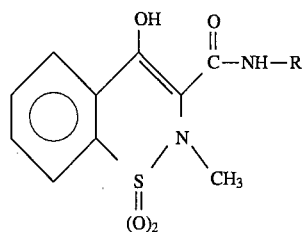

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolioam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., *Pharmaprojects*), may also be used:
480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058, 785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethylhistidine, described in U.S. Pat. No. 4,325,961. The compounds of the Formula I may also be advantageously combined with an $H_1$ or H2-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Representative Compounds

Table I illustrates compounds representative of the present invention. Table II provides elemental analyses for compounds of Table I.

TABLE I

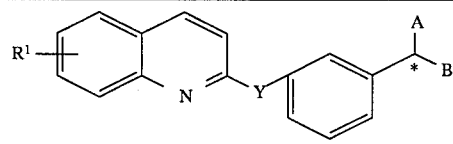

I'

| EX. | * | $R^1$ | Y | A | B |
|---|---|---|---|---|---|
| 1 | RS | 7-Cl | C≡C | $SCH_2CHMeCO_2H$ | $(CH_2)_2(1,2\text{-phe})CMe_2OH$ |
| 2 | RS | 7-Cl | CH=CH | $S(CH_2)_2CO_2H$ | $(CH_2)_2(1,2\text{-phe})C((CH_2)_4)OH$ |
| 3 | RS | 7-Cl | CH=CH | $S(CH_2)_2CO_2H$ | $(CH_2)_2(4\text{-Cl-}1,2\text{-phe})CMe_2OH$ |
| 4 | RS | 7-Cl | CH=CH | $SCH_2CHMeCO_2H$ | $(1,3\text{-phe})CMe_2OH$ |
| 5 | RS | 7-Cl | CH=CH | $S(CH_2)_2CO_2H$ | $(CH_2)_2(1,2\text{-phe})CMe_2OH$ |
| 6 | RS | 7-Cl | CH=CH | $SCH_2CHMeCO_2H$ | $S(CH_2)_2(1\text{-c-Pen})OH$ |
| 7 | RS | 7-Cl | CH=CH | $SCH_2(R)CHMeCO_2H$ | $S(CH_2)_2(1,2\text{-phe})CMe_2OH$ |
| 8 | S | 7-Cl | C≡C | $SCH_2(S)CHMeCO_2H$ | $(CH_2)_2(1,2\text{-phe})CMe_2OH$ |
| 9 | RS | 7-Cl | CH=CH | $SCH_2CHMeCO_2H$ | $(1,4\text{-phe})CMe_2OH$ |
| 10 | RS | 7-Cl | C≡C | $SCH_2CHEtCO_2H$ | $(CH_2)_2(1,2\text{-phe})CMe_2OH$ |
| 11 | RS | 7-Cl | CH=CH | $SCH_2CHEtCO_2H$ | $(1,3\text{-phe})CMe_2OH$ |
| 12 | S | 7-Cl | CH=CH | $SCH_2(S)CHEtCO_2H$ | $(CH_2)_3(1,2\text{-phe})CMe_2OH$ |
| 13 | RS | 7-Cl | CH=CH | $S(CH_2)_2CHMeCO_2H$ | $(CH_2)_2(1,2\text{-phe})CMe_2OH$ |
| 14 | RS | 7-Cl | C≡C | $S(CH_2)_2CO_2H$ | $(CH_2)_2(1,2\text{-phe})CMe_2OH$ |
| 15 | RS | 7-Cl | CH=CH | $SCH_2CHMeCO_2H$ | $(CH_2)_2(1,2\text{-phe})CMe_2OH$ |
| 16 | S | 7-Cl | CH=CH | $SCH_2(S)CHMeCO_2H$ | $(CH_2)_2(1,2\text{-phe})CMe_2OH$ |
| 17 | R | 7-Cl | CH=CH | $SCH_2(S)CHMeCO_2H$ | $(CH_2)_2(1,2\text{-phe})CMe_2OH$ |
| 18 | S | 7-Cl | CH=CH | $S(CH_2)_2CO_2H$ | $S(CH_2)_2CMe_2OH$ |
| 19 | S | 7-Cl | CH=CH | $SCH_2CHMeCO_2H$ | $(CH_2)_2(1,2\text{-phe})C(CF_3)_2OH$ |
| 20 | RS | 7-Cl | CH=CH | $SCH_2CHMeCO_2H$ | $(CH_2)_2(1,3\text{-phe})C(CF_3)_2OH$ |
| 21 | RS | 7-Cl | CH=CH | $SCH_2CHMeCO_2H$ | $(CH_2)_2(1,3\text{-phe})CMe_2OH$ |
| 22 | RS | 7-Cl | CH=CH | $SCH_2CHEtCO_2H$ | $SCH_2CMe_2CMe_2OH$ |
| 23 | RS | 7-Cl | CH=CH | $SCH_2CHMeCMe_2OH$ | $(CH_2)_2(1,2\text{-phe})CO_2H$ |
| 24 | RS | 7-Cl | CH=CH | $SCH_2CHMeCMe_2OH$ | $(CH_2)_2(1,2\text{-phe})CONH_2$ |
| 25 | RS | 7-Cl | CH=CH | $SCH_2CHMeCO_2H$ | $SCH_2(1,2\text{-phe})CMe_2OH$ |
| 26 | RS | 7-Cl | CH=CH | $SCH_2CHMeCO_2H$ | $(CH_2)_2(1,4\text{-phe})CMe_2OH$ |
| 27 | RS | 7-Cl | CH=CH | $SCH_2CHEtCO_2H$ | $(CH_2)_2(1,2\text{-phe})CMe_2OH$ |
| 28 | RS | 7-Cl | CH=CH | $SCH_2CH(OMe)CO_2H$ | $(CH_2)_2(1,2\text{-phe})CMe_2OH$ |
| 29 | S | 7-Cl | CH=CH | $SCH_2(R)CHEtCO_2H$ | $(CH_2)_2(1,2\text{-phe})CMe_2OH$ |
| 30 | RS | 7-Cl | CH=CH | $S(CH_2)_2CO_2H$ | $(CH_2)_2(1,2\text{-phe})CH(CF_3)OH$ |
| 31 | S | 7-Cl | CH=CH | $SCH_2(R)CHMeCO_2H$ | $(CH_2)_2(1,2\text{-phe})CMe_2OH$ |
| 32 | S | 7-Cl | CH=CH | $SCH_2(S)CHEtCO_2H$ | $(CH_2)_2(1,2\text{-phe})CMe_2OH$ |

TABLE I-continued

I'

| EX. | * | R¹ | Y | A | B |
|---|---|---|---|---|---|
| 33 | RS | 7-Cl | CH=CH | SCH₂CMe₂CO₂H | (CH₂)₂(1,2-phe)CMe₂OH |
| 34 | RS | 7-Cl | CH=CH | SCH₂CHEtCO₂H | (CH₂)₂(1,3-phe)CMe₂OH |
| 35 | RS | 7-Cl | CH=CH | SCH₂CHEtCO₂H | (CH₂)₂(1,2-phe)C(CF₃)₂OH |
| 36 | RS | H | CH=CH | SCH₂CHMeCO₂H | (CH₂)₂(1,2-phe)CMe₂OH |
| 37 | RS | H | CH=CH | SCH₂CHEtCO₂H | (CH₂)₂(1,2-phe)CMe₂OH |
| 38 | RS | 7-Cl | CH=CH | SCH₂CHEtCO₂H | (CH₂)₂(4-Br-1,2-phe)CMe₂OH |
| 39 | RS | 7-Cl | CH=CH | SCH₂CHEtCO₂H | (CH₂)₂(1,2-phe)CMeEtOH |
| 40 | RS | 7-Cl | CH=CH | SCH₂CHEtCO₂H | (CH₂)₂(1,2-phe)CEt₂OH |
| 41 | RS | 7-Cl | CH=CH | SCH₂CHEtCO₂H | (CH₂)₂(1,2-phe)C((CH₂)₃)OH |
| 42 | RS | 7-Cl | CH=CH | SCH₂CHMeCO₂H | (CH₂)₂(1,2-phe)CMe₂NH₂ |
| 43 | RS | 7-Cl | CH=CH | SCH₂CHEtCO₂H | (CH₂)₂(1,2-phe)CHMeNHMe |
| 44 | RS | 7-Cl | CH=CH | SCH₂CHEtCO₂H | (CH₂)₂(1,2-phe)CHMeNMe₂ |
| 45 | RS | 7-Cl | CH=CH | SCH₂CHEtCO₂H | (CH₂)₂(2,5-fur)CMe₂OH |
| 46 | RS | 7-Cl | CH=CH | SCH₂CHEtCO₂H | (CH₂)₂(2,6-pye)CMe₂OH |
| 47 | RS | 7-Cl | CH=CH | SCH₂CHEtCO₂H | (CH₂)₂(4,2-pye)CMe₂OH |
| 48 | RS | 7-Cl | CH=CH | SCH₂CHEtCO₂H | (CH₂)₂(2,5-thio)CMe₂OH |
| 49 | RS | 7-Cl | CH=CH | SCH₂CHEtCO₂H | (CH₂)₂(3,2-pye)CMe₂OH |
| 50 | RS | 7-CN | CH=CH | SCH₂CHEtCO₂H | (CH₂)₂(1,4-phe)CMe₂OH |
| 51 | RS | 7-CF₃ | CH=CH | SCH₂CHEtCO₂H | (CH₂)₂(1,4-phe)CMe₂OH |
| 52 | RS | 7-Cl | CH=CH | SCH₂CHMeCONHS(O)₂Me | (CH₂)₂(1,2-phe)CMe₂OH |
| 53 | RS | 7-NO₂ | CH=CH | SCH₂CHMeCONH₂ | (CH₂)₂(1,2-phe)CMe₂OH |
| 54 | RS | 7-Cl | CH=CH | SCH₂CHMeCONHMe | (CH₂)₂(1,2-phe)CMe₂OH |
| 55 | RS | 7-Cl | CH=CH | SCH₂CHMeTz | (CH₂)₂(1,2-phe)CMe₂OH |
| 56 | RS | 7-Cl | CH=CH | SCH₂CHEtTz | (CH₂)₂(1,2-phe)CMe₂OH |
| 57 | RS | 7-Cl | CH=CH | SCH₂CHEtCONHS(O)₂CF₃ | (CH₂)₂(1,2-phe)CMe₂OH |
| 58 | RS | 7-Cl | CH=CH | SCH₂CHMeNO₂ | (CH₂)₂(1,2-phe)CMe₂OH |
| 59 | RS | 7-Cl | CH=CH | S(CH₂)₂CONHS(O)₂Ph | (CH₂)₂(1,2-phe)CMe₂OH |
| 60 | R | 7-Cl | CH=CH | SCH₂(S)CHEtCO₂H | (CH₂)₂(1,2-phe)CMe₂OH |
| 61 | RS | 7-Cl | CH=CH | S(CH₂)₂CO₂H | (CH₂)₂(1,2-phe)CH₂CMe₂OH |
| 62 | RS | 7-Cl | CH=CH | S(CH₂)₂CMe₂OH | (1,3-phe)CO₂H |
| 63 | RS | 7-Cl | CH=CH | SCH₂CH(n-Pr)CO₂H | (CH₂)₂(1,2-phe)CMe₂OH |
| 64 | RS | 7-Br | CH=CH | SCH₂CHEtCO₂H | (CH₂)₂(1,2-phe)CMe₂OH |
| 65 | S | 7-Cl | CH=CH | SCH₂CH(CH₂CH=CH₂)CO₂H | (CH₂)₂(1,2-phe)CMe₂OH |
| 66 | S | 7-Cl | CH=CH | SCH₂CHEtCO₂H | (CH₂)₂(1,2-phe)CHMeOH |
| 67 | S | 7-Cl | CH=CH | SCH₂CH(CH₂SMe)CO₂H | (CH₂)₂(1,2-phe)CMe₂OH |
| 68 | S | 7-Cl | CH=CH | SCH₂CH(c-Pr)CO₂H | (CH₂)₂(1,2-phe)CMe₂OH |
| 69 | S | 7-Cl | CH=CH | SCH₂CH(CH₂C≡CH)CO₂H | (CH₂)₂(1,2-phe)CMe₂OH |
| 70 | S | 7-Cl | CH=CH | SCH₂CH(CH₂Ph)CO₂H | (CH₂)₂(1,2-phe)CMe₂OH |
| 71 | RS | 7-Cl | CH=CH | SCH₂CHMeCO₂H | (CH₂)₂(1,2-phe)CHMeOH |
| 72 | S | 7-Cl | CH=CH | SCH₂CHPhCO₂H | (CH₂)₂(1,2-phe)CMe₂OH |
| 73 | S | 7-Cl | CH=CH | SCH₂(S)CHEtCO₂H | (CH₂)₂(1,2-phe)CH₂CMe₂OH |
| 74 | S | 7-Cl | CH=CH | SCH₂CHEtCO₂H | (CH₂)₂(1,2-phe)CH₂CHMeOH |
| 75 | S | 7-Cl | CH=CH | SCH₂CH(n-Pr)CO₂H | (CH₂)₂(1,2-phe)CHMeOH |
| 76 | RS | 7-Cl | CH=CH | SCH₂CHEtCO₂H | (1,2-phe)CMe₂OH |
| 77 | S | 7-Cl | CH=CH | SCH₂CHEtCO₂H | (CH₂)₂(1-2-phe)C(CH₂OCH₂)OH |
| 78 | RS | 7-Cl | CH=CH | S(CH₂)₂CMe₂OH | (CH₂)₂(1,2-phe)CO₂H |
| 79 | S | 7-Br | CH=CH | SCH₂(S)CHEtCO₂H | (CH₂)₂(1,2-phe)CMe₂OH |
| 80 | S | 7-Cl | CH=CH | S(CH₂)₂CMe₂OH | (CH₂)₂(1,2-phe)CHMeCO₂H |
| 81 | RS | 7-Cl | CH=CH | S(CH₂)₂CO₂H | CH₂CHOH(1,4-phe)CN |
| 82 | RS | 7-Cl | CH=CH | S(CH₂)₂CO₂H | CH₂CHOH(1,3-phe)CN₄H |
| 83 | RS | 7-Cl | CH=CH | S(CH₂)₂CO₂H | CH₂CHOH(1,4-phe)CN₄H |
| 84 | S | 7-Cl | CH=CH | S(CH₂)₂CO₂H | (CH₂)₂(1,2-phe)CMe₂OH |
| 85 | S | 7-Cl | CH=CH | SCH₂CHCF₃CO₂H | (CH₂)₂(1,2-phe)CMe₂OH |
| 86 | S | 7-Cl | CH=CH | S(CH₂)₃CO₂H | (CH₂)₂(1,2-phe)CMe₂OH |
| 87 | S | 7-Cl | CH=CH | S(CH₂)₂CHMeCO₂H | (CH₂)₂(1,2-phe)CMe₂OH |
| 88 | S | 7-Cl | CH=CH | S(O)₂CH₂(S)CHEtCO₂H | (CH₂)₂(1,2-phe)CMe₂OH |
| 89 | S | 7-Cl | CH=CH | SCH₂CH(CH₂OMe)CO₂H | (CH₂)₂(1,2-phe)CMe₂OH |
| 90 | S | 7-Cl | CH=CH | S(CH₂)₂OMe₂OH | (CH₂)₂(1,2-phe)CO₂H |
| 91 | R | 7-Cl | CH=CH | S(CH₂)₂CMe₂OH | (CH₂)₂(1,2-phe)CO₂H |
| 92 | S | 7-Cl | CH=CH | SCH₂(S)CHEtCO₂H | (CH₂)₂(1,3-phe)CMe₂OH |
| 93 | S | 7-Cl | CH=CH | SCH₂CHEtCO₂H | (CH₂)₂(1,3-phe)(1,1-c-Bu)OH |
| 94 | S | 7-Cl | CH=CH | S(CH₂)₂CMe₂OH | (CH₂)₃(1,2-phe)COOH |
| 95 | R | 7-Cl | CH=CH | S(CH₂)₂CO₂H | S(CH₂)₂(1,1-c-Pen)OH |
| 96 | S | 7-Cl | CH=CH | SCH₂CH(CH₂CF₃)CO₂H | (CH₂)₂(1,2-phe)CMe₂OH |
| 97 | S | 7-Cl | CH=CH | S(CH₂)₂CMe₂OH | (CH₂)₂(4-Cl-1,2-phe)CO₂H |
| 98 | S | 7-Cl | CH=CH | SCH₂CH(n-Pr)CO₂H | (CH₂)₂(1,2-phe)CMe₂OH |
| 99 | R | 7-Cl | CH=CH | SCH₂(S)CHEtCONHS(O)₂Me | (CH₂)₂(1,2-phe)CMe₂OH |
| 100 | S | 7-Cl | CH=CH | S(CH₂)₂CMeOH | (CH₂)₂(1,3-phe)CMe₂CO₂H |

TABLE I-continued

| EX. | * | R¹ | Y | A | B |
|---|---|---|---|---|---|
| 101 | S | 7-Cl | CH=CH | S(CH$_2$)$_2$CMeOH | (CH$_2$)$_2$(1,3-phe)CHMeCO$_2$H |
| 102 | S | 7-Cl | CH=CH | S(CH$_2$)$_3$CMe$_2$OH | (CH$_2$)$_2$(1,2-phe)CO$_2$H |
| 103 | S | 7-Cl | CH=CH | SCH$_2$(S)CHEtCO$_2$H | (CH$_2$)$_2$(1,4-phe)CMe$_2$OH |
| 104 | RS | 7-Cl | CH=CH | S(CH$_2$)$_2$CMe$_2$OH | (CH$_2$)$_2$(1,3-phe)CN$_4$H |
| 105 | S | 7-Cl | CH=CH | S(CH$_2$)$_3$CMe$_2$OH | (CH$_2$)$_2$(1,2-phe)CHMeCO$_2$H |
| 106 | S | 7-Cl | CH=CH | S(CH$_2$)$_3$CMe$_2$OH | (CH$_2$)$_2$(1,2-phe)CHMeCONHS(O)$_2$CH$_3$ |
| 107 | S | 7-Cl | CH=CH | S(CH$_2$)$_2$CMe$_2$OH | (CH$_2$)$_3$(1,2-phe)CO$_2$H |
| 108 | R | 7-Cl | CH=CH | S(O)$_2$CH$_2$(S)CHEtCO$_2$H | (CH$_2$)$_2$(1,2-phe)CMe$_2$OH |
| 109 | S | 7-Cl | CH=CH | S(CH$_2$)$_2$CMe$_2$OH | (CH$_2$)$_2$(4-Cl-1,2-phe)CHMeCO$_2$H |
| 110 | S | 7-Cl | CH=CH | SCH$_2$(S)CHMeCO$_2$H | (CH$_2$)$_2$(1,2-phe)CH$_2$CMe$_2$OH |
| 111 | S | 7-Cl | CH=CH | S(CH$_2$)$_2$CMe$_2$OH | (CH$_2$)$_2$(1,2-phe)CO$_2$Me |
| 112 | S | 7-Cl | CH=CH | S(CH$_2$)$_3$CMe$_2$OH | (CH$_2$)$_2$(4-Cl-1,2-phe)CO$_2$H |
| 113 | R | 7-Cl | CH=CH | S(CH$_2$)$_2$CMe$_2$OH | (CH$_2$)$_2$(4-Cl-1,2-phe)CO$_2$H |
| 114 | S | 7-Cl | CH=CH | S(CH$_2$)$_3$CMe$_2$OH | (CH$_2$)$_2$(1,2-phe)CMe$_2$CO$_2$H |
| 115 | S | 7-Cl | CH=CH | S(CH$_2$)$_2$CMe$_2$OH | (CH$_2$)$_3$(R)CHMe$_2$CO$_2$H |
| 116 | S | 7-Cl | CH=CH | S(CH$_2$)$_3$CEt$_2$OH | (CH$_2$)$_2$(1,2-phe)CO$_2$H |
| 117 | S | 7-Cl | CH=CH | S(CH$_2$)$_3$CEt$_2$OH | (CH$_2$)$_2$(1,2-phe)CHMeCO$_2$H |
| 118 | R | 7-Cl | CH=CH | SCHMeCH$_2$CO$_2$H | (CH$_2$)$_2$(1,2-phe)CMe$_2$OH |
| 119 | S | 7-Cl | CH=CH | S(CH$_2$)$_3$CMe$_2$OH | (CH$_2$)$_2$(1,2-phe)CHEtCO$_2$H |
| 120 | S | 7-Cl | CH=CH | S(CH$_2$)$_3$CMe$_2$OH | (CH$_2$)$_2$(1,2-phe)CH(n-Pr)CO$_2$H |
| 121 | S | 7-Cl | CH=CH | S(CH$_2$)$_3$CMe$_2$OH | (CH$_2$)$_2$(1,2-phe)CH(i-Pr)CO$_2$H |
| 122 | R | 7-Cl | CH=CH | SCH$_2$MeCHMeCO$_2$H | (CH$_2$)$_2$(1,2-phe)CMe$_2$OH |
| 123 | R | 7-Cl | CH=CH | S(CH$_2$)$_2$CMe$_2$OH | (CH$_2$)$_3$(R)CHMeCO$_2$H |
| 124 | R | 7-Cl | CH=CH | SCH$_2$(S)CHMeCN$_4$H | (CH$_2$)$_2$(1,2-phe)CMe$_2$OH |
| 125 | S | 7-Cl | CH=CH | SCH$_2$(S)CHMeCO$_2$H | (CH$_2$)$_2$(3-OH-1,4-phe)CHMeOH |
| 126 | S | 7-Cl | CH=CH | S(CH$_2$)$_3$CHMeOH | (CH$_2$)$_2$(1,2-phe)CHMeCO$_2$H |
| 127 | R | 7-Cl | CH=CH | S(S)CHMeCH$_2$CO$_2$H | (CH$_2$)$_2$(1,2-phe)CMe$_2$OH |
| 128 | R | 7-Cl | CH=CH | S(R)CHMeCH$_2$CO$_2$H | (CH$_2$)$_2$(1,2-phe)CMe$_2$OH |
| 129 | R | 7-Cl | CH=CH | S(S)CHMe(S)CHMeCO$_2$H | (CH$_2$)$_2$(1,2-phe)CMe$_2$OH |
| 130 | R | 7-Cl | CH=CH | S(R)CHMe(R)CHMeCO$_2$H | (CH$_2$)$_2$(1,2-phe)CMe$_2$OH |
| 131 | R | 7-Cl | CH=CH | SCHEtCH$_2$CO$_2$H | (CH$_2$)$_2$(1,2-phe)CMe$_2$OH |
| 132 | S | 7-Cl | CH=CH | S(CH$_2$)$_3$CHMeOH | (CH$_2$)$_2$(1,2-phe)CHEtCO$_2$H |
| 133 | S | 7-Cl | CH=CH | SCH$_2$(S)CHMeCO$_2$H | (CH$_2$)$_2$(4-OMe-1,2-phe)CMe$_2$CO$_2$H |
| 134 | R | 7-Cl | CH=CH | SCMe$_2$CH$_2$CO$_2$H | (CH$_2$)$_2$(1,2-phe)CMe$_2$OH |
| 135 | R | 7-Cl | CH=CH | SCH$_2$CHMeCH$_2$CO$_2$H | (CH$_2$)$_2$(1,2-phe)CMe$_2$OH |
| 136 | R | 7-CF$_3$ | CH=CH | SCH$_2$CMe$_2$CH$_2$CO$_2$H | (CH$_2$)$_2$(1,2-phe)CMe$_2$OH |
| 137 | S | 7-CN | CH=CH | SCH$_2$CMe$_2$CH$_2$CO$_2$H | (CH$_2$)$_2$(1,2-phe)CO$_2$H |
| 138 | S | 7-Cl | CH=CH | S(CH$_2$)$_3$CMe$_2$OH | (CH$_2$)$_2$(1,2-phe)(R)CHEtCO$_2$H |
| 139 | S | 7-Cl | CH=CH | S(CH$_2$)$_3$CMe$_2$OH | (CH$_2$)$_2$(1,2-phe)(S)CHEtCO$_2$H |
| 140 | S | 7-Cl | CH=CH | S(CH$_2$)$_3$CMe$_2$OH | (CH$_2$)$_2$(4-Cl-1,2-phe)CHEtCO$_2$H |
| 141 | S | 7-Cl | CH=CH | S(CH$_2$)$_3$CMe$_2$OH | (CH$_2$)$_2$(1,2-phe)CEt$_2$CO$_2$H |
| 142 | S | 7-Cl | CH=CH | S(CH$_2$)$_3$CMe$_2$OH | (CH$_2$)$_2$(1,2-phe)CH$_2$CO$_2$H |
| 143 | S | 7-Cl | CH=CH | S(CH$_2$)$_3$CMe$_2$OH | (CH$_2$)$_2$(1,2-phe)CH(OH)CO$_2$H |
| 144 | S | 7-Cl | CH=CH | S(CH$_2$)$_3$CMe$_2$OH | (CH$_2$)$_2$(1,2-phe)CHEtCO$_2$H |
| 145 | S | 7-Cl | CH=CH | S(CH$_2$)$_3$CMe$_2$OH | (CH$_2$)$_2$CHMeCH$_2$CO$_2$H |
| 146 | R | 7-Cl | CH=CH | SCH$_2$CMe$_2$CH$_2$CO$_2$H | (CH$_2$)$_2$(1,2-phe)CMe$_2$OH |
| 147 | S | 7-Cl | CH=CH | S(CH$_2$)$_4$CMe$_2$OH | (CH$_2$)$_2$(1,2-phe)CHEtCO$_2$H |
| 148 | S | 6-Cl | CH=CH | S(CH$_2$)$_3$CMe$_2$OH | (CH$_2$)$_2$(1,2-phe)CO$_2$H |
| 149 | S | 8-Cl | CH=CH | S(CH$_2$)$_3$CMe$_2$OH | (CH$_2$)$_2$(1,2-phe)CO$_2$H |
| 150 | S | 7-F | CH=CH | S(CH$_2$)$_3$CMe$_2$OH | (CH$_2$)$_2$(1,2-phe)CHEtCO$_2$H |
| 151 | S | 7-Br | CH=CH | S(CH$_2$)$_3$CMe$_2$OH | (CH$_2$)$_2$(1,2-phe)CHMeCO$_2$H |
| 152 | S | 7-I | CH=CH | SCH$_2$C(1,1-c-Pr)CH$_2$CO$_2$H | (CH$_2$)$_2$(1,2-phe)CMe$_2$OH |
| 153 | S | 7-NO$_2$ | CH=CH | SCH$_2$C(1,1-c-Pr)CH$_2$CO$_2$H | (CH$_2$)$_2$(1,2-phe)CMe$_2$OH |
| 154 | R | 7-N$_3$ | CH=CH | SCH$_2$C(1,1-c-Pr)CH$_2$CO$_2$H | (CH$_2$)$_2$(1,2-phe)CMe$_2$OH |
| 155 | RS | 7-Cl | CH=CH | S(CH$_2$)$_2$CMe$_2$OH | (CH$_2$)$_2$CMe$_2$CH$_2$CO$_2$H |
| 156 | R | 7-Cl | CH=CH | S(1,2-phe)CH$_2$CO$_2$H | (CH$_2$)$_2$(1,2-phe)CMe$_2$OH |
| 157 | S | 7-Cl | CH=CH | S(CH$_2$)$_3$CMe$_2$OH | (CH$_2$)$_2$(1,2-phe)CHEtCO$_2$H |
| 158 | S | 7-Cl | CH=CH | S(CH$_2$)$_2$CMe$_2$OH | (CH$_2$)$_2$(1,2-phe)CHEtCO$_2$H |
| 159 | S | 7-Cl | CH=CH | S(CH$_2$)$_3$CMe(4-Cl-Ph)OH | (CH$_2$)$_2$(1,2-phe)CHEtCO$_2$H |
| 160 | R | 7-Cl | CH=CH | SCH$_2$(1,2-phe)CMe$_2$OH | (CH$_2$)$_2$CMe$_2$CH$_2$CO$_2$H |
| 161 | R | 7-Cl | CH=CH | SCH$_2$(1,1-c-Pr)CH$_2$CO$_2$H | (CH$_2$)$_2$(1,2-phe)CMe$_2$OH |
| 162 | R | 7-Cl | CH=CH | SCH$_2$(1,1-c-Bu)CH$_2$CO$_2$H | (CH$_2$)$_2$(1,2-phe)CMe$_2$OH |
| 163 | R | 7-Cl | CH=CH | SCH$_2$CMe$_2$CHMeCO$_2$H | (CH$_2$)$_2$(1,2-phe)CMe$_2$OH |
| 164 | S | 7-Cl | CH=CH | SCH$_2$(1,2-phe)CMe$_2$OH | (CH$_2$)$_2$CMe$_2$CH$_2$CO$_2$H |
| 165 | R | 7-Cl | CH=CH | SCHMeCMe$_2$CH$_2$CO$_2$H | (CH$_2$)$_2$(1,2-phe)CMe$_2$OH |
| 166 | R | 7-Cl | CH=CH | S(1,1-c-Pr)CH$_2$CO$_2$H | (CH$_2$)$_2$(1,2-phe)CMe$_2$OH |
| 167 | R | 7-Cl | CH=CH | S(1,1-c-Pr)CHMeCO$_2$H | (CH$_2$)$_2$(1,2-phe)CMe$_2$OH |

TABLE II

ELEMENTAL ANALYSES

| EX. | FORMULA | CALCULATED C | H | N | FOUND C | H | N |
|---|---|---|---|---|---|---|---|
| 81 | $C_{30}H_{24}ClN_2O_3SNa.1.5H_2$ | 62.33 | 4.71 | 4.85 | 62.23 | 4.67 | 4.71 |
| 82 | $C_{30}H_{24}ClN_5O_3SNa_2.4.5H_2O$ | 51.69 | 4.77 | 10.05 | 51.72 | 4.55 | 10.04 |
| 83 | $C_{30}H_{24}ClN_5O_3SNa_2.4H_2O$ | 52.37 | 4.69 | 10.18 | 52.47 | 4.54 | 10.25 |
| 85 | $C_{33}H_{30}ClF_3NNaO_3S.3H_2O$ | 57.32 | 5.26 | 2.07 | 57.43 | 5.26 | 2.03 |
| 86 | $C_{33}H_{33}ClNO_3SNa.3.5H_2O$ | 61.43 | 6.25 | 2.17 | 61.43 | 6.17 | 2.16 |
| 87 | $C_{34}H_{35}ClNO_3SNa.3.5H_2O$ | 61.95 | 6.42 | 2.12 | 61.84 | 6.47 | 2.12 |
| 88 | $C_{34}H_{35}NO_5ClSNa.2.5H_2O$ | 60.66 | 5.99 | 2.08 | 61.01 | 5.80 | 1.91 |
| 89 | $C_{34}H_{37}NO_4ClSNa.3.5H_2O$ | 60.31 | 6.55 | 2.07 | 60.11 | 6.15 | 2.02 |
| 90 | $C_{32}H_{31}ClNO_3SNa.2H_2O$ | 63.62 | 5.84 | 2.32 | 63.13 | 5.86 | 2.24 |
| 91 | $C_{32}H_{31}ClNNaO_3S.H_2O$ | 65.58 | 5.68 | 2.39 | 65.72 | 5.72 | 2.79 |
| 92 | $C_{34}H_{35}ClNO_3SNa$ | 68.50 | 5.92 | 2.35 | 68.62 | 6.21 | 2.26 |
| 93 | $C_{35}H_{35}ClNO_3SNa.1.5H_2O$ | 66.24 | 5.99 | 2.20 | 66.01 | 5.94 | 1.93 |
| 94 | $C_{33}H_{33}ClNO_3SNa.H_2O$ | 66.04 | 5.88 | 2.33 | 65.96 | 5.95 | 2.34 |
| 95 | $C_{28}H_{29}ClNO_3S_2Na.2.1H_2O$ | 57.03 | 5.71 | 2.38 | 57.20 | 5.98 | 2.40 |
| 96 | $C_{34}H_{32}ClF_3NNaO_3S.2H_2O$ | 59.51 | 5.29 | 2.04 | 59.36 | 5.46 | 2.02 |
| 97 | $C_{32}H_{30}NO_3SCl_2Na.1.5H_2O$ | 61.05 | 5.28 | 2.22 | 60.80 | 4.99 | 2.17 |
| 98 | $C_{35}H_{38}O_3SNCl$ | 71.47 | 6.51 | 2.38 | 71.32 | 6.50 | 2.33 |
| 99 | $C_{35}H_{38}ClN_2O_4S_2Na.2H_2O$ | 59.27 | 5.97 | 3.95 | 59.36 | 5.69 | 3.87 |
| 100 | $C_{35}H_{37}NO_3SClNa.2H_2O$ | 65.05 | 6.40 | 2.17 | 65.23 | 5.91 | 2.05 |
| 101 | $C_{34}H_{35}NO_3SClNa.2H_2O$ | 64.60 | 6.22 | 2.22 | 64.68 | 5.81 | 2.20 |
| 102 | $C_{33}H_{34}O_3SNCl$ | 70.76 | 6.12 | 2.50 | 70.55 | 5.92 | 2.38 |
| 103 | $C_{34}H_{35}NO_3ClSNa.2H_2O$ | 64.05 | 6.18 | 2.21 | 64.09 | 6.27 | 2.13 |
| 104 | $C_{32}H_{31}ClN_5OSNa.3H_2O$ | 59.55 | 4.95 | 10.52 | 59.48 | 5.77 | 10.84 |
| 105 | $C_{36}H_{38}O_3SNCl$ | 71.47 | 6.51 | 2.38 | 71.44 | 6.42 | 2.26 |
| 106 | $C_{36}H_{41}O_4S_2N_2Cl$ | 64.99 | 6.21 | 4.21 | 65.08 | 6.16 | 3.93 |
| 107 | $C_{33}H_{33}ClNO_3SNa.0.5H_2O$ | 66.04 | 5.88 | 2.33 | 65.96 | 5.95 | 2.34 |
| 108 | $C_{34}H_{35}NO_5ClSNa.H_2O$ | 63.20 | 5.77 | 2.17 | 63.02 | 5.78 | 2.10 |
| 109 | $C_{34}H_{34}Cl_2NO_3SNa.H_2O$ | 62.96 | 5.59 | 2.16 | 62.87 | 5.61 | 2.15 |
| 110 | $C_{34}H_{35}ClNO_3SNa.1.3H_2O$ | 65.91 | 6.12 | 2.26 | 65.82 | 5.99 | 2.26 |
| 112 | $C_{33}H_{32}NO_3SCl_2Na.2H_2O$ | 60.74 | 5.56 | 2.15 | 60.79 | 5.26 | 2.03 |
| 113 | $C_{32}H_{30}NO_3SCl_2Na.1.5H_2O$ | 61.05 | 5.28 | 2.22 | 61.10 | 5.00 | 2.15 |
| 114 | $C_{36}H_{39}ClNO_3SNa.1.5H_2O$ | 66.40 | 6.50 | 2.15 | 66.31 | 6.45 | 2.12 |
| 115 | $C_{29}H_{33}NO_3SClNa.0.5H_2O$ | 64.58 | 6.31 | 2.49 | 64.14 | 5.90 | 2.58 |
| 116 | $C_{35}H_{37}ClNO_3SNa.H_2O$ | 66.92 | 6.26 | 2.23 | 67.19 | 6.23 | 2.18 |
| 117 | $C_{37}H_{41}ClNO_3SNa.0.5H_2O$ | 68.66 | 6.54 | 2.16 | 68.66 | 6.00 | 1.63 |
| 118 | $C_{33}H_{33}NO_3ClSNa.1.5H_2O$ | 65.07 | 5.96 | 2.30 | 64.89 | 6.02 | 2.28 |
| 119 | $C_{36}H_{39}ClNNaO_3S.H_2O$ | 67.33 | 6.43 | 2.18 | 66.97 | 6.52 | 2.20 |
| 120 | $C_{37}H_{41}ClNNaO_3S.2.5H_2O$ | 65.04 | 6.79 | 2.05 | 65.38 | 6.53 | 2.09 |
| 121 | $C_{37}H_{41}ClNN_2O_3S.2.5H_2O$ | 65.04 | 6.79 | 2.05 | 64.97 | 6.65 | 1.97 |
| 122 | $C_{34}H_{35}NO_3SNa.2H_2O$ | 64.60 | 6.22 | 2.22 | 64.43 | 6.23 | 2.21 |
| 124 | $C_{33}H_{33}ClNaN_5SO.1.5H_2O$ | 62.58 | 5.74 | 11.06 | 62.52 | 5.97 | 10.87 |
| 126 | $C_{34}H_{35}O_3SNCl$ | 71.25 | 6.15 | 2.44 | 71.21 | 6.28 | 2.36 |
| 127 | $C_{33}H_{33}ClNO_3SNa.H_2O$ | 66.04 | 5.87 | 2.33 | 66.41 | 6.02 | 2.46 |
| 128 | $C_{33}H_{33}ClNO_3SNa.H_2O$ | 66.04 | 5.87 | 2.33 | 66.65 | 5.74 | 2.52 |
| 129 | $C_{34}H_{35}ClNO_3SNa.1.5H_2O$ | 65.59 | 6.10 | 2.25 | 65.62 | 6.06 | 2.30 |
| 130 | $C_{34}H_{35}NO_3ClSNa.H_2O$ | 66.49 | 6.07 | 2.28 | 65.80 | 5.98 | 2.23 |
| 131 | $C_{34}H_{35}NO_3ClSNa.2H_2O$ | 64.65 | 6.02 | 2.21 | 64.71 | 6.02 | 2.09 |
| 134 | $C_{34}H_{35}NO_3ClSNa.2H_2O$ | 64.60 | 6.22 | 2.22 | 64.47 | 5.93 | 2.17 |
| 135 | $C_{34}H_{35}NO_3ClSNa.2.5H_2O$ | 64.60 | 6.22 | 2.22 | 64.63 | 6.16 | 2.21 |
| 138 | $C_{36}H_{40}ClNO_3S$ | 71.80 | 6.69 | 2.33 | 72.11 | 6.79 | 2.03 |
| 141 | $C_{38}H_{43}ClNO_3SNa.0.5H_2O$ | 69.02 | 6.71 | 2.12 | 68.91 | 6.81 | 2.11 |
| 142 | $C_{34}H_{35}ClNO_3SNa.0.5H_2O$ | 67.48 | 6.00 | 2.31 | 67.75 | 6.13 | 2.35 |
| 143 | $C_{34}H_{35}NO_4SClNa.2H_2O$ | 63.00 | 6.06 | 2.16 | 62.49 | 6.52 | 2.37 |
| 145 | $C_{30}H_{35}NO_3SClNa.2H_2O$ | 61.68 | 6.73 | 2.40 | 9.63 | 6.71 | 2.46 |
| 146 | $C_{35}H_{37}NO_3SNaCl.2H_2O$ | 65.05 | 6.40 | 2.17 | 65.32 | 6.23 | 2.14 |
| 147 | $C_{37}H_{42}O_3SNCl$ | 72.11 | 6.87 | 2.27 | 71.98 | 6.85 | 2.05 |
| 156 | $C_{37}H_{33}NO_3SClNa.2H_2O$ | 66.71 | 5.66 | 2.10 | 66.89 | 5.67 | 2.06 |
| 157 | $C_{36}H_{40}O_3SCl$ | 71.80 | 6.69 | 2.33 | 71.17 | 6.58 | 2.22 |
| 160 | $C_{35}H_{37}NO_3SClNa.2H_2O$ | 65.05 | 6.40 | 2.17 | 65.03 | 6.45 | 2.11 |
| 161 | $C_{35}H_{35}NO_3ClSNa.H_2O$ | 67.13 | 5.96 | 2.24 | 67.01 | 5.95 | 1.97 |
| 163 | $C_{36}H_{39}NO_3SClNa.2H_2O$ | 65.49 | 6.56 | 2.12 | 65.17 | 6.65 | 2.13 |
| 164 | $C_{35}H_{37}NO_3SClNa.H_2O$ | 66.92 | 6.26 | 2.23 | 66.89 | 6.19 | 2.19 |
| 165 | $C_{36}H_{39}ClNO_3SNa.0.8H_2O$ | 67.70 | 6.41 | 2.19 | 67.70 | 6.34 | 2.16 |

Methods of Synthesis

Compounds of the present invention can be prepared according to the following methods. Temperatures are in degrees Celsius.

Method A

Bromoacid II is treated with 2 equivalents of a base such as n-butyllithium in a suitable solvent such as THF at −100° C., then at −78° C. to afford III, which is reacted with IV (see EP 206,751, Dec. 30, 1986; EP 318,093, May 31, 1989 and U.S. Pat. No. 4,851,409, Jul. 25, 1989) to yield the hydroxyacid V. (When Y=—C≡C—, compound IV can also be prepared by the methodology of Yamanaka et al., Chem. Pharm. Bull., 27, 270–273 (1979) and by Crisp et al., Aust. J. Chem., 42, 279–285 (1989).)

V is then esterified using conditions such as methanol/ HCl, $CH_2N_2$ or MeI/$K_2CO_3$ and an organometallic reagent is then added to give the diol VI. The benzylic alcohol of VI is then reacted with the thiol IX by: (1) making the chloride by reaction with methanesulfonyl chloride in the presence of triethylamine, and (2) substituting the chloride by the thiol IX in the presence of a base such as sodium hydride or cesium carbonate to afford VII. In the cases where $Q^1$ is an ester, hydrolysis with a base such as NaOH, LiOH or $K_2CO_3$ (followed by acidification) affords the acid VIII. VII and VIII are both representatives of structure I.

Method B

The ketone IV is reduced to the benzylic alcohol using a reagent such as $NaBH_4$. This benzylic alcohol is converted to the benzylic bromide, using conditions such as carbon tetrabromide/1,2-bis(diphenylphosphino)ethane, and treatment with triphenylphosphine affords the phosphonium salt X. Using a base such as potassium hexamethyldisilazide, the ylid of X is formed and is added to a lactol. Oxidation of the benzylic alcohol so obtained using conditions such as (1) $MnO_2$ in EtOAc and (2) $MnO_2$/HCN/MeOH affords the ester XI. The thiol IX is then added to XI using a Lewis acid such as $AlCl_3$ or $TiCl_4$ to give the thioether XII. Reaction of XII with an organometallic compound such as a lithium or a magnesium salt, yield, in the cases where $Q^1$ is stable in these conditions, the tertiary alcohol XIII, which is a representative of structure I.

Method C

The ester XXVII, obtained by Method E, is hydrolyzed with a base such as NaOH to give XIV. XIV is reacted with an organometallic and the reaction mixture is quenched with chlorotrimethylsilane to yield the hydroxyketone XV. The benzylic alcohol is then reacted with methanesulfonyl chloride in the presence of a base such as triethylamine. The mesylate so obtained is substituted by the thiolate derivative of IX to afford XVI. Finally, an organometallic reaction or a reduction using a reagent such as $NaBH_4$ on XVI gives the alcohol XVIII. Using this method, two different R groups can be added to give a secondary or an unsymmetrical tertiary alcohol.

Method D

The hydroxyacid XVII (included within the definition of XIV) is cyclized to the lactone XXI using a reagent such as 2-chloro-N-methylpyridinium iodide. An organometallic reagent is then added to XXI to give the diol XXII. Finally, the secondary alcohol is substituted by the thiol IX as in Method C to yield the thioether XX.

Method E

The aldehyde XXIII, a derivative of IV, is reacted with an organometallic reagent and the benzylic alcohol so obtained is oxidized to XXIV with an oxidant like activated manganese dioxide. XXIV is then reacted with the iodide XXV in the presence of a base such as lithium diisopropylamide to yield the alkylation product XXVI. Reduction with sodium borohydride or addition of an organometallic reagent afford the hydroxyester XXVII, which is then treated as the lactone XXI in Method D to give the thioether XXVIII.

Method F

The enolate of the ketone XXIX, obtained by treatment of XXIX with a base such as KH or NaH, is reacted with dimethylcarbonate to yield the ketoester XXX. XXX is enolized with a base such as NaH and treated with the iodide XXXI, the methyl ester of XXV. The adduct so obtained is then decarboxylated using conditions such as heating with HCl in acetic acid to afford a mixture of the ester XXXII and the corresponding acid. Esterification of the mixture, using a reagent such as diazomethane or methyl iodide and $K_2CO_3$, yields XXXII, which is then converted to XXXIII or its epimer, as described in Method G.

Method G

The hydroxy acid XVII is esterified using conditions such as heating with MeI and $K_2CO_3$ or reacting with diazomethane. Treatment of this hydroxyester with an oxidant such as activated manganese dioxide affords the ketoester XXXIV. The ketone is then reduced using the chiral oxazaborolidine XXXV in the presence of borane/THF complex. Reaction of the ester with an organometallic gives the diol XXXVI, which is chiral XXII. Protection of the secondary alcohol with tert-butylchlorodiphenylsilane in the presence of a base such as 4-(dimethylamino)pyridine, protection of the tertiary alcohol as the 2-tetrahydropyranyl ether and removal of the silyl ether afford XXXVII, The chiral center of XXXVII can be inverted to give XXXVIII using conditions such as: (1) treatment with triphenylphosphine, diethyl azodicarboxylate and an acid such as R-(−)-α-methoxyphenylacetic acid (chiral acid improves the resolution), and (2) hydrolysis of the ester so obtained with a base such as NaOH. Formation of the mesylate and substitution with the thiol IX as in Method C, followed by hydrolysis of the 2-tetrahydropyranyl ether using conditions such as pyridinium p-toluenesulfonate in methanol afford the thioethers XXXIX and XL.

Method H

The bromoaldehyde XLI is reduced with a reagent such as sodium borohydride and the resulting benzylic alcohol is protected as the 2-tetrahydropyranyl ether. The Grignard reaction of XLII on XV afford an hydroxyacid, which is then converted to the ketone XLIII as in Method C. Substitution by the thiol IX is then performed (as in Method C) to afford XLIV. An organometallic reagent is then added to this ketone to yield a tertiary alcohol. In cases where $Q^1$ is an acid, it is protected as the methyl ester using a reagent such as $CH_2N_2$. Deprotection of the benzylic alcohol, followed by an oxidation with a reagent such as $MnO_2$, affords the aldehyde XLV. A Wittig reaction with a phosphonium derivative of a substituted 2-(bromomethyl)quinoline; followed by an hydrolysis step when $Q^1$ is an ester, yield the styrylquinoline XLVI.

Method I

The phenylacetic acid XLVII is reduced to the alcohol XLVIII using a reagent such as borane in tetrahydrofuran. Formation of the alcoholate with one equivalent of a Grignard reagent, followed by treatment with magnesium afford the dimagnesium salt of XLVIII. It is added to a ketone or an aldehyde to yield the alcohol XLIX. The bromide L is then formed using conditions such as (1) formation of the mesylate with methanesulfonyl chloride and triethylamine and (2) substitution of the mesylate by sodium bromide in N,N-dimethyl formamide. The dimagnesium salt of L is then formed as previously described and added to the ketone IV. The adduct LI is then reacted with the thiol IX as in Method C to yield LII.

Method J

The ketoester XXX is treated with the iodide LIII and decarboxylated as in Method F. Reduction of the ketone with a reagent such as $NaBH_4$ yields the alcohol LIV. By reaction with an organometallic in toluene, the nitrile LIV is converted to the amine LV. The thiol IX is then added as in Method C to afford LVI. Reaction of an iodide with the amine LVI gives a secondary or tertiary amine LVII. Both LVI and LVII are representatives of structure I.

Method K

Vinylmagnesium bromide or alkylmagnesium bromide is added to the aldehyde derivative of IV to yield LVIII. Using the procedure of R. C. Larock et al. (Tetrahedron Letters, 30, 6629 (1989), the aryl halide LIX is coupled to the alcohol LVIII to give LX. When $Q^3$ is an ester or an alcohol, LX can be converted to LXI or its epimer, a structure representative of Ia, using the procedure of Method G. Also, when $Q^3$ is $Q^1$, chiral reduction of the ketone LX with XXXV as in Method G followed by formation of the mesylate and substitution by the thiol LXII afords LXIII, a structure representative of Ib.

Method L

The iodide LXIV is converted to a mixed zinc copper organometallic which is added to XXIII in the presence of $BF_3 \bullet Et_2O$. This alcohol LXV is converted to a mesylate and displaced with LXII in the presence of a base such as $Cs_2CO_3$. Alternatively, the alcohol may be oxidized (Swern type) and reduced using catalyst such as B-chlorodiisopinocampheylborane (H. C. Brown et al., J. Am. Soc., 1988, 110, 1539) before mesylation and displacement to give LXVII or its enantiomer.

Method M

The tertiary alcohol of LX is protected first with dihydropyran (DHP) and the ketone is then reduced with (–)-B-chlorodiisopinocampheylborane or as in Method G to give LXVIII. The secondary benzylic alcohol is then coverted to thiolacetate LXIX using the conditions of Volante (Tetrahedron lett., 22, 3119, (1981)). The thiol ester is cleaved by hydrazine or an alkoxide, and the side chain is added by nucleophilic substitution in the presence of a base such as $Cs_2CO_3$. Deprotection of the tertiary alcohol affords LXX, the isomer of LXI.

Methods N, P, Q and R describe the formation of 1-(mercaptomethyl)cyclopropaneacetic acid and its ester, derivatives which are useful for the practice of this invention. Method R is described in more detail in Example 161.

Method N

A diester of itaconic acid is cyclopropanated using $CH_2N_2/Pd(OAc)_2$ (Synthesis, 1981, 714) or $Me_3SI/n$-BuLi (J. Org. Chem., (1973), 38, 3942) or $Me_3SOI/NaH$ (J. Am. Chem. Soc., (1965), 87, 1353) or the Simmons-Smith conditions (J. March, Advanced Organic Chemistry, 3rd Edition, 1985, p. 772–773). The cyclopropane ring can also be prepared by addition of a dihalocarbene and reduction of the dihalocyclopropane so obtained. Hydrolysis of the diester and dehydration of the diacid affords the cyclopropanated succinic anhydride. This anhydride can alternatively be prepared directly by the cyclopropanation of itaconic anhydride. Reduction with $LiAlH_4$ or $NaBH_4$ (Can. J. Chem., 56, 1524 (1978)) and acidification afford the lactone. The lactone is opened to the bromoester with HBr (Helv. Chim. Acta. 63, 2508 (1980)) and the bromide is substituted by KSH (Chem. Abstr. 58 P11490b) or AcSNa. Hydrolysis with KOH affords the mercaptoacid.

Method P

A cuprate reagent is prepared from a bromomethyl sulfide such as bromomethyl benzyl sulfide by reaction with butyllithium and a copper salt. This reagent is alternatively prepared from the tributyltin derivative as shown. 1,4-Addition of this cuprate to an $\alpha,\beta$-unsaturated cyclopropylidene ester yields the protected (1-mercaptomethyl)cyclopropaneacetate. Deprotection with $Na/NH_3$ when Z is a benzyl group, and hydrolysis, afford the mercaptoacid.

Method O 2-(Bromomethyl)acrylate is reacted with a thiol such as benzyl mercaptan. Reduction of the ester with a reagent such as diisobutyl-aluminum hydride gives the primary alcohol. Cyclopropanation of the double bond as in Method N affords 1-(hydroxymethyl)cyclopropanemethylthioether. If the ester is reduced first, then it is preferable to effect the cyclopropanation with $CH_2N_2$ or by the Simmons-Smith procedure. If the ester is to be cyclopropanated first, it is preferable to use one of the sulfonium reagents in Method N. Mesylation of the primary alcohol, substitution by cyanide, hydrolysis of the nitrile and removal of the Z group (with $Na/NH_3$ when Z is benzyl) yield the desired mercapto acid.

Method R

Diethyl 1,1-cyclopropanedicarboxylate is reduced to the diol with a reagent such as $LiAlH_4$ and monoprotected as, for example, a benzoyl ester. The alcohol is mesylated and substituted for a cyanide group. Hydrolysis and esterification affords methyl 1-(hydroxymethyl)cyclopropaneacetate. This hydroxyester can also be prepared from the lactone of Method N. The alcohol is mesylated and substituted by a thiolacerate group. This group can alternatively be introduced by the action of thiolacetic acid/triphenylphosphine/diisopropyl azodicarboxylate (Tetrahedron Lett., 22, 3119 (1981)) on the hydroxyl group. The thiol is then generated in situ with hydrazine.

In the following schemata

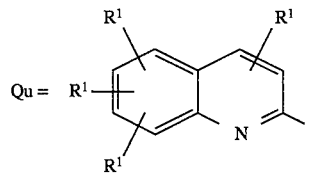

tives which are useful for the practice of this invention. Method R is described in more detail in Example 161.

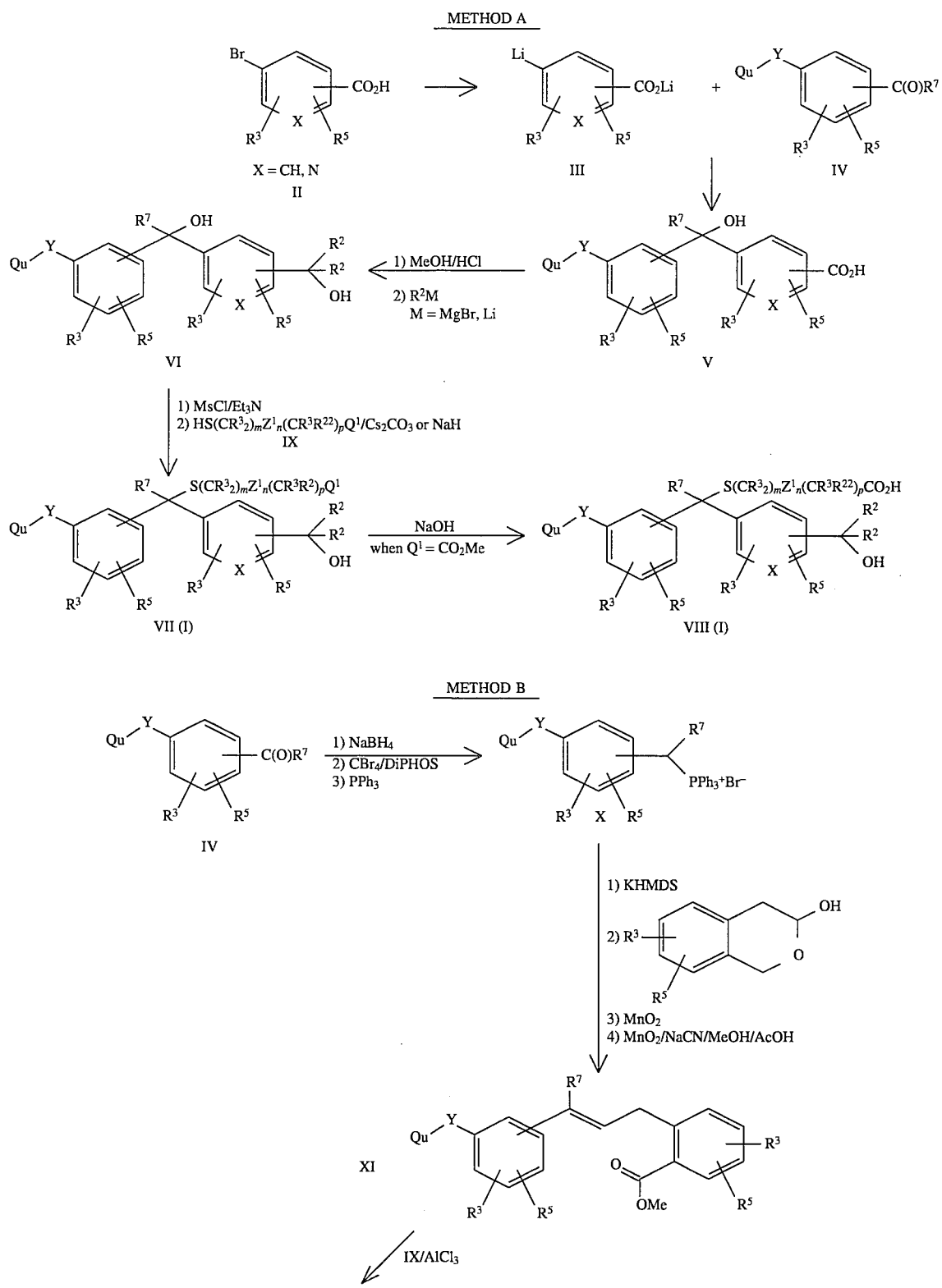

-continued
METHOD B
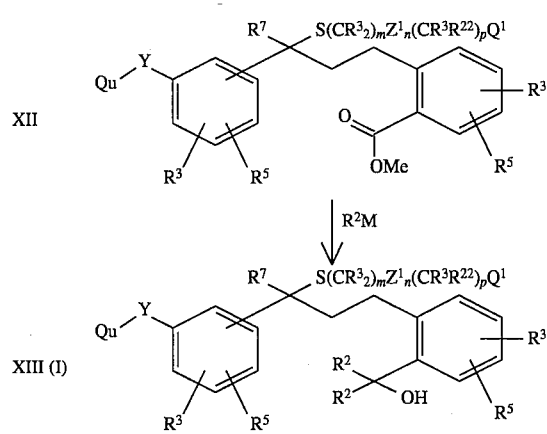
METHOD C
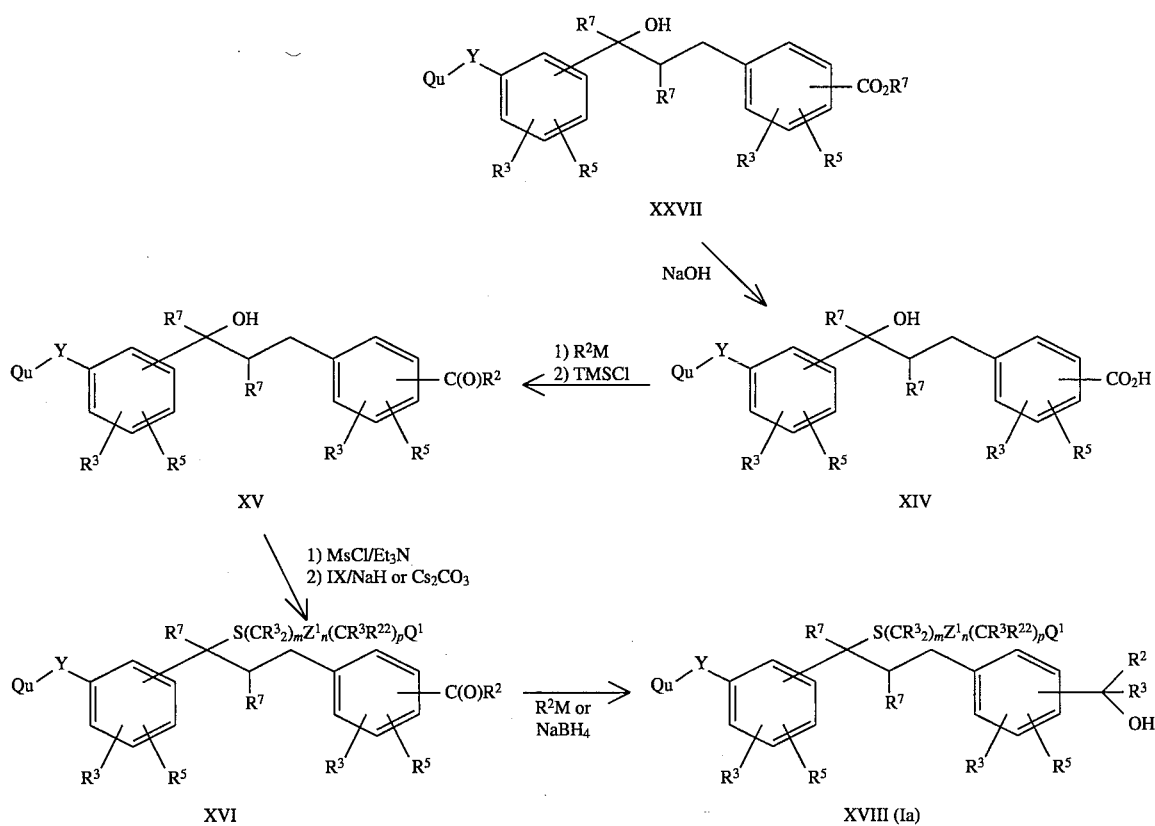

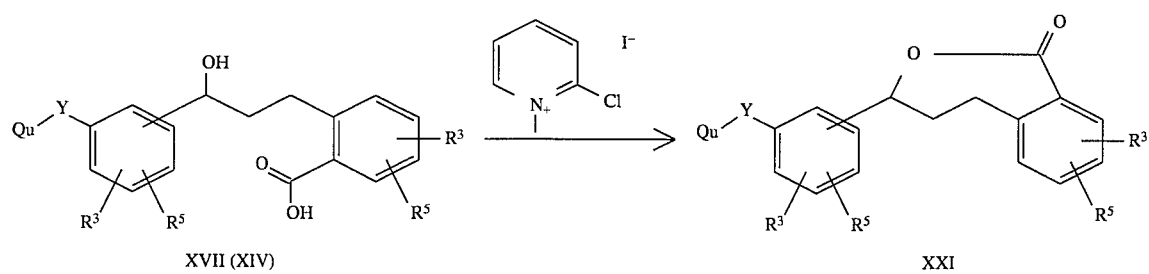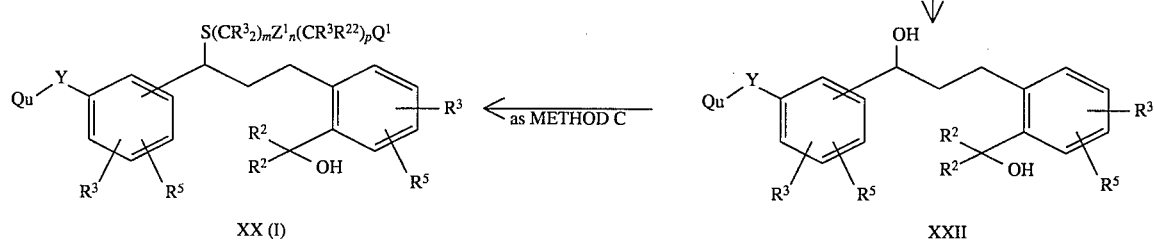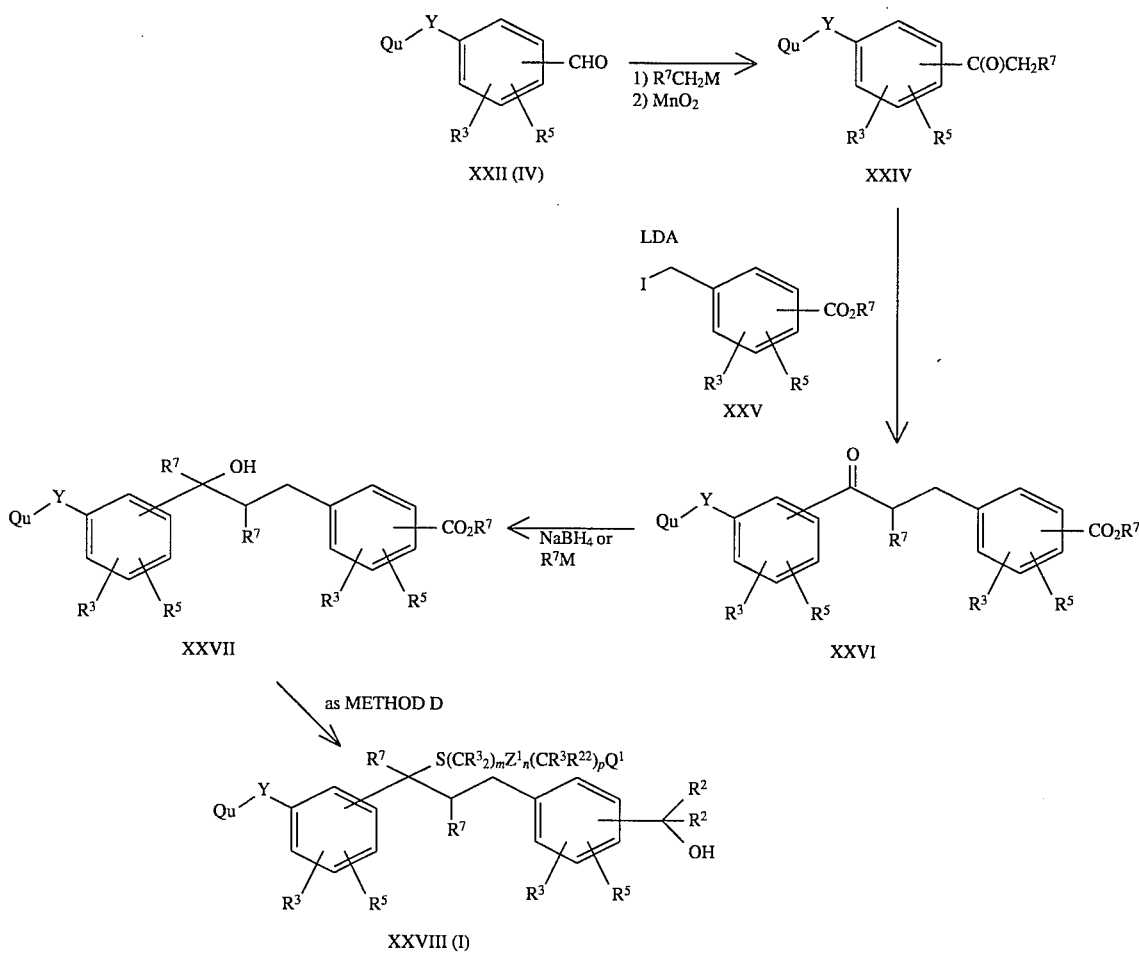

METHOD F
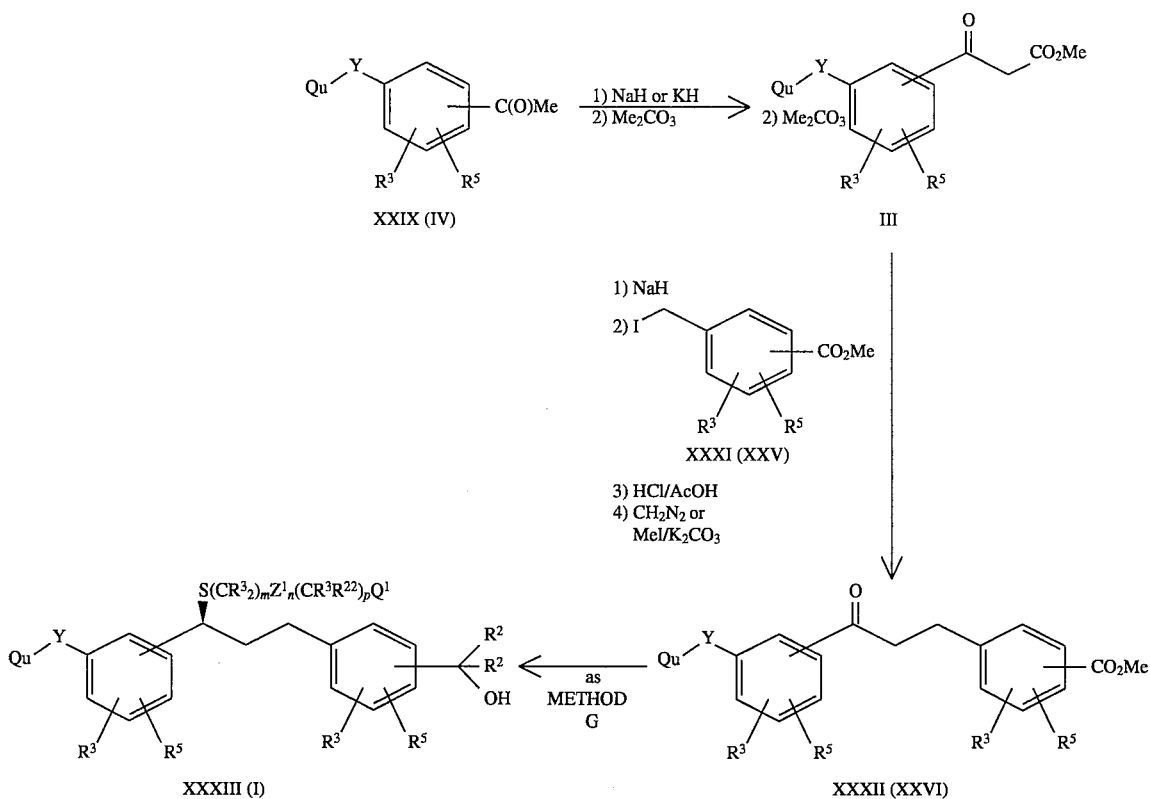
METHOD G
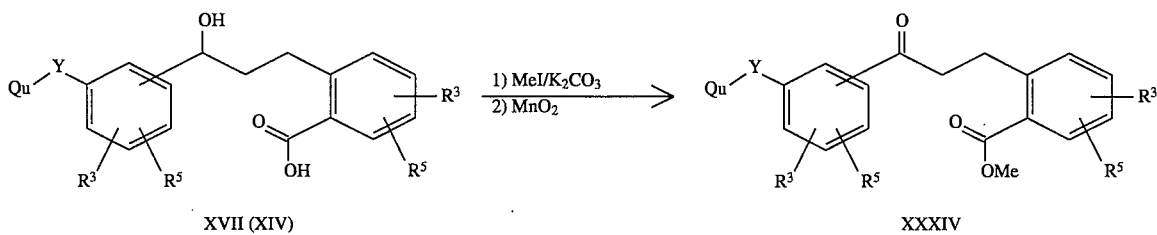
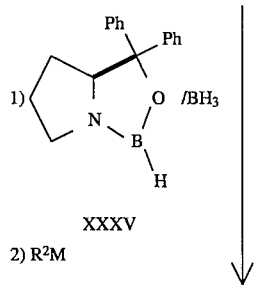

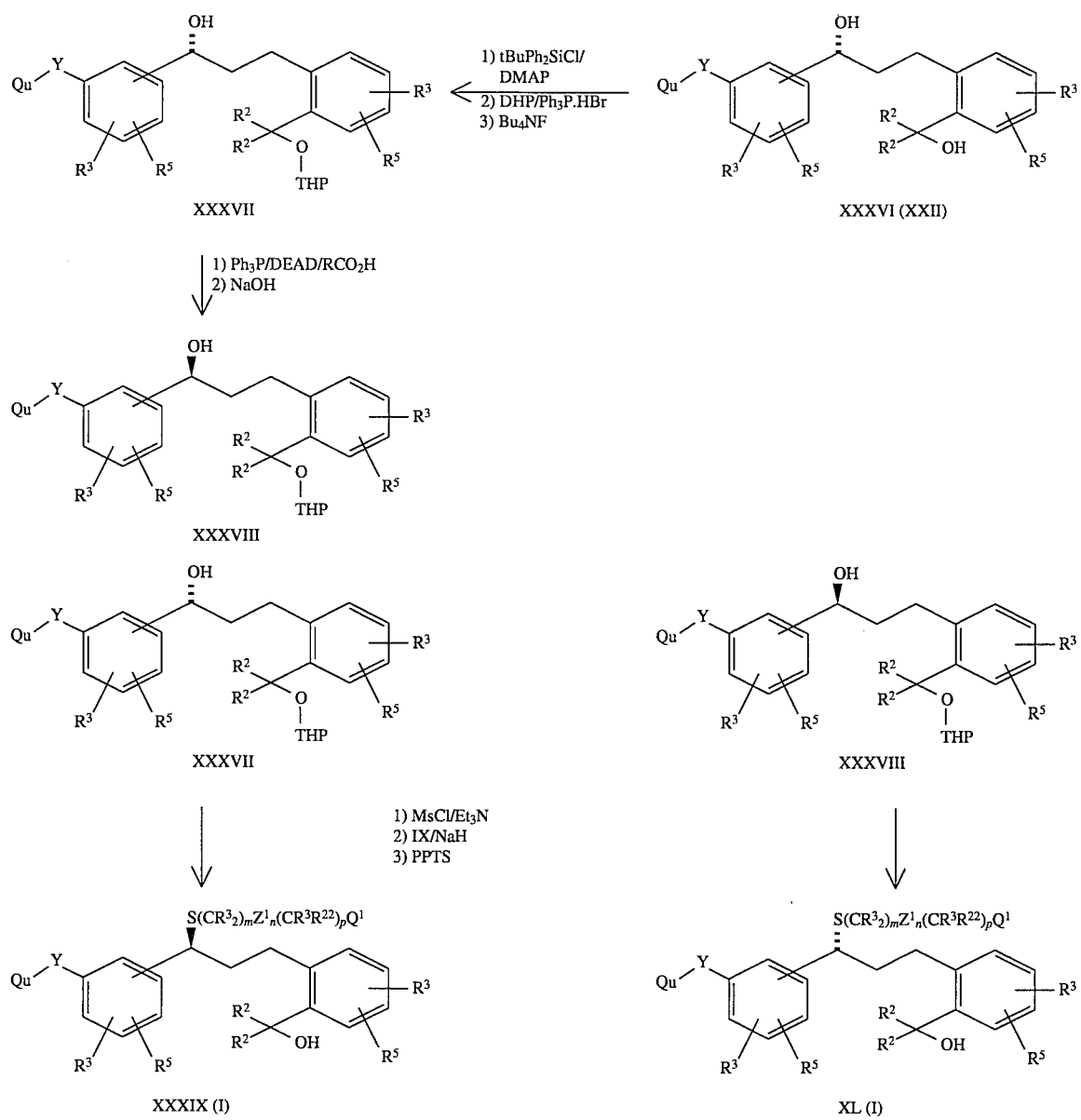
METHOD H
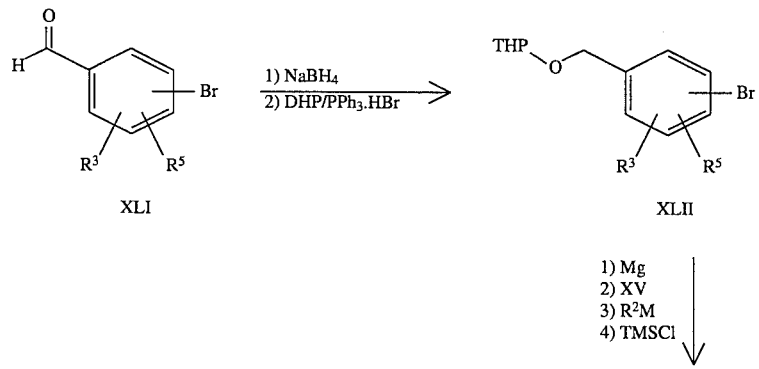

-continued
METHOD H
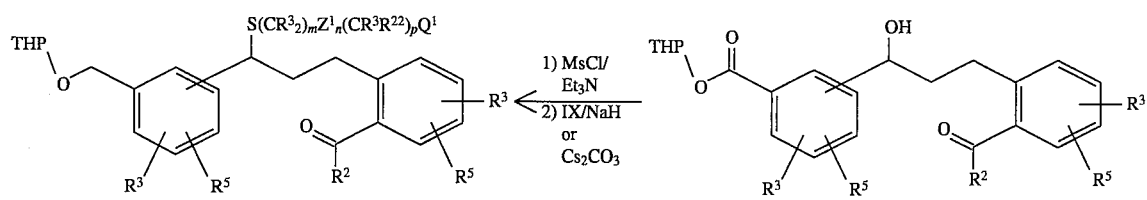
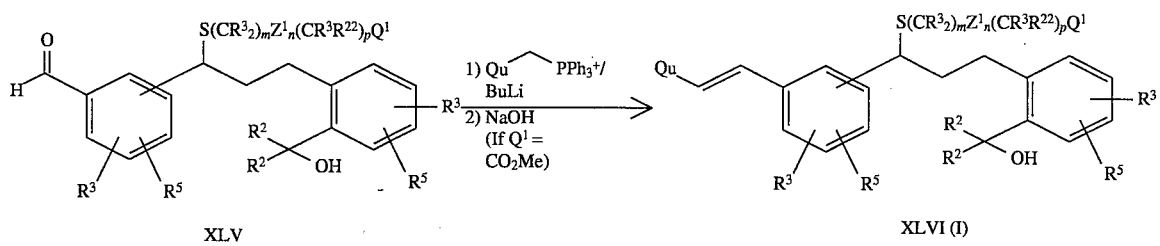
METHOD I
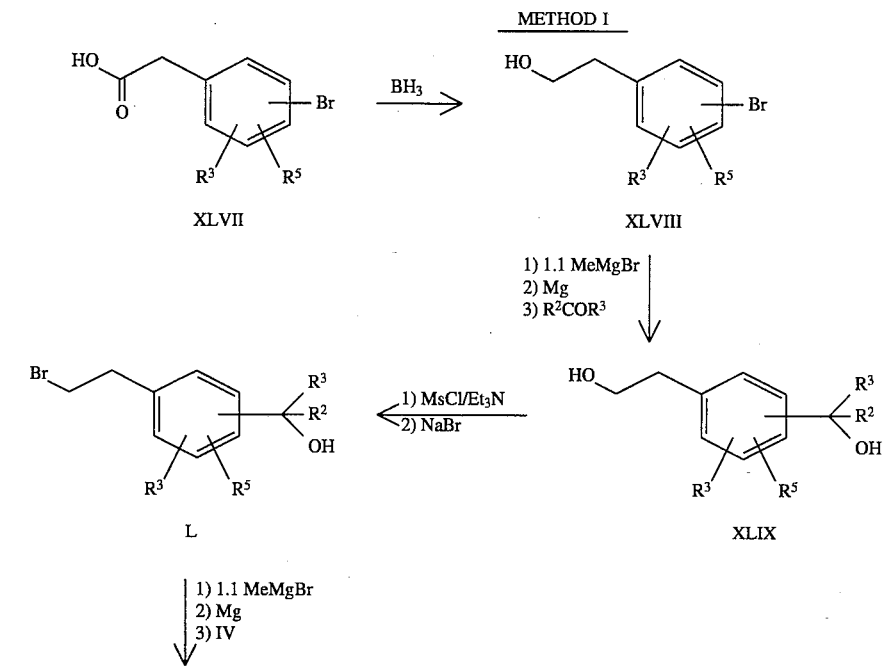
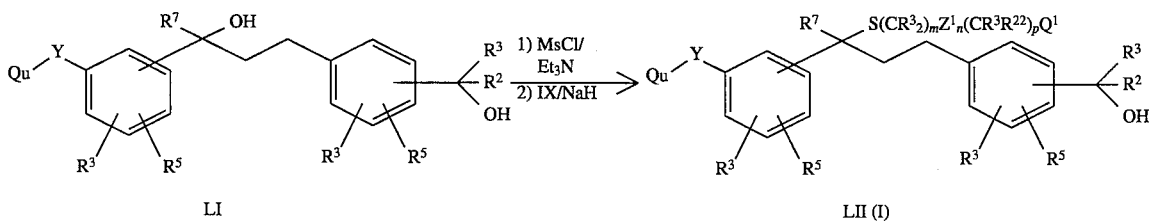

METHOD J
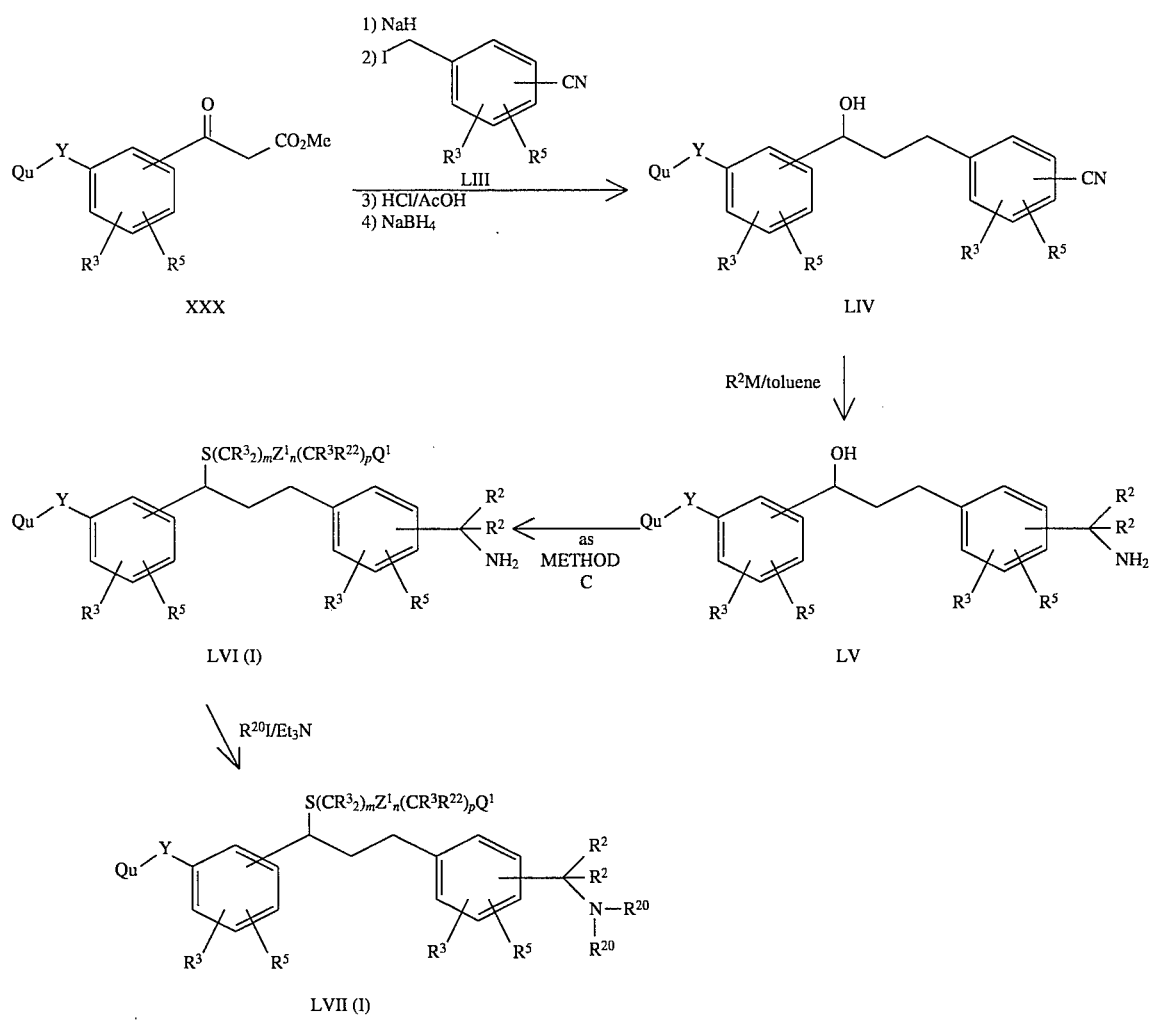
METHOD K
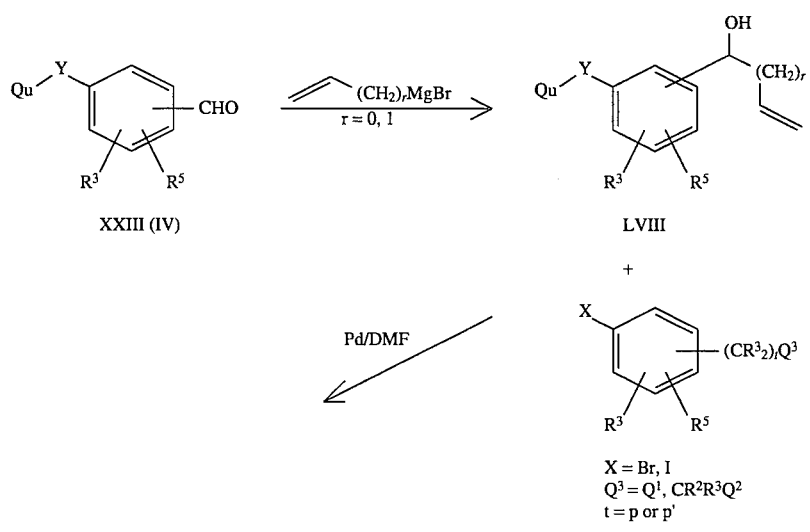

-continued
METHOD K
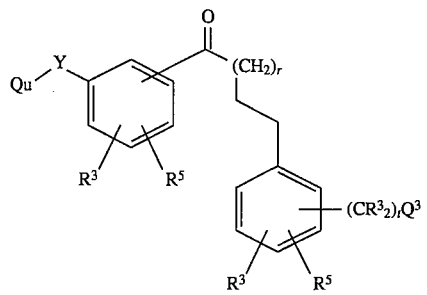
LX
Q³ = CO₂Me, Cr²R³OH
as in METHOD G
Q³ = Q¹
1) chiral reduction
2) MsCl/Et₃N
3) HS(CR³₂)$_{m'}$Z²$_{n'}$(CR³R⁴)$_p$·CR²R³OH
(LXII) /NaH or Cs₂CO₃
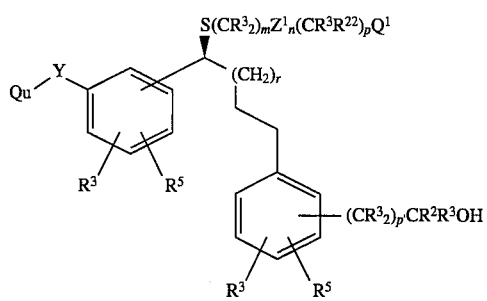
LXI (Ia)
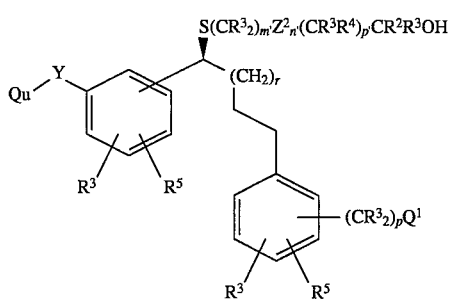
LXIII (Ib)
METHOD L
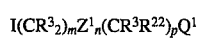
LXIV
1) Zn
2) CuCN
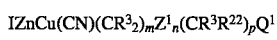
XXIII (IV) + BF₃OEt₂
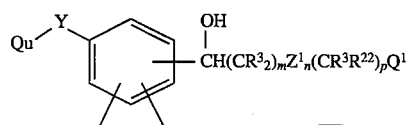
LXV
as method K
1) (COCl)₂, DMSO
2) as in method K -continued
METHOD L
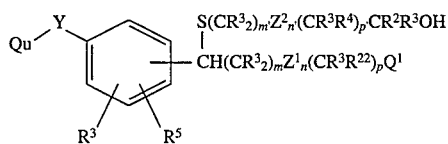
LXVI
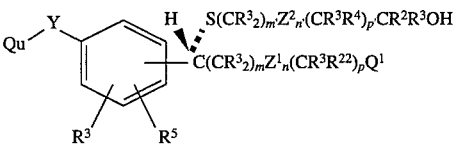
LXVII
METHOD M
LX (Q³ = CR²R³OH) →  1) DHP  2) chiral reduction
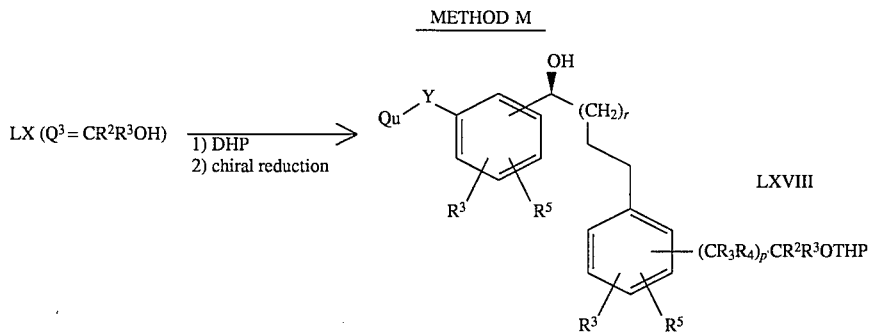
LXVIII
↓ Ph₃P/DIAD
  AcSH
LXIX
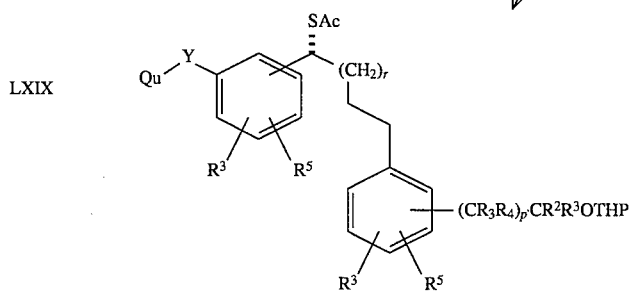
↓ 1) NH₂NH₂ or MeONa
  2) W(CR³₂)ₘZ¹ₙ(CR³R²²)ₚQ¹
     W = Br, I, OMs
  3) PPTS/MeOH
LXX (LXI)
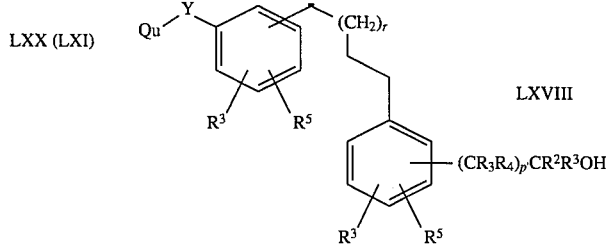
LXVIII

METHOD N
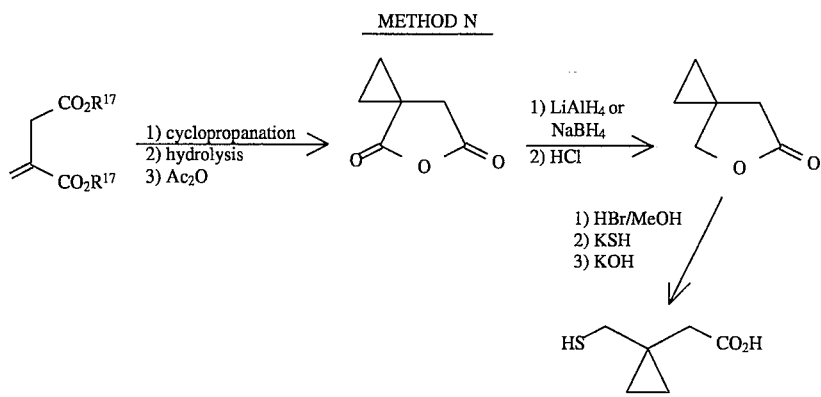
METHOD P
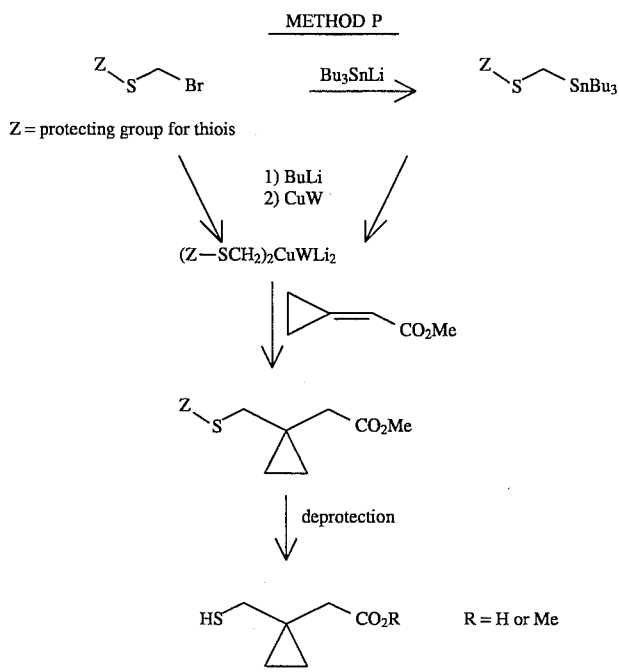
METHOD Q
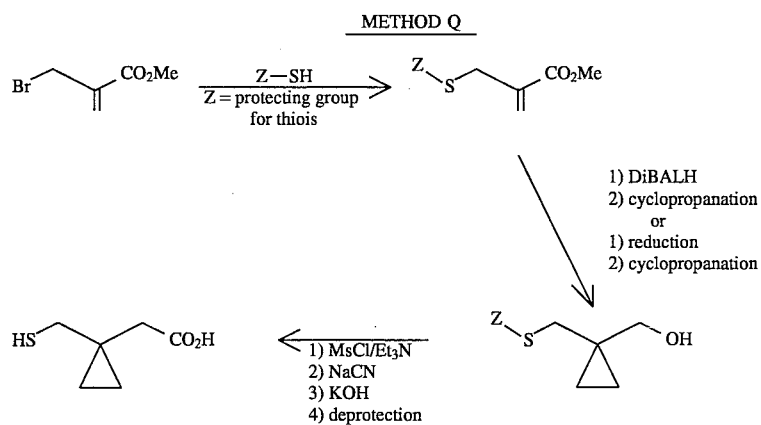

METHOD R

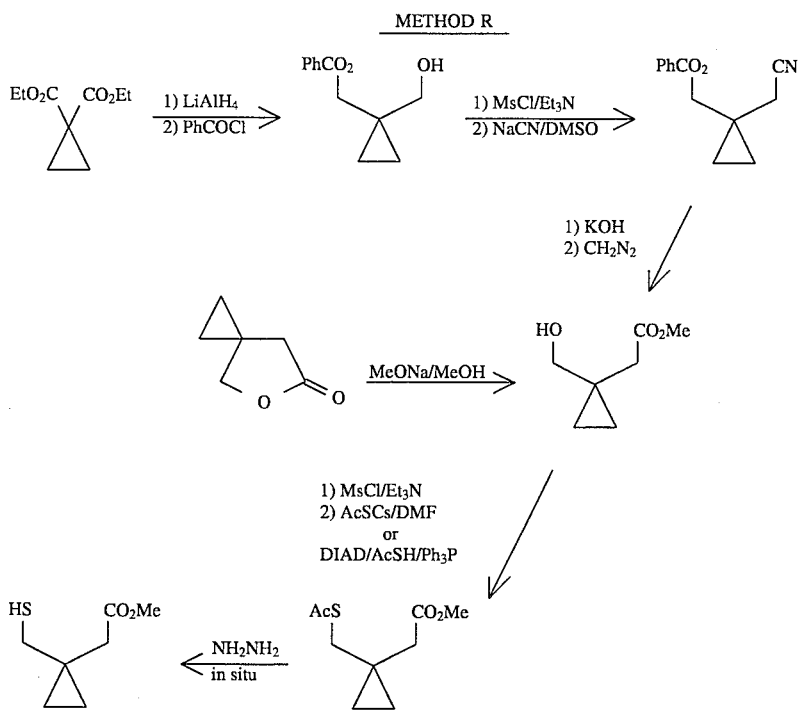

Assays for Determining Biological Activity

Compounds of Formula I can be tested using the following assays to determine their mammalian leukotriene antagonist activity and their ability to inhibit leukotriene biosynthesis.

The leukotriene antagonist properties of compounds of the present invention were evaluated using the following assays.

LTD$_4$ Receptor Binding Studies in Guinea Pig Lung Membranes, Guinea Pig Trachea and In vivo Studies in Anesthetized Guinea Pigs A complete description of these three tests is given by T. R. Jones et al., Can. J. Physiol. Pharmacol., 67, 17–28 (1989).

Compounds of Formula I were tested using the following assays to determine their mammalian leukotriene biosynthesis inhibiting activity.

Determination of Inhibition of 5-Lipoxygenase

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (*Biochem. Biophys. Res. Commun.*, 141, 534–540, (1986)) with minor modifications. The incubation mixture contained 25 mM Na$^+$/K$^+$phosphate buffer, pH 7.3, 1 mM ATP, 0.5 mM CaCl$_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 min at 37° C., the reaction was stopped by adding 0.8 mL of diethyl ether/methanol/1M citric acid (30:4:1). The samples were centrifuged at 1,000×g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 min incubation.

Human Polymorphonuclear (PMN) Leukocyte LTB$_4$ Assay

A. Preparation of Human PMN

Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PHNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at 5×10$^5$ cells/mL in HEPES (15 mM)-buffered Hanks balanced salt solution containing Ca$^{2+}$ (1.4 mM) and Mg$^{2+}$ (0.7 mM), pH 7.4. Viability was assessed by Trypan blue exclusion and was typically greater than 98%.

(1) Boyum, A. *Scand. J. Clin. Lab. Invest.*, (21 (Supp 97), 77 (1968).

B. Generation and Radioimmunoassay of LTB$_4$

PMNs (0.5 mL; 2.5×10$^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore $A_{23187}$ (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 mL) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-$LTB_4$ (10 nCi in 100 mL RIA buffer) and $LTB_4$-antiserum (100 mL of a 1:3000 dilution in RIA buffer) were added and the tubes vortexed. Reactants were allowed to equilibrate by incubation overnight at 4° C. To separate antibody-bound from free $LTB_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound $LTB_4$ were decanted into vials and Aquasol 2 (4 mL) was added. Radioactivity was quantified by liquid scintillation spectrometry. Preliminary studies established that the amount of methanol carried into the radioimmuno-assay did not influence the results. The specificity of the antiserum and the sensitivity of the procedure have been described by Rokach et al.[2] The amount of $LTB_4$ produced in test and control (approx. 20 ng/$10^6$ cells) samples were calculated. Inhibitory dose-response curves were constructed using a four-parameter algorithm and from these the $IC_{50}$ values were determined.

(2) Rokach, J.; Hayes, E. C.; Girard, Y.; Lombardo, D. L.; Maycock, A. L.; Rosenthal, A. S.; Young, R. N.; Zamboni, R.; Zweerink, H. J. *Prostaglandins Leukotrienes and Medicine*, 13, 21 (1984).

Compounds of Formula I were tested in the following assays to determine their in vivo activity as both leukotriene antagonist and leukotriene biosynthesis inhibitor.

Asthmatic Rat Assay

Rats are obtained from an inbred line of asthmatic rats. Both female (190–250 g) and male (260–400 g) rate are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions 22, 63–68 (1987)).

Prevention of Induced Bronchoconstriction in Allergic Sheep

A. Rationale

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.) and b) they have previously responded to inhalation challenge with *Ascaris suum* with both an acute bronchoconstriction and a late bronchial obstruction (Abraham, W. M., Delehunt, J. C., Yerger, L. and Marchette, B., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimensions, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transducer catheter system reveals no phase shift between pressure and flow to a frequency of 9 Hz. For the measurement of pulmonary resistance ($R_L$), the maximal end of the nasotracheal tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems

Aerosols of *Ascaris suum* extract (1:20) are generated using a disposable medical nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol

Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1,2,3,4,5,6,6.5,7,7.5 and 8 hr after antigen challenge. Placebo and drug tests are separated by at least 14 days. In a further study, sheep are given a bolus dose of the test compound followed by an infusion of the test compound for 0.5–1 hr prior to ascaris challenge and for 8 hr after ascaris as described above.

Statistical Analysis

A Kruskal-Wallis one way ANOVA test was used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 4

Sodium 3-((1-(3-(2-(7-chloro-2-quinolinyl)ethenyl)phenyl)-1-(3-(2-hydroxy-2-propyl)phenyl)methyl)thio)- 2-methyl-propanoate Step 1

3-((3-(2-(7-chloro-2-quinolinyl)ethenyl)phenyl)hydroxymethyl)benzoic acid

To the dilithium salt (5.92 mmol) obtained from 3-bromobenzoic acid (W. E. Parham and Y. A. Sayed, J. Org. Chem., 39, 2051 (1974)), a solution of 3-(2-(7-chloro-2-quinolinyl)ethenyl)benzaldehyde (1.503 g, 5.12 mmol) (U.S. Pat. No. 4,851,409, Jul. 25, 1989, Example 24, Step 1) in THF (25 mL) was added dropwise at −78° C. The mixture was stirred for 2 h at −78° C. and was quenched with 25% aqueous NH$_4$OAc. The mixture was acidified to pH 5 with AcOH and extracted with EtOAc. The organic fractions were dried over Na$_2$SO$_4$ and evaporated. Flash chromatography of the residue on silica using EtOAc:toluene:AcOH 30:70:1 yielded the title compound.

$^1$H NMR (CD$_3$COCD$_3$/CD$_3$SOCD$_3$): δ 5.90 (1H, s), 6.00 (1H, s, OH), 7.36–7.58 (5H, m), 7.62 (1H, d), 7.73 (1H, d), 7.82–8.02 (6H, m), 8.13 (1H, s), 8.37 (1H, d).

Step 2

Methyl 3-((3-(2-(7-chloro-2-quinolinyl)ethenyl)phenyl)hydroxymethyl)benzoate

To a solution of HCl in MeOH, prepared from acetyl chloride (10.0 mL, 141 mmol) in 80 mL MeOH at 0° C., the hydroxyacid of Step 1 (1.960 g, 4.71 mmol) was added and the mixture was stirred at r.t. for 4 days. It was then poured into 400 mL of cold 25% aq NH$_4$OAc and 100 mL of THF. The ester was extracted with EtOAc:THF 1:1, dried over Na$_2$SO$_4$ and purified by flash chromatography on silica with EtOAc:toluene 10:90 and 20:80. Yield: 1.653 g, 82%.

$^1$H NMR (CD$_3$COCD$_3$/CD$_3$SOCD$_3$): δ 3.85 (3H, s), 5.92 (1H, d), 6.09 (1H, d, OH), 7.36–7.53 (4H, m), 7.56 (1H, d), 7.62 (1H, d), 7.75 (1H, d), 7.82–8.03 (6H, m), 8.13 (1H, br s), 8.37 (1H, d).

Step 3

3-((3-(2-(7-chloro-2-quinolinyl)ethenyl)phenyl)hydroxymethyl)-α,α-dimethylbenzenemethanol To a solution of the ester of Step 2 in toluene at 0° C., MeMgCl (3 equiv.) was added dropwise. The reaction mixture was stirred a further hour at room temperature and was quenched with 25% NH$_4$OAc. Extraction with EtOAc and flash chromatography of the residue afforded the title tertiary alcohol in 86% yield.

¹H NMR (CDCl₃/CD₃SOCD₃): δ 1.50 (6H, s), 4.70 (1H, s, OH), 5.72 (1H, d, OH), 5.80 (1H, d), 7.27 (1H, d), 7.32–7.56 (6H, m), 7.64 (1H, s), 7.71–7.87 (5H, m), 8.02 (1H, s), 8.22 (1H, d).

Step 4

3-((3-(2-(7-chloro-2-quinolinyl)ethenyl)phenyl)chloromethyl)-α,α-dimethylbenzenemethanol To a solution of the diol of Step 3 (508 mg, 1.182 mmol) in 16 mL of CH₂Cl₂:THF 1:1 at −40° C., Et₃N (250 μL, 1.80 mmol) and methanesulfonyl chloride (110 μL, 1.42 μmol) were added and the mixture was stirred at −40° C. for 30 min, then at 0° C. for 2 h and r.t. for 3 h. Aq 5% NaHCO₃ was added and the product was extracted with CH₂Cl₂, dried over Na₂SO₄ and evaporated to dryness to yield the title compound.

¹H NMR (CDCl₃): δ 1.57 (6H, s), 6.20 (1H, s), 7.25–7.52 (7H, m), 7.52–7.78 (6H, m), 8.10 (1H, s), 8.14 (1H, d).

Step 5

Ethyl 3-(acetylthio)-2-methylpropanoate

Ethyl 2-methylpropenoate (39 mmol) was diluted with 5.6 mL (78 mmol) of thiolacetic acid and stirred at 65° C. for 36 h. The mixture was then diluted with ether, washed with water and the organic phase was dried with Na₂SO₄. Evaporation to dryness yielded the title material as an orange oil which was used as such for the next step.

Step 6

Ethyl 3-mercapto-2-methylpropanoate

At −20° C., 3N NaOH (150 mL, 450 mmol) was added dropwise to a solution of ethyl 3-(acetylthio)- 2-methylpropanoate (66.47 g, 349 mmol, Step 5) in 700 mL of MeOH and the mixture was stirred at that temperature for 30 min. 25% Aq NH₄OAc was then added and the title thiol was extracted with EtOAc, dried over MgSO₄, concentrated and distilled to yield 42.52 g (82%) of the title compound as an oil; bp: 96°–98° C./15 mm Hg.

¹H NMR (CDCl₃): δ 1.21–1.36 (6H, m), 1.50 (1H, t, SH), 2.66 (2H, m), 2.81 (1H, m), 4.19 (2H, q).

Step 7

Ethyl 3-((1-(3-(2-(7-chloro-2-quinolinyl)ethenyl)phenyl)-1-(3-(2-hydroxy-2-propyl)phenyl)methyl)thio)- 2-methylpropanoate To the crude chloride of Step 4 dissolved in 10 mL of DMF, ethyl 3-mercapto-2-methylpropanoate (Step 6; 350 μl, approx. 2.4 mmol) and Cs₂CO₃ (1.61 g, 4.9 mmol) were added and the mixture was stirred at r.t. for 3.5 h. 25% Aq NH₄OAc was then added and the reaction mixture was extracted with EtOAc, dried over Na₂SO₄ and purified by flash chromatography on silica using EtOAc:toluene 7.5:92.5 and 10:90 to yield 347 mg of the title compound as an oil (52% yield for Steps 6 and 7).

¹H NMR (CDCl₃): δ 1.20 (3H, d), 1.25 (3H, t), 1.58 (6H, s), 1.96 (1H, s, OH), 2.47 (1H, m), 2.62 (1H, td), 2.74 (1H, m), 4.15 (2H, q), 5.23 (1H, s), 7.27–7.57 (8H, m), 7.57–7.79 (5H, m), 8.09 (1H, s), 8.12 (1H, d).

Step 8

A mixture of the ester of Step 7 (6.67 mmol) and 1.0 N NaOH (13 mL) in 55 mL of MeOH:THF 3:2 was stirred at r.t for 24 h. 25% Aq NH₄OAc was then added and the mixture was acidified with HOAc. The title acid was extracted with EtOAc, dried over Na₂SO₄ and purified by flash chromatography on silica with acetone:toluene:HOAc. Yield: 74%.

To this acid in 10 mL of EtOH was added 1.0 N NaOH (1.0 equiv.). The solvents were evaporated and the product was freeze-dried to give the title compound as a yellowish solid.

Anal. Calc'd for C₃₁H₂₉ClNO₃SNa●H₂O: C, 65.08; H, 5.46; N, 2.45. Found: C, 64.85; H, 5.09; N, 2.38.

EXAMPLE 12

2(S)-(((1(S)-(3-(2-(7-chloro-2-quinolinyl)ethenyl)phenyl)-4-(2-(2-hydroxy-2-propyl)phenyl)butyl)thio)methyl)butanoic acid Step 1

1-(3-(2-(7-chloro-2-quinolinyl)ethenyl)phenyl)- 3-buten-1-ol

Using the procedure of Example 80, Step 1, but substituting allylmagnesium bromide for vinylmagnesium bromide, the title alcohol was obtained.

¹H NMR (CD₃COCD₃): δ 2.52 (2H, t), 4.36 (1H, d), 4.78 (1H, m) 4.95–5.15 (2H, m), 5.75–6.00 (1H, m), 7.30–7.65 (5H, m) 7.70–8.10 (5H, m), 8.32 (1H, d).

Step 2

2-(2-(2-iodophenyl)-2-propoxy)tetrahydropyran

To a solution of methyl 2-iodobenzoate (7.33 g, 28 mmol) in toluene (70 mL) at −20° C. was added dropwise 1.5M MeMgBr (56 mL, 3 equiv.). When the addition was complete, the ice bath was removed and the mixture was stirred for a further hour. It was quenched with aq NH₄Cl at 0° C. Extraction with EtOAc and evaporation of the solvent gave an oil which was purified by flash chromatography using EtOAc/hexane (1:20 and 1:15) to afford 2-iodo-α,α-dimethylbenzenemethanol (2.40 g) which was used as such. To a solution of this tertiary alcohol (2.40 g, 9.16 mmol) in CH₂Cl₂ (20 mL) containing 3,4-dihydro-2H-pyran (4.17 mL, 5 equiv.) at 0° C. was added triphenylphosphine hydrobromide (313 mg, 0.1 equiv.) and the mixture was stirred at r.t. for 0.5 hour. Aq. 25% NH₄OAc was then added and the title product was extracted with CH₂Cl₂, dried over Na₂SO₄ and purified by flash chromatography on silica using EtOAc:hexane 1:20 to give 2.69 g of an oil.

¹H NMR (CD₃COCD₃): δ 1.4–2.0 (6H, m), 1.72 (3H, s), 1.79 (3H, s), 3.38 (1H, m), 3.90 (1H, m), 4.58 (1H, m), 6.98 (1H, dt), 7.38 (1H, dt), 7.58 (1H, dd), 8.03 (1H, dd).

Step 3

1-(3-(2-(7-chloro-2-quinolinyl)ethenyl)phenyl)- 4-(2-(2-(2-tetrahydropyranyloxy)- 2-propyl)phenyl)-1-butanone Using the procedure of Example 80, Step 2, the iodide of Step 2 (2.69 g, 7.78 mmol) was coupled with the homoallylic alcohol of Step 1 (2.11 g, 7.0 mmol) at 100° C. for 4 hours to afford 1.50 g of the title compound and 1.04 g of 2-(2-(4-(3-(2-(7-chloro- 2-quinolinyl)ethenyl)phenyl)-4-oxobutyl)phenyl)-2-propanol, which can be converted to the title product using the procedure of Step 2.

¹H NMR (CD₃COCD₃): δ 1.35–1.85 (6H, m), 1.53 (3H, s), 1.72 (3H, s) 2.12 (2H, m), 2.99 (1H, m), 3.19–3.40 (4H, m), 3.88 (1H, s) 4.50 (1H, m), 7.05–8.40 (15H, m).

Step 4

1(R)-(3-(2-(7-chloro-2-quinolinyl)ethenyl)phenyl)- 4-(2-(2-(2-tetrahydropyranyloxy)-2-propyl)phenyl)- 1-butanol Using the procedure of Example 16, Step 4, the ketone of Step 3 was reduced to the title (R)-alcohol.

$^1$H NMR (CD$_3$COCD$_3$): δ 1.35–2.00 (10H, m), 1.55 (3H, s), 1.68 (3H, s), 2.80–3.40 (3H, m), 3.85 (1H, m), 4.44 (1H, m), 4.80 (1H, m), 7.00–8.05 (14H, m), 8.34 (1H, d).

Step 5

Using the procedures of Example 15, Step 7, the mesylate of the alcohol of Step 4 was prepared.

To a solution of the thiol of Example 32, Step 10 (144 mg, 1.1 mmol) in DMSO (1 mL) in a water bath was added 97% NaH (56 mg, 2.26 mmol). After 15 minutes, a solution of the above mesylate (523 mg, 0.82 mmol) in DMSO (2 mL) was added dropwise. After stirring for 1 hour, the reaction mixture was quenched at 0° C. with 25% aq. NH$_4$OAc. Acidification with HOAc, extraction with EtOAc, drying over Na$_2$SO$_4$ and flash chromatography of the residue on silica using EtOAc:hexane:HOAc 20:80:1 gave the crude thioether.

Finally, the tetrahydropyranyl ether was hydrolyzed as in Example 15, Step 10, to give the title acid.

$^1$H NMR (CD$_3$COCD$_3$): δ 0.82 (3H, t), 1.40–1.85 (4H, m), 1.55 (6H, s), 2.00 (2H, m), 2.38–2.65 (3H, m), 3.00 (2H, t), 4.06 (1H, t), 7.08 (3H, m), 7.35–7.69 (6H, m), 7.70–8.05 (5H, m) 8.35 (1H, d).

EXAMPLE 15

Sodium 3-((1-(3-(2-(7-chloro-2-quinolinyl)ethenyl)phenyl)-3-(2-(2-hydroxy-2-propyl)phenyl)propyl)thio)- 2-methylpropanoate

Step 1

3-bromobenzenemethanol

3-Bromobenzaldehyde (157 mmol) was dissolved in 300 mL of THF. At 0° C., 800 mL of EtOH was added, followed by NaBH$_4$ (5.93 g, 157 mmol). The mixture was then stirred at r.t. (room temperature) for 1 hour and poured into cold 25% aq. (aqueous) NH$_4$OAc. The organic solvents were evaporated and the residue was extracted with toluene:THF 1:1, dried over Na$_2$SO$_4$ and filtered through silica to yield the title compound.

Step 2

2-((3-bromophenyl)methoxy)tetrahydropyran

The alcohol of Step 1 (41.23 mmol), dihydropyran (12.5 mL, 137 mmol) and triphenylphosphine hydrobromide (725 mg, 2.11 mmol) were mixed together in 200 mL of CH$_2$Cl$_2$ and stirred for 2 days. The solvent was then evaporated and the title product was purified by flash chromatography on silica using EtOAc:toluene.

Step 3

3,4-dihydro-1-naphthalenyl acetate

A mixture of α-tetralone (200 mL, 1.5 mol) and conc. H$_2$SO$_4$ (4 mL) in isopropenyl acetate (1.0 L, 9.08 mol) was heated to reflux overnight. It was cooled to r.t. and filtered through a mixture of celite, NaHCO$_3$ and silica (approx. 1:1:0.2) with EtOAc and concentrated to yield 317.1 g of the crude title product; bp: 90° C./0.5 mm Hg.

$^1$H NMR (CDCl$_3$): δ 2.30 (3H, s), 2.44 (2H, td), 2.87 (2H, t), 5.70 (1H, t), 7.10 (1H, m), 7.13–7.20 (3H, m).

Step 4

2-(3-oxopropyl)benzoic acid

At −50° C., 200 mL of MeOH were added to a solution of the enol acetate of Step 3 (214 g, approx. 1.04 mol) in 800 mL of acetone. At −78° C., ozone was bubbled through this solution for 7 h (or until the excess of O$_3$ produced a green color). The excess of O$_3$ was blown away by a stream of N$_2$ and a solution of triphenylphosphine (327 g, 1.25 mol) in 1 L of acetone was then added, slowly at −78° C. The temperature was slowly raised to −10° C. over 30 min., 1N HCl (700 mL) was slowly added, and the mixture was stirred at 3° C. for 16 h. The organic solvent were evaporated, 500 mL of EtOAc were added and the mixture was alkalinized with an excess of NaHCO$_3$ (approx. 270 g). The aqueous phase was washed with EtOAc (2×1 L) and the organic layers were reextracted with 1 L of saturated NaHCO$_3$ by agitation over 2 h. The combined aqueous extracts were then acidified with conc. HCl and extracted with EtOAc. The extract was dried over Na$_2$SO$_4$, the solvent was evaporated and the acetic acid was co-evaporated with toluene to yield 139.6 g of the title compound (75% for Steps 3 and 4) as a white solid.

$^1$H NMR (CDCl$_3$): δ 2.88 (2H, t), 3.36 (2H, t), 7.35 (2H, dd), 7.53 (1H, dd), 8.11 (1H, d), 9.86 (1H, s).

Step 5

2-(3-hydroxy-3-(3-((2-tetrahydropyranyloxy)methyl)phenyl)propyl)benzoic acid

At −10° C., a solution of the aldehyde of Step 4 (5.045 g, 28.3 mmol) in 50 mL of THF was added dropwise to 0.57M 3-((2-tetrahydropyranyloxy)methyl)phenylmagnesium bromide in THF (120 mL, 68.4 mmol, prepared from the bromide of Step 2 and Mg in THF and filtered to remove the excess of Mg) and the mixture was stirred at r.t. for 30 min. At 0° C., 25% aq NH$_4$OAc was added. The title product was extracted with EtOAc, dried over Na$_2$SO$_4$ and purified by flash chromatography on silica using acetone:toluene:HOAc 5:95:1 and 15:85:1.

$^1$H NMR (CD$_3$COCD$_3$): δ 1.41–1.86 (8H, m), 1.93–2.08 (2H, m), 3.11 (2H, m), 3.45 (1H, m), 3.83 (1H, m), 4.45 (1H, d), 4.66 (2H, m), 7.10–7.53 (7H, m), 7.91 (1H, d).

Step 6

3-(2-acetylphenyl)-1-(3-((2-tetrahydropyranyloxy)methyl)phenyl)propanol

At 0° C., 1.5M MeLi (7.5 mL, 11.25 mmol) was added dropwise to a solution of the hydroxyacid of Step 5 (2.65 mmol) in 30 mL of THF and the mixture was stirred at 0° C. for an hour. At 0° C., freshly distilled TMSCl (chlorotrimethylsilane, 2.8 mL, 22.1 mmol) was added and the mixture was stirred at r.t. for an hour. At 0° C., 25% aq. NH$_4$OAc was then added and the solution was stirred at r.t. for 1.5 h. The title product was extracted with EtOAc, dried over Na$_2$SO$_4$ and purified by flash chromatography on silica.

Step 7

Ethyl 3-((3-(2-acetylphenyl)-1-(3-((2-tetrahydropyranyloxy)methyl)phenyl)propyl)thio)- 2-methylpropanoate At −40° C., Et$_3$N (triethylamine) (1.60 mL, 11.5 mmol) and methanesulfonyl chloride (750 μl, 9.69 mmol) were added to a solution of the alcohol of Step 6 (7.39 mmol) in 74 mL of CH$_2$Cl$_2$ and the mixture was stirred at −40° C. for an hour and at −10° C. for 45 minutes. Saturated aq NaHCO$_3$ was then added and the mesylate was extracted with CH$_2$Cl$_2$, dried over Na$_2$SO$_4$ and concentrated. To this mesylate in 150 mL of anhydrous CH$_3$CN, ethyl 3-mercapto-2-methylpropanoate (Example 4, Step 6; 2.20 mL, approx. 15 mmol) and Cs$_2$CO$_3$ (7.57 g, 23.2 mmol) were added and the mixture was stirred under a stream of N$_2$ for 2 hours. 25% Aq NH$_4$OAc was then added and the title product was extracted with EtOAc, dried over Na$_2$SO$_4$ and purified by flash chromatography on silica with EtOAc:toluene.

Step 8

3-((3-(2-acetylphenyl)-1-(3-((2-tetrahydropyranyloxy)methyl)phenyl)propyl)thio)- 2-methylpropanoic acid A mixture of the ester of Step 7 (6.67 mmol) and 1.0N NaOH (13 mL) in 55 mL of MeOH:THF 3:2 was stirred at r.t. for 24 hours. 25% Aq NH$_4$OAc was then added and the mixture was acidified with HOAc. The title acid was extracted with EtOAc, dried over Na$_2$SO$_4$ and purified by flash chromatography on silica with acetone:toluene:HOAc.

Step 9

Methyl 3-((3-(2-(2-hydroxy-2-propyl)-phenyl- 1-(3-((2-tetrahydropyranyloxy)methyl)phenyl)propyl)thio)- 2-methylpropanoate To a well stirred solution of the methyl ketone of Step 8 (5.39 mmol) in 100 mL of anhydrous toluene, 1.5M MeMgBr (9.0 mL, 13.5 mmol) was added dropwise at −10° C. and the suspension was stirred at 0° C. for 30 minutes. Saturated aq NH$_4$Cl was then added and the product was extracted with EtOAc, dried over Na$_2$SO$_4$ and purified by flash chromatography on silica using acetone:toluene:HOAc 4:96:1. The impure acid was dissolved in Et$_2$O and diazomethane was added at 0° C. When the reaction was completed, HOAc was added, followed by 25% aq NH$_4$OAc. The title ester was extracted with EtOAc, washed with 5% aq NaHCO$_3$, dried over Na$_2$SO$_4$ and purified by flash chromatography on silica.

Step 10

Methyl 3-((3-(2-(2-hydroxy-2-propyl)phenyl)- 1-(3-hydroxymethyl)phenyl)propyl)thio)-2-methylpropanoate A mixture of the ester of Step 9 (5.019 mmol) and pyridinium p-toluenesulfonate (500 mg, 1.99 mmol) in 30 mL of MeOH was stirred at r.t. for 16 hours and then evaporated to dryness. Flash chromatography of the residue on silica afforded the title compound.

Step 11

Methyl 3-((1-(3-formylphenyl)-3-(2-(2-hydroxy- 2-propyl)phenyl)propyl)thio)-2-methylpropanoate To a solution of the benzylic alcohol of Step 10 (6.20 mmol) in EtOAc (120 mL) was added protionwise activated MnO$_2$ (10.15 g, 114 mmol) and the reaction was followed by TLC. When the reaction was completed (approximately 2 hours), the mixture was filtered through silica, concentrated, and the title product was purified by flash chromatography on silica.

$^1$H NMR (CD$_3$COCD$_3$): δ 1.11 (3H, 2d), 1.58 (6H, s), 2.25 (2H, m), 2.45 (1H, m), 2.61 (2H, m), 2.90 (1H, m), 3.16 (1H, m), 3.61 and 3.65 (3H, 2s), 4.00 (1H, 2s), 4.15 (1H, 2t), 7.13 (3H, m), 7.41 (1H, d), 7.60 (1H, t), 7.93 (2H, m), 8.00 (1H, s), 10.10 (1H, s).

Step 12

Methyl 3-((1-(3-(2-(7-chloro-2-quinolinyl)ethenyl)phenyl)-3-(2-(2-hydroxy-2-propyl)phenyl)propyl)thio)- 2-methylpropanoate To ((7-chloro-2-quinolinyl)methyl)triphenylphosphonium bromide (525 mg, 1.01 mmol, U.S. Pat. No. 4,851,409, Example 4, Step 2) in a THF (2 mL) solution at −78° C. was added dropwise 1.6M nBuLi (472 mL, 0.945 mmol). After a few minutes, the aldehyde of Step 11 (140 mg, 0.338 mmol) was then added and the resulting mixture was stirred at −78° C. for 30 min. The reaction mixture was then allowed to warm to r.t. for 30 min and was quenched by the addition of 25% aq NH$_4$OAc. The title product was then extracted with EtOAc, dried on Na$_2$SO$_4$ and evaporated under reduced pressure. After purification by flash chromatography (20% EtOAc in toluene), the title compound was obtained as an oil (170 mg, 89%).

$^1$H NMR (CD$_3$COCD$_3$): δ 1.10 (3H, 2d), 1.53 (6H, s), 2.25 (2H, m), 2.41 (1H, m), 2.66 (2H, m), 2.90 (1H, m), 3.16 (1H, m), 3.58 and 3.60 (3H, 2s), 4.02 (1H, 2s), 4.08 (1H, m), 7.08 (3H, m), 7.33–7.55 (5H, m), 7.61 (1H, m), 7.75–8.00 (5H, m), 8.28 (1H, d).

Step 13

Using the procedure of Example 4, Step 8, the ester of Step 12 was hydrolyzed to the title sodium salt.

Anal. calcd for C$_{33}$H$_{33}$ClNO$_3$SNa●2H$_2$O: C, 64.12; H, 6.03; N, 2.27. Found: C, 64.02; H, 5.91; N, 2.34.

EXAMPLE 16

Sodium 3-((1-(S)-(3-(2-(7-chloro-2-quinolinyl)ethenyl)phenyl)- 3-(2-(2-hydroxy-2-propyl)phenyl)propyl)thio)- 2-(S)-methylpropanoate Step 1

1-(3-(2-(7-chloro-2-quinolinyl)ethenyl)phenyl)ethanone

To 3-(2-(7-chloro-2-quinolinyl)ethenyl)benzaldehyde, MeMgBr was added (in THF at 0° C.) to give an ethanol derivative, which was oxidized to the title compound as in Example 15, Step 11.

$^1$H NMR (CD$_3$COCD$_3$): δ 2.68 (3H, s), 7.55–7.68 (3H, m), 7.89–8.05 (6H, m), 8.36 (2H, m).

Step 2

Methyl 2-(iodomethyl)benzoate

The title compound was prepared according to Example 32, Step 1.

Step 3

Methyl 2-(3-(3-(2-(7-chloro-2-quinolinyl)ethenyl)phenyl)-3-oxopropyl)benzoate

To a suspension of the ketone (10.0 g, 32.6 mmol) of Step 1 and the iodide (2.7 g, 47.7 mmol) of Step 2 in THF was added 1,3-dimethyl-3,4,5,6-tetrahydro- 2(1H)-pyrimidinone (4 mL). The ketone was dissolved by heating and the resulting solution was cooled to −60° C. A solution of 0.35M lithium diisopropylamide (89.7 mL, 30.9 mmol) was then added dropwise. After the addition was completed, the dry ice bath was removed and the reaction was allowed to warm to +10° C. The reaction was quenched by the addition of 25% aq. NH$_4$OAc and the desired product was extracted with EtOAc, dried over Na$_2$SO$_4$ and evaporated under reduced pressure. The resulting mixture was purified by flash chromatography (toluene to 5% EtOAc in toluene) to yield 8 g (55%) of the title product.

$^1$H NMR (CD$_3$COCD$_3$): δ 3.40 (4H, m), 3.87 (3H, s), 7.35 (1H, t), 7.40–7.65 (5H, m), 7.80–8.05 (7H, m), 8.30 (1H, d), 8.39 (1H, s).

Step 4

Methyl 2-(3-(3-(2-(7-chloro-2-quinolinyl) ethenyl)phenyl)-3(R)-3-hydroxypropyl)benzoate At −20° C., (S)-tetrahydro-1-methyl-3,3-diphenyl-1H,3H-pyrrolo(1,2-c)(1,3,2)oxazaborole (J. Am. Chem. Soc., 104, 5551–5553 (1987) 3.82 g, 0.014 mol) was added to a solution of the ketone of Step 3 (30.0 g, 66 mmol) in THF (556 mL). To this mixture, 1.0M BH$_3$●THF (111 mL) was slowly added within 10 minutes. After 15 minutes, the reaction was quenched with 2M HCl (250 mL). After extraction with EtOAc, the organic phase was washed with 25% aq NH$_4$OAc followed by saturated NaCl. The solvent was removed at reduced pressure to afford an oil which was purified by flash chromatography to give the title compound.

Step 5

α,α-dimethyl-2-(3-(3-(2-(7-chloro-2-quinolinyl)ethenyl)phenyl)- 3(R)-3-hydroxypropyl)benzenemethanol At 0° C., 3.0M MeMgCl (90 mL, 270 mmol) was slowly added to a solution of the ester of Step 4 (61 mmol) in 350 mL of toluene and the mixture was stirred at 0° C. for 30 minutes. At 0° C., 25% aq NH$_4$OAc was added and the title product was extracted with EtOAc, dried over Na$_2$SO$_4$ and purified by flash chromatography on silica.

Step 6

2-(3-(3-(2-(7-chloro-2-quinolinyl)ethenyl)phenyl)- 3(R)-3-(diphenyl(2-methyl-2-propyl)siloxy)propyl)-α,α-dimethyl-benzenemethanol A mixture of the diol of Step 5 (24.37 g, 52.75 mmol), Et$_3$N (22.0 mL, 158 mmol), 4-(dimethylamino)pyridine (10.96 g, 89.7 mmol) and t-butylchlorodiphenylsilane (28.0 mL, 108 mmol) in 260 mL of CH$_2$Cl$_2$ was stirred at r.t. for 18 hours and at reflux for 4 hours. At 0° C., 25% aq NH$_4$OAc was added and the phases were separated. The aqueous phase was extracted with EtOAc and the combined organic layers were dried over Na$_2$SO$_4$ and concentrated. The residue was purified twice by flash chromatography on silica with EtOAc;toluene 2.5:97.5 and 5:95 to yield 28.92 g (79%) of the title silyl ether.

Step 7

7-chloro-2-(2-(3-(3-(2-(2-tetrahydropyranyloxy)- 2-propyl)phenyl)-1-(R)-diphenyl(2-methyl- 2-propyl)siloxy)propyl)phenyl)ethenyl) quinoline The tertiary alcohol of Step 6 (28.88 g, 41.23 mmol), dihydropyran (12.5 mL, 137 mmol) and triphenylphosphine hydrobromide (725 mg, 2.11 mmol) were mixed together in 200 mL of CH$_2$Cl$_2$ and stirred for 2 days. The solvent was then evaporated and the title product was purified by a flash chromatography on silica using toluene and EtOAc;toluene 1.5:98.5 and 2.5:97.5. Yield: 29.90 g, 92%.

Step 8

1-(R)-(3-(2-(7-chloro-2-quinolinyl)ethenyl)phenyl)- 3-(2-(2-(2-tetrahydropyranyloxy)-2-propyl)phenyl)propanol To a solution of the silyl ether of Step 7 (29.89 g, 38.11 mmol) in 130 mL of anhydrous THF, a 1.0M solution of Bu$_4$NF in THF (100 mL) was added and the resulting solution was kept at 8° C. for 15 hours and then stirred at r.t. for 2 hours. At 0° C., 25% aq NH$_4$OAc was added and the title alcohol was extracted with EtOAc, dried over Na$_2$SO$_4$ and purified by flash chromatography on silica with EtOAc:toluene 10:90, 15:85 and 20:80.

Step 9

3-((1-(S)-(3-(2-(7-chloro-2-quinolinyl)ethenyl)phenyl)-3-(2-(2-(2-tetrahydropyranyloxy)- 2-propyl)phenyl)propyl)thio)-2-(S)-methylpropanoic acid The mesylate of the alcohol of Step 8 (1.58 mmol) was prepared using the procedure of Example 15, Step 7. To a solution of this crude mesylate and 2(S)-3-mercapto-2-methylpropanoic acid (3.35 mmol, prepared from commercially available 3-(acetylthio)-2-(S)-methylpropanoic acid as in Example 4, Step 6) in 15 mL of anhydrous DMF at 0° C. was added 60% NaH in oil (530 mg, 13.3 mmol) and the mixture was stirred at r.t. for 2 hours. 25% Aq NH$_4$OAc was then added and the solution was acidified with AcOH and extracted with EtOAc:THF 1:1. The organic layers were dried over Na$_2$SO$_4$ and evaporated. Flash chromatography of the residue on silica afforded the title compound.

Step 10

A mixture of the acid of Step 10 (3.254 g, 5.019 mmol) and pyridinium p-toluenesulfonate (500 mg, 1.99 mmol) in 30 mL of MeOH was stirred at r.t. for 16 hours and then evaporated to dryness. Flash chromatography of the residue on silica with EtOAc:hexane:HOAc 25:75:1 and 30:70:1 afforded 2.453 g (87%) of the tertiary alcohol. The title sodium salt was then formed as in Example 4, Step 8.

[α]$_D$=−86.0° (c 1.00, THF) Anal. calcd for C$_{33}$H$_{33}$ClNO$_3$SNa●2H$_2$O: C, 64.12; H, 6.03; N, 2.27. Found: C, 63.90; H, 5.73; N, 2.17.

EXAMPLE 17

Sodium 3-((1-(R)-(3-(2-(7-chloro-2-quinolinyl)ethenyl)phenyl)- 3-(2-(2-hydroxy-2-propyl)phenyl)propyl)thio)- 2-(S)-methylpropanoate Step 1

1-(S)-(3-(2-(7-chloro-2-quinolinyl)ethenylphenyl)- 3-(2-(2-(2-tetrahydropyranyloxy)- 2-propyl)phenyl)propanol At 0° C., diethyl azodicarboxylate (7.6 mL, 48.3 mmol) was added dropwise to a solution of the alcohol of Example 16, Step 8 (17.47 g, 31.97 mmol), triphenylphosphine (12.60 g, 48.04 mmol) and R-(−)-α-methoxyphenylacetic acid (8.07 g, 48.6 mmol) in 320 mL of anhydrous THF. The mixture was stirred at 0° C. for 30 minutes and the solvents were evaporated. Flash chromatography of the residue on silica using EtOAc:toluene 2.5:97.5, 5:95 and 7.5:92.5 afforded 21.84 g (98%) of the inverted alcohol as the mandelate ester. This ester was hydrolyzed to the title alcohol as in Example 4, Step 8.

Step 2

Using the procedure of Example 16, Steps 9–10, the benzylic alcohol of Step 1 was converted to the title sodium salt.

[α]$_D$=+116.6° (c 1.08, THF) Anal. calcd for C$_{33}$H$_{33}$ClNO$_3$SNa●2H$_2$O: C, 66.04; H, 5.88; N, 2.33. Found: C, 65.74; H, 5.84; N, 2.22.

EXAMPLE 18

Sodium 3-((1(S)-(3-(2-(7-chloro-2-quinolinyl)ethenyl)phenyl)- 1-((3-hydroxy-3-methylbutyl)thio)methyl)thio)propanoate Anal. Calc'd for $C_{26}H_{27}ClNO_3S_2Na \bullet 1.5H_2O$: C, 56.67; H, 5.49; N, 2.54. Found: C, 56.97; H, 5.48; N, 2.55.

EXAMPLE 27

3-((1-(3-(2-(7-chloro-2-quinolinyl)ethenyl)phenyl)-3-(2-(2-hydroxy-2-propyl)phenyl)propyl)thio)-2-ethylpropanoic acid mp: 124°–6° C. Anal. Calc'd for $C_{34}H_{36}ClNO_3S$: C, 71.12; H, 6.32; N, 2.44. Found: C, 71.10; H, 6.75; N, 2.42.

EXAMPLE 28

3-((1-(3-(2-(7-chloro-2-quinolinyl)ethenyl)phenyl)-3-(2-(2-hydroxy-2-propyl)phenyl)propyl)thio)-2-methoxypropanoic acid $^1$H NMR ($CD_3COCD_3$): δ 1.55 (6H, s), 2.15–2.35 (2H, m), 2.65–2.95 (3H, m), 3.10–3.25 (1H, m), 3.35 (3H, d), 3.80–3.95 (1H, m), 4.20 (1H, t), 7.05–7.20 (3H, m), 7.35–7.70 (6H, m), 7.80–8.00 (5H, m), 8.30 (1H, d).

EXAMPLE 29

Sodium 3-((1(S)-(3-(2-(7-chloro-2-quinolinyl)ethenyl)phenyl)- 3-(2-(2-hydroxy-2-propyl)phenyl)propyl)thio)- 2(R)-ethylpropanoate Anal. Calc'd for $C_{34}H_{35}ClNO_3SNa \bullet 2H_2O$:
C, 64.60; H, 6.17; N, 2.21. Found: C, 64.76; H, 6.01; N, 2.14.

EXAMPLE 31

Sodium 3-((1(S)-(3-(2-(7-chloro-2-quinolinyl)ethenyl)phenyl)- 3-(2-(2-hydroxy-2-propyl)phenyl)propyl)thio)- 2(R)-methylpropanoate Anal. Calc'd for $C_{33}H_{33}ClNO_3SNa \bullet 2H_2O$: C, 64.18; H, 5.99; N, 2.26. Found: C, 63.84; H, 6.09; N, 2.31.

EXAMPLE 32

3-((1-(S)-(3-(2-(7-chloro-2-quinolinyl)ethenyl)phenyl)- 3-(2-(2-hydroxy-2-propyl)phenyl)propyl)thio)- 2-(S)-ethylpropanoic acid

Step 1

Methyl 2-(iodomethyl)benzoate

Following the procedure in Tetrahedron, 22, 2107 (1966), phthalide was converted to 2-(bromomethyl)benzoic acid using HBr in HOAc. The methyl ester was prepared by treatment with oxalyl chloride and methanol.

A mixture of NaI (180 g) and methyl 2-(bromomethyl)benzoate (82.44 g, 360 mmol) in acetone (500 mL) was stirred at r.t. for 2 h. The acetone was evaporated and the product was redissolved in EtOAc. It was washed with 25% aq $NH_4OAc$ followed by 10% aq $NaHCO_3$, a sodium bisulfite solution and brine. Evaporation to dryness afforded 100 g (100% yield) of the title iodide.

$^1$H NMR ($CDCl_3$): δ 3.95 (3H, s), 4.93 (2H, s), 7.32 (1H, m), 7.43 (2H, m), 7.94 (1H, d).

Step 2

1-(3-2-(7-Chloro-2-quinolinyl)ethenyl)phenyl)ethanone

To 3-(2-(7-chloro-2-quinolinyl)ethenyl)benzaldehyde (U.S. Pat. No. 4,851,409, Jul. 25, 1989, Example 24, Step 1), MeMgBr was added (in THF at 0° C.) to give an ethanol derivative, which was oxidized to the title compound as in Example 15, Step 11.

$^1$H NMR ($CD_3COCD_3$): δ 2.68 (3H, s), 7.55–7.68 (3H, m), 7.89–8.05 (6H, m), 8.36 (2H, m).

Step 3

Methyl 3-(3-(2-(7-chloro-2-quinolinyl)ethenyl)phenyl)-3-oxopropanoate

In a 500 mL flask fitted with a condenser were suspended the ketone of Step 2 (57.05 g, 185 mmol) and dimethylcarbonate (13.70 mL, 2.5 equiv.) in THF (230 mL). 80% NaH (16.70 g, 3 equiv.) was added portionwise over a few minutes and the reaction was initiated through the addition of MeOH (370 µl). The mixture was stirred at r.t. The solids gradually dissolved and when the evolution of hydrogen has subsided, the mixture was heated at 70° C. for 1 h. After cooling to r.t., it was poured onto cold 25% aq $NH_4OAc$. The solid was collected and air dried and swished in EtOH (600 mL) containing EtOAc (50 mL) for 18 h. The title compound was collected as a pale beige solid (60.3 g, 89% yield).

$^1$H NMR ($CD_3COCD_3$): δ 3.70 (s, 3H); 3.73 (small peak, $OCH_3$ of enol form); 7.45–7.70 (m, 6H); 7.80–8.10 (m, 3H), 8.36 (d, 2H).

Step 4

Methyl 2-(3-(3-(2-(7-chloro-2-quinolinyl)ethenyl)phenyl)-3-oxopropyl)benzoate

To a solution of the β-ketoester of Step 3 (50.0 g, 0.136 mol) and the iodide of Step 1 (41.5 g, 1.1 equiv.) in DMF at 0° C. was added 80% NaH (4.51 g, 1.1 equiv.). The ice bath was removed and the mixture was stirred at r.t. After 2 h, when no starting material remained, the reaction mixture was poured onto cold 25% aq $NH_4OAc$. The solid collected was swished in EtOH (60 mL) overnight to afford 60.0 g of the pure adduct (97%).

The above material was suspended in HOAc/conc. HCl mixture (1.2 L/240 mL) and heated at 90° C. for 4 h. After it was cooled to r.t., it was poured onto cold aq $NH_4Cl$. The solid was collected and air dried.

The above mixture (containing the title ester and its acid) was suspended in acetone (500 mL) containing MeI (4.25 mL) and powdered $K_2CO_3$ (18 g). The mixture was heated at 50° C. for 3 h until the methylation was complete. The reaction mixture was partitioned between EtOAc and $H_2O$. The aqueous phase was extracted with EtOAc (×2) and the combined organic phase was washed with brine, dried and concentrated. The resulting residue was recrystallized from EtOAc:hexane 1:1 to afford 37.7 g (53% yield) of the title compound.

Step 5

4-(S)-(1-Methylethyl)-2-oxazolidinone

The title compound was prepared according to Evans, Mathre and Scott (J. Org. Chem., 50, 1830 (1985)) from (S)-(+)-2-amino-3-methyl-1-butanol and diethyl carbonate in the presence of $K_2CO_3$.

Step 6

3-(1-oxobutyl)-4-(S)-(1-methylethyl)-2-oxazolidinone

A mechanically stirred, cooled (−78° C.) solution of the oxazolidinone of Step 5 (32.3 g, 250 mmol) in anhydrous THF (830 mL) was metalated with 163 mL (1.6M in hexane, 261 mmol) of n-BuLi and treated with freshly distilled butanoyl chloride (28.1 mL, 271 mmol). The reaction mixture was warmed to 0° C. and stirred for 0.5 h. Excess acid chloride was hydrolyzed by the addition of 1M aqueous $K_2CO_3$ (165 mL) followed by stirring the resultant two-phase mixture for 1 h at r.t. Volatiles were removed in vacuo and the product was extracted into $CH_2Cl_2$ (3×). The combined organic extracts were successively washed with $H_2O$ and brine, dried over $MgSO_4$ and concentrated to give the title compound as a pale yellow oil (52.1 g, quantative). A portion of this crude product was purified by flash chromatography on silica with EtOAc:hexane 1:4 to give a colorless liquid.

$^1H$ NMR ($CDCl_3$): δ 6.88 (3H, d), 0.92 (3H, d), 0.99 (3H, t), 1.70 (2H, m), 2.38 (1H, m), 2.77–3.04 (2H, m), 4.18–4.31 (2H, m), 4.44 (1H, m).

Step 7

3-(1-Oxo-2-(S)-(((phenylmethyl)thio)methyl)butyl)- 4-(S)-(1-methylethyl)-2-oxazolidinone A solution of the N-acylated product of Step 6 (36.9 g, 185 mmol) in anhydrous THF (70 mL) was added to a magnetically stirred, cooled (−78° C.) solution of LDA (lithium diisopropylamide) (prepared from 28.6 mL (20.6 g, 204 mmol) of diisopropylamine and 127.5 mL (1.6M in hexane, 204 mmol) of n-butyllithium) in anhydrous THF (240 mL). After stirring for 0.5 h at −78° C. the resultant lithium enolate was treated with benzyl bromomethyl sulfide (52.3 g, 241 mmol) for 2 h at −20° C. The reaction was quenched by the addition of half-saturated aq $NH_4Cl$ (200 mL). Volatiles were removed in vacuo and the product was extracted into $CH_2Cl_2$ (3×). The combined organic extracts were successively washed with 1M aqueous sodium bisulfate (2×), 1M aqueous $KHCO_3$ (2×) and brine, dried over $MgSO_4$ and concentrated in vacuo to give 76.5 g of a yellow liquid. This crude material was roughly purified by flash chromatography on silica with EtOAc: hexane 1:99, 2:98, 5:95, 10:90 and 15:85 to give the title compound as a colorless liquid (48.9 g), which was used as such for the next step.

Step 8

Benzyl 2-(S)-(((Phenylmethyl)thio)methyl)butanoate

To a magnetically stirred, cooled (−10° C.) solution of lithium benzyloxide in anhydrous THF (400 mL), prepared from freshly distilled benzyl alcohol (28.7 mL, 30.0 g, 277 mmol) and 127.5 mL (1.6M in hexane, 204 mmol) of n-BuLi, was added a solution of the product of step 7 (48.9 g, approx. 146 mmol) in anhydrous THF (170 mL) over a 0.5 h period. After 15 min. at −10° C., the reaction mixture was warmed to 0° C., stirred for 2 h and then quenched by the addition of half-saturated aq $NH_4Cl$ (300 mL). Volatiles were removed in vacuo and the product was extracted into $CH_2Cl_2$(3×). The combined organic extracts were successively washed with $H_2O$ (3×) and brine, dried over $MgSO_4$ and concentrated in vacuo to give 74 g of a pale yellow oil. This crude material was purified in two portions by flash chromatography on silica with toluene giving the title compound as a colorless liquid (32.8 g), containing a small amount of butanoic acid benzyl ester and an unidentified impurity. This product was used as such for the next step.

$^1H$ NMR ($CDCl_3$): δ 0.87 (3H, t), 1.63 (2H, m), 2.48–2.61 (2H, m), 2.64–2.76 (1H, m), 3.68 (2H, s), 5.16 (2H, s), 7.28 (5H, br s), 7.37 (5H, br s).

Step 9

2-(S)-(((Phenylmethyl)thio)methyl)butanoic acid

Glacial HOAc (120 ml) was added to a suspension of the product of step 8 (32.4 g, approx. 103 mmol) in 210 ml of 30–32% anhydrous HBr in glacial HOAc (approx. 1.03 mol) to complete the dissolution. The resulting solution was stirred at 70° C. for 6h and at 50° C. overnight. The reaction mixture was then cooled to r.t., diluted with $H_2O$ (750 mL) and extracted with $CH_2Cl_2$ (7×). The combined organic extracts were concentrated in vacuo. The residue was diluted with toluene (500 mL) and concentrated in vacuo 5 times to remove HOAc. The residue was dissolved in 1M aq KOH (750 mL), washed with $CH_2Cl_2$ (4×), acidified to pH 1 with concentrated HCl and extracted with $CH_2Cl_2$ (6×). The combined organic extracts were dried over $Na_2SO_4$ and concentrated in vacuo to afford 17.6 g of the title compound as a pale yellow liquid which was used as such for the next step.

$^1H$ NMR ($CDCl_3$): δ 0.91 (3H, t), 1.66 (2H, m), 2.44–2.56 (2H, m), 2.65–2.75 (1H, m), 3.73 (2H, s), 7.31 (5H, br s).

Step 10

2-(S)-(mercaptomethyl)butanoic acid

A solution of the carboxylic acid of Step 9 (17.4 g, 77.6 mmol) in dry THF (30 mL) was added to approx. 200 mL of ammonia (condensed in the flask from the cylinder) at −78° C. The solution was warmed to −50° C. and sodium (5.2 g, 226 mmol) was added in small portions over a 0.5 h period. After the reaction mixture had remained dark-blue for 0.5 h, the reaction was quenched by the addition of $NH_4Cl$ (10 g). Ammonia was evaporated under a stream of nitrogen and the THF was removed in vacuo. The residue was dissolved in 1M aq KOH (400 mL), and washed with $Et_2O$ (3×). The aqueous-solution was cooled to 0° C. and acidified to pH 1 with concentrated HCl, and the product was extracted into $Et_2O$ (4×). The organic extracts were dried over $Na_2SO_4$ and concentrated in vacuo to afford 11.0 g of the crude product which was distilled under reduced pressure (short Vigreux column) to give the title product as a colorless liquid which solidified upon cooling (8.43 g, 81%); bp: 102°–104° C./approx. 2 mmHg.

$[\alpha]_D$=−20.3° (c 1.96, $CHCl_3$). $^1H$ NMR ($CDCl_3$): δ 0.98 (3H, t), 1.54 (1H, t), 1.64–1.82 (2H, m), 2.50–2.87 (3H, m).

Step 11

Using the procedure of Example 16, Steps 4–10, but replacing 3-mercapto-2-(S)-methylpropanoic acid by 2-(S)-(mercaptomethyl)butanoic acid (the thiol of Step 10), the title product, mp 115°–7° C., was obtained from the ketoester of Step 4.

$[\alpha]_D$ of the acid =−115° (c 2.00, $CHCl_3$) Anal. calcd for $C_{34}H_{36}ClNO_3S$: C, 71.12; H, 6.32; N, 2.44. Found: C, 70.69; H, 6.58; N, 2.38.

EXAMPLE 33

3-((1-(3-(2-(7-chloro-2-quinolinyl)ethenyl)phenyl)-3-(2-(2-hydroxy-2-propyl)phenyl)propyl)thio)-2,2-dimethylpropanoic acid mp: 123°–6° C. Anal. Calc'd for $C_{34}H_{36}ClNO_3S$: C, 71.12; H, 6.32; N, 2.44. Found: C, 71.24; H, 6.64; N, 2.29.

EXAMPLE 34

Sodium 3-((1-(3-(2-(7-chloro-2-quinolinyl)ethenyl)phenyl)-3-(3-(2-hydroxy-2-propyl)phenyl)propyl)thio)- 2-ethylpropanoate Anal. Calc'd for $C_{34}H_{35}ClNO_3SNa \bullet H_2O$: C, 66.49; H, 6.07; N, 2.28. Found: C, 66.69; H, 5.64; N, 1.98.

EXAMPLE 35

Sodium 3-((1-(3-(2-(7-chloro-2-quinolinyl)ethenyl)phenyl)-3-(2-(1,1,1,3,3,3-hexafluoro-2-hydroxy-2-propyl)phenyl)propyl)thio)- 2-ethylpropanoate Anal. Calc'd for $C_{34}H_{29}ClNO_3SF_6Na \bullet 2H_2O$: C, 55.18; H, 4.49; N, 1.89; F, 15.40. Found: C, 55.07; H, 4.03; N, 1.85; F, 14.75.

EXAMPLE 60

Sodium 3-((1(R)-(3-(2-(7-chloro-2-quinolinyl)ethenyl)phenyl)- 3-(2-(2-hydroxy-2-propyl)phenyl)propyl)thio)- 2(S)-ethylpropanoate $[\alpha]_D$ (free acid)=+85.6° (c 1.64, $CHCl_3$). Anal. Calc'd for $C_{34}H_{35}ClNO_3SNa \bullet 1.8H_2O$: C, 64.97; H, 6.19; N, 2.23. Found: C, 64.97; H, 5.84; N, 2.24.

EXAMPLE 61

Sodium 3-((1-(3-(2-(7-chloro-2-quinolinyl)ethenyl)phenyl)-3-(2-(2-hydroxy-2-methylpropyl)phenyl)propyl)thio)propanoate Anal. Calc'd for $C_{33}H_{33}ClNO_3SNa \bullet 2H_2O$: C, 64.12; H, 6.03; N, 2.27. Found: C, 64.38; H, 6.14; N, 2.12.

EXAMPLE 63

2-(((1-(3-(2-(7-chloro-2-quinolinyl)ethenyl)phenyl)- 3-(2-(2-hydroxy-2-propyl)phenyl)propyl)thio)methyl)pentanoic acid mp: 127°–130° C.

EXAMPLE 73

Sodium 2(S)-(((1(S)-(3-(2-(7-chloro-2-quinolinyl)ethenyl)phenyl)- 3-(2-(2-hydroxy-2-methylpropyl)phenyl)propyl)thio)methyl)butanoate

Step 1

1-(2-iodophenyl)-2-methyl-2-propanol

A 100 mL round bottom flask was charged with methyl 2-iodophenylacetate (2.6 g, 9.4 mmol), THF (10 mL) and toluene (30 mL) and kept under an argon atmosphere. This solution was cooled to −10° C. and a solution of methyl magnesium bromide (14.4 mL of 1.5 M in THF/toluene (1:3)) was added dropwise over 15 minutes. The reaction was allowed to proceed at r.t. for 3 hours. The reaction was stopped by addition of 25% aq. $NH_4OAc$ (100 mL) and the product was extracted with EtOAc (2×100 mL). The combined organic layers were dried over $MgSO_4$ and concentrated under reduced pressure. The resulting residue was purified by flash chromatography, eluted with EtOAc/hexane 15% v/v to give 1.38 g (53%) of the title compound as a colorless oil.

$^1H$ NMR ($CD_3COCD_3$): δ 1.20 (6H, s), 2.95 (2H, s), 3.40 (1H, s, OH), 6.90 (1H, dt), 7.30 (1H, dt), 7.50 (1H, dd), 7.80 ppm (1H, dd).

Step 2

1-(2-(3-(3-(2-(7-chloro-2-quinolinyl)ethenyl)phenyl)-3-oxopropyl)phenyl)-2-methyl- 2-propanol Using the procedure of Example 80, Step 2, but replacing methyl 2-(2-iodophenyl)propanoate by 1-(2-iodophenyl)-2-methyl- 2-propanol (Step 1), the title compound was prepared.

$^1H$ NMR ($CDCl_3$): δ 1.30 (6H, s), 2.90 (2H, s), 3.20 (2H, t), 3.35 (2H, t), 7.17–7.30 (4H, m), 7.38–7.55 (3H, m), 7.65 (1H, d), 7.70–7.85 (3H, m), 7.93 (1H, d), 8.08–8.18 (2H, m), 8.25 (1H, s).

Step 3

1-(3-(2-(7-chloro-2-quinolinyl)ethenyl)phenyl)- 3-(2-(2-(2-tetrahydropyranyloxy)-2-methylpropyl)phenyl)- 1-propanone A solution of the alcohol of Step 2 (390 g, 8.29 mmol), 3,4-dihydro-2H-pyran (7.4 mL, 81 mmol) and pyridinum p-toluenesulfonate (684 mg, 2.7 mmol) in 44 mL of $CH_2Cl_2$ was heated at reflux for 23 hours. The reaction mixture was allowed to cool to r.t. and 10% aq. $NaHCO_3$ was added. The title product was extracted with $CH_2Cl_2$, dried over $Na_2SO_4$ and purified by flash chromatography on silica using EtOAc:toluene 5:95. Yield: 4.22 g, 92%.

Step 4

Using the procedure of Example 16, Step 4, the ketone of Step 3 was reduced to the (R)-alcohol. The mesylate was then formed as in Example 15, Step 7, and was substituted by the thiol of Example 32, Step 10 using the procedure of Example 12, Step 5. Finally, the tetrahydropyranyl ether was hydrolyzed as in Example 15, Step 10, and the sodium salt of the acid was prepared as in Example 4, Step 8.

Anal. calcd for $C_{35}H_{37}ClNO_3SNa \bullet 4H_2O$: C, 61.62; H, 6.65; N, 2.05. Found: C, 61.46; H, 6.60; N, 2.09.

EXAMPLE 78

2-(3-(3-(2-(7-chloro-2-quinolinyl)ethenyl)phenyl)-3-((3-hydroxy-3-methyl)butyl)thio)propyl)benzoic acid Anal. Calc'd for $C_{32}H_{32}ClNO_3S$: C, 70.38; H, 5.91; N, 2.56. Found: C, 70.17; H, 5.96; N, 2.38.

EXAMPLE 80

2-(2-(3(S)-(3-(2-(7-chloro-2-quinolinyl)ethenyl)phenyl)-3-((3-hydroxy-3-methylbutyl)thio)propyl)phenyl)propanoic acid

Step 1

1-(3-(2-(7-chloro-2-quinolinyl)ethenyl)phenyl)- 2-propen-1-ol

To a degassed suspension of 3-(2-(7-chloro-2-quinolinyl)ethenyl)benzaldehyde (U.S. Pat. 4,851,409, Example 24, Step 1) (100 g, 0.34 mol) in toluene (700 mL) at 0° C. was slowly added 1.0M vinylmagnesium bromide in toluene/THF (370 mL, 0.37 mol). After stirring for 1 hour at 0° C., the reaction was quenched by the slow addition of saturated $NH_4Cl$ solution (150 ml), followed by $H_2O$ (500 mL) and HOAc (50 mL). The product was extracted with EtOAc and the two-phase system was filtered through celite to remove an insoluble precipitate. The aqueous phase was then re-extracted with EtOAc (100 mL) and the combined organic layer was washed with $H_2O$, followed by brine. The solution was dried ($MgSO_4$), and evaporated to give a dark yellow residue which was purified by flash chromatography (EtOAc:hexane 1:5, then 1:3). The product was filtered from the column fractions to give a beige solid (67.6 g, mp=110°–112° C.). The filtrate was concentrated and the resulting residue was recrystallized from EtOAc/hexane 1:4 to give a second crop of 15.1 g.

Step 2

Methyl 2-(2-(3-(3-(2-(7-chloro-2-quinolinyl)ethenyl)phenyl)- 3-oxopropyl)phenyl)propanoate A degassed suspension of the product of Step 1 (15.0 g, 46.6 mmol), n-$Bu_4$NCl (25.9 g, 93 mmol), LiOAc•$H_2O$ (7.7 g, 115 mmol), LiCl (1.98 g, 93 mmol), Pd(OAc)$_2$ (0.315 g, 1.4 mmol), and methyl 2-(2-iodophenyl)propanoate in DMF (90 mL) was stirred for 2 hours at 100° C. The dark red solution was then cooled to 0° C. and poured into saturated $NaHCO_3$ solution (500 mL). The product was extracted with EtOAc and the organic layer was washed with $H_2O$ followed by brine. The solvent was removed under vacuum and the residue was purified by flash chromatography (EtOAc:hexane 1:10, 1:5 and 3:10) to give a pale yellow foam (18.9 g).

$^1$H NMR (CD$_3$COCD$_3$): δ 1.46 (3H, d, J=7.0 Hz), 3.10–3.20 (2H, m), 3.43–3.53 (2H, m), 3.62 (3H, s), 4.17 (1H, q, J=7.0 Hz), 7.17–7.38 (4H, m), 7.51–7.64 (3H, m), 7.85 (1H, d, J=8.6 Hz), 7.92–8.08 (5H, m), 8.31–8.40 (2H, m).

Step 3

Methyl 2-(2-(3(R)-(3-(2-(7-chloro-2-quinolinyl)ethenyl)phenyl)- 3-hydroxypropyl)phenyl)propanoate Using the procedure of Example 16, Step 4, the ketone of Step 2 was reduced to the title compound.

Step 4

4-Mercapto-2-methyl-2-butanol

To a solution of methyl 3-mercaptopropanoate (20.0 g, 166 mmol) in dry toluene (100 mL) at 0° C. was added slowly a solution of 1.5M MeMgBr in toluene/THF (388 mL, 583 mmol). The reaction mixture was then stirred at r.t. for 3 hours. After cooling to 0° C., the reaction was carefully quenched by the addition of saturated $NH_4Cl$ solution (100 mL), followed by $H_2O$ (100 mL). The resulting salts were dissolved by careful addition of 2M HCl, and the product was extracted with EtOAc. The organic layer was washed with $H_2O$ and brine. The solvent was removed under vacuum and the residue was distilled to give the title compound as a colorless oil (10.1 g, bp=85°–93° C., ~0.2 mm Hg).

Step 5

Methyl 2-(2-(3(S)-(3-(2-(7-chloro-2-quinolinyl)ethenyl)phenyl)- 3-((3-hydroxy-3-methylbutyl)thio)propyl)phenyl)propanoate Using the procedure of Example 15, Step 7, the mesylate of the alcohol of Step 3 (0.65 g, 1.3 mmol) was prepared. The crude mesylate so obtained was suspended in dry $CH_3CN$ (7 mL) with $Cs_2CO_3$ (1.3 g, 4.0 mmol). The suspension was cooled to 0° C. and 4-mercapto-2-methyl-2-butanol (Step 4) (0.32 g, 2.7 mmol) was added. The reaction mixture was stirred for 2 hours at 0° C., followed by 1 hour at r.t. The suspension was then filtered and the filtrate was concentrated at 20° C. The residue was dissolved in EtOAc and the organic layer was washed with 1M NaOH followed by $H_2O$ and brine. The solvent was removed under vacuum and the residue was purifed by flash chromatography (EtOAc:hexane 1:10 and 1:5) to give the title compound as a pale yellow syrup (~0.7 g).

Step 6

The ester of Step 5 (approx. 0.7 g, approx. 1.3 mmol) was hydrolyzed using the procedure of Example 4, Step 8 to give the title compound as a pale yellow foam (0.32 g).

Anal. calcd for $C_{34}H_{36}O_3SNCl$: C, 71.12; H, 6.32; N, 2.44. Found C, 71.41; H, 6.47; N, 2.25.

EXAMPLE 86

4-((1(S)-(3-(2-(7-chloro-2-quinolinyl)ethenyl)phenyl)- 3-(2-(2-hydroxy-2-propyl)phenyl)propyl)thio)butanoic acid This compound was prepared according to the procedure of Example 87, using ethyl 4-mercaptobutanoate (Chem. Abstr. 58 P11490c) instead of 2-methyl-4-mercaptobutanoate.

EXAMPLE 87

4-((1(S)-(3-(2-(7-chloro-2-quinolinyl)ethenyl)phenyl)- 3-(2-(2-hydroxy-2-propyl)phenyl)propyl)thio)-2-methylbutanoic acid This compound was prepared according to the procedure of Example 131, but using methyl 2-methyl-4-mercapto butanoate (Helv. Chim. Acta 1980, 63, 2508) instead of the thiol therein.

EXAMPLE 89

3-((1(S)-(3-(2-(7-chloro-2-quinolinyl)ethenyl)phenyl)- 3-(2-(2-hydroxy-2-propyl)phenyl)propyl)thio)-2-(methoxymethyl)propanoic acid This compound was prepared from the mesylate of Example 146, step 7, and methyl 3-mercapto-2-(methoxymethyl)propanoate, using Method K. The thiol was obtained from 2-(bromomethyl)propenoic acid by first Fisher esterification with methanol, followed by triphenylmethyl mercaptan addition. Sodium methoxide in methanol/THF for 10 days afforded the second Michael addition product. Deprotection of the thiol with $I_2$ in MeOH/ether afforded the disulfide, which was reduced with $Ph_3P$ to give the free thiol.

EXAMPLE 90

2-(3(S)-(3-(2-(7-chloro-2-quinolinyl)ethenyl)phenyl)- 3-((3-hydroxy,-3-methylbutyl)thio)propyl)benzoic acid The title compound was prepared from the alcohol of Example 16, Step 4, and the thiol of Example 80, Step 4, using Method K.

EXAMPLE 91

2-(3(R)-(3-(2-(7-chloro-2-quinolinyl)ethenyl)phenyl)- 3-((3-hydroxy-3-methylbutyl)thio)propyl)benzoic acid The title compound was prepared according to the procedure of Example 90, but using the enantiomeric catalyst as in Example 16, Step 4.

EXAMPLE 92

3-((1-(S)-(3-(2-(7-chloro-2-quinolinyl)ethenyl)phenyl)-3-(3-(2-hydroxy-2-propyl)phenyl)propyl)thio)- 2(S)-ethylpropanoic acid From methyl 3-iodobenzoate, the alcohol from Example 80, Step 1, and the thiol from Example 32, Step 10, this compound was prepared by Method K, using the silylation-THP-desilylation protection sequence of Method G.

EXAMPLE 94

2-(4(S)-(3-(2-(7-chloro-2-quinolinyl)ethenyl)phenyl)-4-((3-hydroxy-3-methylbutyl)thio)butyl)benzoic acid The title compound was prepared from the alcohol of Example 12, Step 1 and the thiol of Example 80, Step 4, using Method K.

EXAMPLE 97

2-(3(S)-(3-(2-(7-chloro-2-quinolinyl)ethenyl)phenyl)-3-((3-hydroxy-3-methylbutyl)thio)propyl)-5-chlorobenzoic acid The title compound was prepared from the ketoester of Example 32, Step 3 and methyl 5-chloro-2-(iodomethyl)benzoate, using Method F. This iodide was obtained as described in Example 32, Step 1, but using 6-chlorophthalide (E.P. 399,818, Nov. 28, 1990) instead of phthalide.

EXAMPLE 102

2-(3(S)-(3-(2-(7-chloro-2-quinolinyl)ethenyl)phenyl)-3-((4-hydroxy-4-methylpentyl)thio)propyl)benzoic acid The title compound was obtained using the procedure of Example 90, but using the thiol from Example 138, Step 7.

EXAMPLE 103

3-((1-(S)-(3-(2-(7-chloro-2-quinolinyl)ethenyl)phenyl)-3-(4-(2-hydroxy-2-propyl)phenyl)propyl)thio)- 2(S)-ethylpropanoic acid This compound was prepared from methyl-4-bromobenzoate by first treating it with methylmagnesium bromide to get the tertiary alcohol. The alcohol was then protected as a tetrahydropyranyl ether. Metalation followed by iodine quench gave the corresponding iodide, which was transformed into the title compound by Method K using the thiol of Example 32, Step 10.

EXAMPLE 105

2-(2-(3(S)-(3-(2-(7-chloro-2-quinolinyl)ethenyl)phenyl)-3-((4-hydroxy-4-methylpentyl)thio)propyl)phenyl)propanoic acid 2-(2-Iodophenyl)propanoic acid was prepared as described in Example 138, Step 1, but replacing the iodoethane with iodomethane. This was then assembled using Method K, with the alcohol from Example 80, Step 1, and the thiol from Example 138, Step 7 to yield the title compound.

EXAMPLE 106

N-methanesulfonyl 2-(2-(3(S)-(3-(2-(7-chloro-2-quinolinyl)ethenyl)phenyl) 3-((4-hydroxy-4-methylpentyl)thio)propyl)phenyl)propanamide The product from Example 105 was treated with methanesulfonamide and 1-(3-dimethylaminopropyl)- 3-ethyl carbodiimide hydrochloride to give the title compound.

EXAMPLE 112

2-(3(S)-(3-(2-(7-chloro-2-quinolinyl)ethenyl)phenyl)-3-((4-hydroxy-4-methylpentyl)thio)propyl)-5-chlorobenzoic acid This compound was prepared according to the procedure of Example 97, but using the thiol from Example 138, Step 7.

EXAMPLE 114

2-(2-(3(S)-(3-(2-(7-chloro-2-quinolinyl)ethenyl)phenyl)-3-((4-hydroxy-4-methylpentyl)thio)propyl)phenyl)- 2-methylpropanoic acid 2-(2-iodophenyl)acetic acid was first esterified with 2-(trimethylsilyl)ethanol. Double alkylation (LDA/MeI) gave 2-(trimethylsilyl)ethyl 2-(2-iodophenyl)-2-methylpropanoate. This was then coupled to the alcohol from Example 80, Step 1, using Method K. The thiol was that of Example 138, Step 7.

EXAMPLE 118

3-((1(R)-(3-(2-(7-chloro-2-quinolinyl)ethenyl)phenyl)-3-(2-(2-hydroxy-2-propyl)phenyl)propyl)thio)butanoic acid The title compound was prepared according to Method K, using the mesylate from Example 146, Step 7. The thiol was obtained from addition of thiolacetic acid on methyl crotonate, followed by $K_2CO_3$/MeOH hydrolysis of the resulting thiol ester.

EXAMPLE 122

3-((1(R)-(3-(2-(7-chloro-2-quinolinyl)ethenyl)phenyl)-3-(2-(2-hydroxy-2-propyl)phenyl)propyl)thio)-2-methylbutanoic acid The title compound was prepared according to Method K, using the mesylate from Example 146, Step 7. The thiol was prepared by reaction of tiglic acid with benzyl mercaptan and piperidine, followed by Na/$NH_3$ debenzylation.

EXAMPLE 126

2-(2-(3(S)-(3-(2-(7-chloro-2-quinolinyl)ethenyl)phenyl)-3-((4-hydroxy-pentyl)thio)propyl)phenyl)propanoic acid This compound was prepared using the procedure of Example 105 up to the mesylate, which was then coupled with 5-mercapto-2-pentanone. The ketone was reduced using $NaBH_4$, and the methyl ester was hydrolyzed.

EXAMPLE 127

3(S)-((1(R)-(3-(2-(7-chloro-2-quinolinyl)ethenyl)phenyl)-3-(2-(2-hydroxy-2-propyl)phenyl)propyl)thio)butanoic acid The title compound was prepared according to Method K, using the mesylate of Example 146, Step 7, and methyl 3(S)-mercaptobutanoate. This thiol was obtained by hydrazine deprotection of the thiolester described below.

Methyl 3(S)-(acetylthio)butanoate

To a −23° C. solution of $PPh_3$ (40 mmol, 10.48 g) in THF (100 mL) was added diethyl azodicarboxylate (40 mmol, 6.28 mL) dropwise and the mixture was stirred at −23° C. for 16 hours, during which time a white precipitate was obtained. A THF (30 mL) solution of methyl 3(R)-hydroxybutanoate (20 mm, 2.36 g) and thiolacetic acid (20 mmol, 2.85 mL) was slowly added and the mixture was allowed to slowly warm to 25° C. and was stirred 16 h at 25° C. Most THF was removed in vacuo and EtOAc (10 mL) and hexanes (100 mL) were added. Insolubles were removed by filtration and the residue was purified by chromatography on silica gel to afford the title compound.

$[\alpha]_D^{25} = -21°$ (c=3, CHCl$_3$). $^1$H NMR (acetone d$_6$) δ 1.30 (3H, d), 2.25 (3H, s), 2.45–2.80 (2H, m), 3.62 (3H, s), 3.75–3.95 (1H, m).

EXAMPLE 128

3(R)-((1(R)-(3-(2-(7-chloro-2-quinolinyl)ethenyl)phenyl)-3-(2-(2-hydroxy-2-propyl)phenyl)propyl)thio)butanoic acid The title compound was prepared according to Method K, using the mesylate of Example 146, Step 7, and methyl 3(R)-mercapto butanoate. This thiol was obtained by hydrazine deprotection of the thiolester described below.

Methyl 3(R)-acetylthiobutanoate

The title compound was prepared from methyl 3(S)-hydroxybutyrate in a manner identical to the one described for the (S)-isomer in Example 127.

$[\alpha]_D^{25} = +20.7°$ (c=3, CHCl$_3$)

EXAMPLE 129

3-(S)-((1(R)-(3-(2-(7-chloro-2-quinolinyl)ethenyl)phenyl)-3-(2-(2-hydroxy-2-propyl)phenyl)propyl)thio)-2-(S)-methylbutanoic acid This compound was prepared according to the procedure of Example 127, but the methyl 3-(R)-hydroxybutanoate was first alkylated with methyl iodide as described by Keck et al., (J. Org. Chem., 1985, 4317) to give methyl 3-(R)-hydroxy-2-(S)-methylbutanoate. The latter was transformed into the thiol according to the procedure of Example 127.

$^1$H NMR (acetone-d$_6$) δ 1.10 (d, 3H), 1.33 (d, 3H), 1.50 (s, 6H), 2.15–2.30 (m, 2H), 2.43 (quintet, 1H), 2.75–2.90 (m, 2H), 3.15 (m, 1H), 4.13 (t, 1H), 7.05–7.28 (m, 3H), 7.35–7.65 (m, 6H), 7.80–8.05 (m, 5H), 8.35 (d, 1H).

EXAMPLE 130

3-(R)-(((1(R)-(3-(2-7-chloro-2-quinolinyl)ethenyl)phenyl)-3-(2-(2-hydroxy-2-propyl)phenyl)propyl)thio)- 2-(R)-methylbutanoic acid The title compound was prepared according to the procedure of Example 129, but using methyl 3-(S)-hydroxy-2-(S)-methylbutanoate.

EXAMPLE 131

3-((1-(R)-(3-(2-(7-chloro-2-quinolinyl)ethenyl)phenyl)-3-(2-(2-hydroxy-2-propyl)phenyl)propyl)thio)pentanoic acid The title compound was prepared according to Method K using the mesylate of Example 146, Step 7. The thiol was obtained by treatment of 2-pentenoic acid with benzyl mercaptan and piperidine, followed by sodium in ammonia debenzylation.

EXAMPLE 134

3-((1(R )-(3-(2-(7-chloro-2-quinolinyl)ethenyl)phenyl)-3-(2-(2-hydroxy-2-propyl)phenyl)propyl)thio)- 3-methylbutanoic acid

Step 1

3-benzylthio-3-methylbutanoic acid

A solution of 3,3-dimethylacrylic acid (7 g, 70 mmol) and benzyl mercaptan (8.9 mL, 7.5 mmol) in piperidine (70 mL) was heated to reflux for 2 days. Piperidine was then evaporated and the product was partitioned between EtOAc and an aqueous solution of 1N HCl. The organic phases were washed with brine and dried over MgSO$_4$. After evaporation of the solvent the product was distilled with a Kugelrohr apparatus under high vacuum (1 mmHg) to give 15.5 g with 99% yield.

$^1$H NMR (CDCl$_3$) δ 1.50 (6H, s), 2.67 (2H, s), 3.82 (2H, s), 7.30 (5H, m).

Step 2

3-mercapto-3-methylbutanoic acid

Approximately 300 mL of ammonia was condensed in a three neck flask maintained at −70° C. Then, 8.3 g of sodium metal (0.35 mol) was added in small pieces and with very vigorous stirring. The 3-benzylthio-3-methylbutanoic acid from Step 1 (15.5 g, 69 mmol) dissolved in THF (50 mL) was added dropwise at −78° C. The deep blue solution was stirred for 1 h at −78° C. and solid NH$_4$Cl and an aqueous solution thereof were added until the blue color vanished. The solution was then warmed to r.t. and NH$_3$ was evaporated with a stream of nitrogen. The reaction mixture was then acidified with HOAc, extracted with EtOAc, washed with brine and dried over MgSO$_4$. The solvent was evaporated and the residual oil was used without further purification.

$^1$H NMR (CDCl$_3$) δ 1.50 (6H, s), 2.38 (1H, s) and 2.72 (2H, s).

Step 3

3-((1(R)-(3-(2-(7-chloro-2-quinolinyl)ethenyl)phenyl)-3-(2-(2-hydroxy-2-propyl)phenyl)propyl)thio)- 3-methylbutanoic acid A solution of the thiol of Step 2 (4.1 mmol, 560 mg) in DMSO (5 mL) was degassed using a stream of argon bubbling through the solution for 10 min and then cooled to 5° C. before adding oil-free NaH (11 mmol, 280 mg) portionwise. The resulting suspension was stirred for 10 min and a solution of the mesylate (2.7 mmol, 1.7 g) from Example 146, Step 7 in a mixture of DMSO:THF 1:2 (5 mL) was added. The solution was stirred at r.t. for 1 h and then poured into an aqueous solution of NH$_4$Cl in ice. The solution was acidified with HOAc and extracted with EtOAc. The combined organic phases were washed twice with water and brine, dried over MgSO$_4$ and the solvent was evaporated. The residue oil was purified by flash chromatography using 5:1 toluene:EtOAc with 2% acetic acid yielding 1.1 g (60%) of the title compound.

$^1$H NMR (CDCl$_3$) δ 1.32 and 1.38 (6H, two s), 1.47 (6H, br s), 1.70 (6H, m), 2.15 (2H, m), 2.50 (2H, AB system), 2.68, 2.93, 3.10 and 3.40 (2H, four dt), 3.33 (1H, m), 3.90 (1H, m), 4.08 (1H, br t), 4.33 (1H, m), 7.08 to 7.55 (9H, m), 7.68 (3H, m), 7.75 (1H, m), and 8.10 (2H, m).

Step 4

To a solution of the tetrahydropyranyl ether from Step 3 (1.1 g, 1.64 mmol) in MeOH (8 mL) were added pyridinium p-toluenesulfonate (85 mg, 0.33 mmol) and the solution was stirred for 5 days at r.t. The MeOH was evaporated, H$_2$O was added, and the aqueous layer was extracted twice using EtOAc with 2% HOAc. The combined organic layers were washed with brine and dried over Na$_2$SO$_4$. After evaporation of the solvent, the residual oil was purified by flash chromatography using 7:1 toluene:EtOAc with 2% HOAc to yield the title compound.

¹H NMR (CDCl₃) δ 1.32 and 1.42 (6H, two s), 1.58 (6H, two s), 2.17 (2H, m), 2.52 (2H, AB system), 2.80 (1H, dt), 3.18 (1H, dt), 4.08 (1H, t), 4.50 (1H, m), 7.05 to 7.52 (9H, m), 7.60 (4H, m), 8.10 (2H, m).

EXAMPLE 135

4-((1(R)-(3-(2-(7-chloro-2-quinolinyl)ethenyl)phenyl)-3-(2-(2-hydroxy-2-propyl)phenyl)propyl)thio)-3-methylbutanoic acid The title compound was prepared according to Method K, using the mesylate from Example 146, Step 7. The thiol was prepared from ethyl 3-mercapto-2-methyl propanoate by first protecting the thiol with a benzyl group. The ester was then removed with LiOH in THF/H₂O. Reaction with oxalyl chloride, followed by diazomethane provided the diazoketone which was rearranged with silver benzoate in MeOH. Saponification and Na/NH₃ debenzylation gave the thiol.

EXAMPLE 138

2(R)-(2-(3(S)-(3-(2-(7-chloro-2-quinolinyl)ethenyl)phenyl)-3-((4-hydroxy-4-methylpentyl)thio)propyl)phenyl)butanoic acid

Step 1

2-(2-iodophenyl)butanoic acid

To a solution of diisopropylamine (5.6 mL, 40 mmol) in dry THF (60 mL) at −10° C. was added 1.6M BuLi (25 mL, 40 mmol). After 30 min, a solution of 2-iodophenylacetic acid (5.24 g, 20 mmol) in THF (20 mL) was slowly added. The solution was stirred for 1 h, at which point iodoethane (1.6 mL, 117 mmol) was added. After 2 h at r.t. the reaction was quenched with 0.5M NH₄OAc solution and 6M HCl (10 mL) and the product was extracted with EtOAc. The organic layer was dried (MgSO₄) and evaporated to give an oily residue which was purified by flash chromatography (15:85 EtOAc:hexane containing 5% AcOH) to give 4.37 g of the title compound as an off-white solid.

Step 2

2-(Trimethylsilyl)ethyl 2-(2-iodophenyl)butanoate

To a solution of the acid of Step 1 (103 g, 0.356 mol), pyridine (58 mL, 0.717 mol) and 2-(trimethylsilyl)ethanol (61.2 mL, 0.427 mol) in CH₃CN (270 mL) was added a solution of dicyclohexylcarbodiimide (73.4 g, 0.356 mol) in CH₃CN (100 mL). The reaction mixture was stirred at r.t. for 2 h, at which point 5M oxalic acid in DMF solution (11 mL) was added. After stirring for 30 min, the suspension was filtered and the filtrate was diluted with EtOAc, washed with water and dried over MgSO₄. The crude product was distilled under reduced pressure to give 109 g of the title compound as a colorless oil (bp 120°–140° C./0.4 mm Hg).

Step 3

2-(trimethylsilyl)ethyl 2-(2-(3-(3-(2-(7-chloro- 2-quinolinyl)ethenyl)phenyl)-3-oxopropyl)phenyl)butanoate To a mixture of LiCl (3.26 g, 77 mmol), LiOAc (19.6 g, 192 mmol), n-Bu₄NCl (42.7 g, 154 mmol), Pd (OAc)₂ (0.52 g, 2.3 mmol) and the allyl alcohol of Example 80, Step 1 (24.7 g, 77 mmol) under N₂ was added a solution of the aryl iodide of Step 2 (30.0 g, 77 mmol) in DMF (150 mL). The suspension was degassed and purged with N₂, and was then stirred at 100° C. for 1 h. The dark red solution was then poured onto a mixture of ice (300 g) and saturated NaHCO₃ (300 mL). The red syrup was extracted with EtOAc. Following filtration through celite, the organic phase was washed with H₂O and saturated NaCl solution. After drying (MgSO₄), the solvent was removed under vacuum and the residue was purified by flash chromatography. Elution was effected with 1:20 EtOAc:hexane, followed by 1:10 EtOAc:hexane to give 37.4 g of the title compound as a white solid, mp 109°–111° C.

Step 4

2-(Trimethylsilyl)ethyl 2-(2-(3(R)-(3-(2-(7-chloro- 2-quinolinyl)ethenyl)phenyl)-3-hydroxypropyl)phenyl)butanoate The ketone of Step 3 (40 g, 68.5 mmol) was subjected to a chiral reduction as described in Example 16, Step 4 or as in Example 146, Step 2 (using (+)-B-chlorodiiospinocampheyl-borane) to give the title secondary alcohol as a pale yellow foam (35.3 g).

¹H NMR (CD₃COCD₃) δ −0.04 (9H, s), 0.80–0.94 (5H, m), 1.54–1.70 (1H, m), 1.93–2.24 (3H, m), 2.683.02 (2H, m), 3.68–3.77 (1H, m), 3.98–4.20 (2H, m), 4.52 (1H, d, J=4.5 Hz), 4.80–4.90 (1H, m), 7.10–7.30 (4H, m), 7.39–7.65 (5H, m), 7.77–8.03 (5H, m), 8.32 (1H, d, J=9.7 Hz).

Step 5

2-(Trimethylsilyl)ethyl 2(R)- and 2(S)-(2-( 3(R)-(3-(2-(7-chloro-2-quinolinyl)-ethenyl)phenyl)- 3-hydroxypropyl)phenyl)butanoate The mixture of diastereomers of Step 4 was separated by HPLC on a 50×30 mm μPorasil column with 1:150 2-propanol:hexane as solvent (flow rate 100 mL/min, UV detection λ=280 nm, retention time 40 and 47 min).

1ˢᵗ isomer (2(S)-) [α]_D =+78° C. (c=1, acetone)
2ⁿᵈ isomer (2(R)-) [α]_D =−24.5° C. (c=1.7, acetone)

Step 6

2-(Trimethylsilyl)ethyl 2(R)-(2-(3(R)-(3-( 2-(7-chloro-2-quinolinyl)ethenyl)phenyl)- 3-(methanesulfonyloxy)propyl)phenyl)butanoate To a solution of the 2ⁿᵈ isomer of Step 5 (4.0 g, 6.8 mmol) in CH₂Cl₂ (40 mL) at −10° C. was added Et₃N (2.9 mL, 20.5 mmol), followed by methanesulfonyl chloride (1.06 mL, 13.6 mmol). After 1 h at −10° C., saturated NaHCO₃ solution (10 mL) was added and the two-phase mixture was stirred rapidly for 15 min. The product was extracted with CH₂Cl₂ and the organic layer was washed with H₂O. The solution was then dried (MgSO₄), filtered, and evaporated to give the title compound as a pale yellow foam (4.4 g) which was used without purification in the following step.

Step 7

4-hydroxy-4-methyl-1-pentanethiol

To a mechanically stirred solution of methylmagnesium bromide (3M, 457 mL, 1.37 mol) in anhydrous Et₂O (800 mL) was slowly added a solution of δ-thiobutyrolactone (70 g, 0.685 mol) in Et₂O (500 mL). The internal temperature was maintained at approximately 30° C. The suspension was stirred overnight at r.t., at which point it was cooled at 0° C. and quenched with saturated NH₄Cl solution (1 L). The product was extracted with EtOAc and the organic layer was dried (MgSO₄) and evaporated to give an oil which was distilled (76° C./3 mm Hg) to give 58.9 g of crude product. Of this, 30 g was purified by flash chromatography (3:7 EtOAc:hexane) to give the title thiol as a colorless oil (29.5 g).

¹H NMR (CDCl₃) δ 1.24 (6H, s), 1.39 (1H, t, J=7.7 Hz), 1.52–1.63 (2H, m), 1.63–1.78 (2H, m), 2.52–2.62 (2H, m).

Step 8

2-(Trimethylsilyl)ethyl 2(R)-(2-(3(S)-( 3-(2-(7-chloro-2-quinolinyl)ethenyl)phenyl)- 3-((4-hydroxy-4-methylpentyl)thio)propyl)phenyl)butanoate A suspension of mesylate of Step 6 (4.4 g, 66 mmol) and $Cs_2CO_3$ (4.3 g, 132 mmol) in $CH_3CN$ (44 mL) was degassed and then purged with $N_2$. The suspension was then cooled to 0° C. and 4-hydroxy-4-methyl- 1-pentanethiol (Step 7, 1.8 mL, 132 mmol) was added. The reaction was stirred for 30 min at 0° C. followed by 3 h at r.t. Water (50 mL) was then added and the product was extracted with EtOAc. The organic layer was washed with $H_2O$ and saturated NaCl solution. The solvent was removed under vacuum and the crude product was purified by flash chromatography (1:20 and 1:10 EtOAc:toluene) to give the title compound as an off-white foam (4.25 g).

$^1H$ NMR ($CD_3COCD_3$) δ −0.03 (9H, s), 0.68–0.77 (3H, m), 0.92–0.99 (2H, m), 1.12 (6H, s), 1.35–1.70 (6H, m), 1.85–2.07 (1H, m), 2.07–2.26 (1H, m), 2.26–2.48 (2H, m), 2.56–2.70 (1H, m), 2.70–2.85 (1H, m), 3.52–3.61 (1H, m), 4.00–4.28 (3H, m), 7.12–7.33 (4H, m), 7.43–7.57 (4H, m), 7.62–7.69 (1H, m), 7.83–8.04 (5H, m), 8.34 (1H, d, J=9.7 Hz).

Step 9

To a solution of the ester of Step 8 (4.25 g, 60 mmol) in THF (43 mL) at r.t. was added the 1M $nBu_4NF$ solution (18 mL, 180 mmol). The solution was stirred at 50° C. for 1 h, and was then concentrated under vacuum to give a brown residue which was purified directly by flash chromatography. Elution was effected with 1:10 EtOAc:toluene containing 1% HOAc, followed by 1:5 EtOAc:toluene containing 1% HOAc to give the title compound as a yellow foam (3.6 g).

Anal. calcd for $C_{36}H_{40}ClNO_3S$: C, 71.80; H, 6.69; N, 2.33. Found: C, 72.11; H, 6.79; N, 2.03. $[α]_D$=−126 ° (c=1.47, acetone)

EXAMPLE 139

2(S)-(2-(3(S)-(3-(2-(7-chloro-2-quinolinyl)ethenyl)phenyl)-3-((4-hydroxy-4-methylpentyl)thio)propyl)phenyl)butanoic acid In the same manner as Example 138, Steps 6 to 9, the $1^{st}$ isomer of Example 138, Step 5 was converted to the title compound.

$[α]_D$=−43.6° (c=1.29, acetone). MS, m/e (relative intensity) 602 (M+1, 86), 468(62), 292(100), 229(45), 196(54).

EXAMPLE 140

2-(2-(3(S)-(3-(2-(7-chloro-2-quinolinyl)ethenyl)phenyl)-3-((4-hydroxy-4-methylpentyl)thio)propyl)-5-chlorophenyl)butanoic acid The title compound was prepared according to Example 138, except that the palladium catalyzed coupling was done using methyl 2-(2-bromo-5-chlorophenyl)butanoate. This bromide was obtained as described in Example 138, Step 1, using methyl 2-bromo-5-chlorophenyl acetate instead of 2-iodo phenylacetic acid, and a single equivalent of base.

EXAMPLE 146

Sodium 4-((1(R)-(3-(2-(7-chloro-2-quinolinyl)ethenyl)phenyl)- 3-(2-(2-hydroxy-2-propyl)phenyl)propyl)thio)- 3,3-dimethylbutanoate

Step 1

Methyl 2-(3-(3-(2-(7-chloro-2-quinolinyl)ethenyl)phenyl)-3-oxopropyl)benzoate

A degassed suspension of 1-(3-(2-(7-chloro- 2-quinolinyl)ethenyl)phenyl)-2-propen-1-ol (Example 80, Step 1, 50.30 g, 156 mmol), $LiOAc/2H_2O$ (41.2 g, 404 mmol), LiCl (6.84 g, 161 mmol), $Pd(OAc)_2$ (1.00 g, 4.45 mmol ) and methyl 2-bromobenzoate (33.5 g, 156 mmol) in 300 mL of DMF was stirred at 95° C. for 4 h. The mixture was cooled to r.t (room temperature) and added to 1.8 L of water. The product was extracted with hot EtOAc, dried over $Na_2SO_4$ and concentrated. It was dissolved in toluene and filtered through silica with toluene. Recrystallization in 1.2 L of EtOAc:hexanes 1:1 afforded 65.57 g of the title compound. Recrystallization of the mother liquors in 400 mL EtOAc:hexanes 1:3 afforded a further 8.30 g (86% overall yield) of the title material.

$^1H$ NMR identical to Example 32, Step 4.

Step 2

Methyl 2-(3(S)-(3-(2-(7-chloro-2-quinolinyl)ethenyl)phenyl)- 3-hydroxypropyl)benzoate To a solution of (−)-B-chlorodiisopinocampheylborane (72.2 g, 0.225 mol) in THF (300 mL) cooled at −25° C. was added dropwise a solution of the ketone of Step 1 (68.5 g, 0.15 mol) in THF (350 mL). The red orange solution was stirred overnight at 15° C. and then poured into ice-water while stirring. The precipitate formed was collected and washed two times with water and then EtOAc. The solid was partitioned between $CH_2Cl_2$ (2.5 L) and 6% diethanolamine in water (1.2 L). The organic phases were washed with brine and dried over $Na_2SO_4$. The solvent was evaporated and 700 mL of MeOH was added. The product was crystallized by adding 70 mL of water slowly with vigourous stirring. The solid was collected and washed with $MeOH:H_2O$, 10:1 to yield the title compound (44.7 g, 65%).

$^1H$ NMR ($CDCl_3$) δ 2.10 (2H, m), 3.12 (3H, m), 3.90 (3H, S), 4.75 (1H, t), 7.22 to 7.55 (8H, m), 7.67 (4H, m), 7.92 (1H, d), 8.10 (2H, m).

Step 3

2-(2-(3(S)-(3-(2-(7-chloro-2-quinolinyl)ethenyl)phenyl)-3-hydroxypropyl)phenyl)-2-propanol To a solution of the hydroxyester of Step 2 (38.68 g, 84.36 mmol) in 600 mL of toluene at 0° C. was added slowly 225 mL of 1.5M MeMgBr in toluene:THF 3:1 and the mixture was stirred at r.t. for 4 h. It was then poured into 2 L cold 12% $NH_4OAc$ and 25 mL of AcOH were added. The products were extracted in EtOAc, washed with brine, dried over $Na_2SO_4$ and concentrated. Flash chromatography of the residue with EtOAc:toluene 15:85 and 25:75 afforded first the methyl ketone derivative, then the title compound. Yield 24.06 g, 62%.

$^1H$ NMR ($CD_3COCD_3$) δ 1.59 (3H, s), 1.62 (3H, s), 2.11 (2H, m), 3.16 (2H, td), 4.15 (1H, s, OH), 4.52 (1H, d, OH), 4.81 (1H, m), 7.04–7.28 (3H, m), 7.37–7.57 (5H, m), 7.60 (1H, m), 7.78 (1H, s), 7.83–8.02 (4H, m), 8.32 (1H, d).

Step 4

2-(2-(3(S)-(3-(2-(7-chloro-2-quinolinyl)ethenyl)phenyl)-3-(dimethyl(2-methyl-2-propyl)silyloxy)propyl)phenyl)-2-propanol To the diol of Step 3 (36.56 g, 79.8 mmol) in 400 mL of $CH_2Cl_2$ was added tert-butyl-chlorodimethylsilane (18.21 g, 121 mmol), imidazole (10.97 g, 161 mmol) and 4-(dimethylamino)pyridine (0.988 g, 8.1 mmol) and the mixture was stirred at r.t. for 3 days. Toluene (400 mL) was then added and the product was filtered through silica with EtOAc:toluene 0:100 to 5:95. The title product was concentrated and stripped with toluene to remove any remaining silyl chloride.

Step 5

2-(2-(2-(3(S)-(3-(2-(7-chloro-2-quinolinyl)ethenyl)phenyl)- 3-(dimethyl(2-methyl-2-propyl)silyloxy)propyl)phenyl)- 2-propoxy)tetrahydropyran To a 0.2M solution of the tertiary alcohol of Step 4 in $CH_2Cl_2$ were added 5 equiv. of dihydropyran and 0.1 equiv. of triphenylphosphonium bromide and the mixture was stirred at reflux for 1 day. Then, the same amount of dihydropyran and triphenylphosphonium bromide were added and the mixture stirred at reflux another day. Toluene was added and the resulting solution was filtered through silica with EtOAc:toluene 0:100 to 2:98 to afford the title product.

Step 6

1-(S)-(3-(2-(7-chloro-2-quinolinyl)ethenyl)phenyl)- 3-(2-(2-((tetrahydropyran-2-yl)oxy)- 2-propyl)phenyl)-1-propanol 1.0M Tetrabutylammonium fluoride in THF (85 mL) was added slowly to a solution of the product of Step 5 (33.31 g, 47 mmol) in 250 mL of anhydrous THF at 0° C. and the mixture was left in a refrigerator overnight and at r.t. for 4 h. 25% Aq. $NH_4OAc$ was then added and the product was extracted in EtOAc, dried over $Na_2SO_4$ and purified by flash chromatography on silica with EtOAc:toluene 10:90 and 15:85, to afford the title product. Yield of Steps 4–6: 81%.

$^1H$ NMR, ($CD_3COCD_3$) δ 1.35–1.90 (12H, m), 2.10 (2H, m), 2.88–3.45 (3H, m), 3.88 (1H, m), 4.49 (2H, m, 10H), 4.90 (1H, m), 7.05–7.55 (8H, m), 7.61 (1H, br d), 7.80–8.04 (5H, m), 8.33 (1H, d).

Step 7

2-(2-(2-(3(S)-(3-(2-(7-chloro-2-quinolinyl)ethenyl)phenyl)- 3-(methanesulfonyloxy)propyl)phenyl)- 2-propoxy)tetrahydropyran To a 0.1M solution of the alcohol of Step 6 in $CH_2Cl_2$ at −40° C. was added 1.3 equiv. of methanesulfonyl chloride and 1.5 equiv. of $Et_3N$ and the mixture was stirred 30 min at −40° C. and 1 h at 0° C. Saturated $NaHCO_3$ was then added and the title mesylate was extracted in $CH_2Cl_2$, dried over $Na_2SO_4$, concentrated and stripped twice with toluene. The residual title compound was used for subsequent reactions without further purification.

Step 8

Methyl 3,3-dimethyl-4-hydroxybutanoate

To a suspension of LAH (lithium aluminum hydride) (4.9 g, 0.129 mol) in THF (300 mL) maintained at −78° C. was added during 45 min a solution of 2,2-dimethylsuccinic anhydride (16.5 g, 0.129 mol) in THF (350 mL). After 45 min of vigourous stirring the reaction mixture was warmed to −60° C. and pourred into 1M aqueous sodium potassium tartrate (500 mL) and stirred for 2 h at r.t. The mixture was then acidified with acetic acid (150 mL) and extracted three times with EtOAc. The combined organic phases were washed with brine and dried over $Na_2SO_4$. The residual oil was dissolved in ether and a solution of diazomethane in ether (about 300 mL, 0.15 mol) was added until the yellow color remained. An aqueous solution of $NH_4Cl$ was added and the ester was extracted with EtOAc and dried over $MgSO_4$. The oil was purified by flash chromatography with 2:3 EtOAc:hexane to yield the title compound (13.5 g, 72%).

$^1H$ NMR ($CDCl_3$) δ 1.00 (6H, s), 2.33 (3H, br s), 3.42 (2H, s), 3.70 (3H, s).

Step 9

Methyl 4-(acetylthio)-3,3-dimethylbutanoate

To a solution of triphenylphosphine (107.8 g, 0.411 mol) in THF (700 mL) maintained at 0° C. was added dropwise DEAD (diethyl azodicarboxylate) (64.7 mL, 0.411 mol) and the mixture was stirred at 0° C. for 30 min until the complex was precipitated. A solution of the alcohol of Step 8 (30 g, 0.205 mol) and thiolacetic acid (29.4 mL, 0.411 mol) in THF (300 mL) was then added dropwise (mechanical stirring). After 4 days at 4° C. the reaction mixture was evaporated to dryness, the white precipitate was suspended in 30:1 hexane:EtOAc and filtered. The residual oil was then purified by a flash chromatography using toluene then 100:1 toluene:EtOAc to yield the title compound.

Yield: 31 g, 74%. $^1H$ NMR ($CDCl_3$) δ 1.05 (6H, s), 2.27 (2H, s), 2.37 (3H, s), 3.00 (2H, s), 3.65 (3H, s).

Step 10

Methyl 4-((1(R)-(3-(2-(7-chloro-2-quinolinyl)ethenyl)phenyl)- 3-(2-(2-(2-tetrahydropyranyloxy)- 2-propyl)phenyl)propyl)thio)- 3,3-dimethylbutanoate The thiol acetate of Step 9 (7.52 g, 0.037 mol) was dissolved in $CH_3CN$ (50 mL) and argon was bubbled through the solution for 10 min. At 0° C., hydrazine (1.4 mL, 0.044 mol) was then added dropwise and the mixture was stirred 1 h at 0° C. This solution was then added to a suspension of the mesylate of Step 7 (15.2 g, 0.025 mol) and $Cs_2CO_3$ (20 g, 0.061 mol) in $CH_3CN$ (50 mL) maintained at 0° C. The reaction mixture was warmed to r.t. for 5 h and water was added. The product was extracted with EtOAc, washed with brine and dried over $Na_2SO_4$. The residual oil was purified by flash chromatography using 1:10 to 1:7 EtOAc:hexane to give 15.1 g, 89% yield, of the title compound.

$^1H$ NMR ($CDCl_3$) δ 1.03 (6H, s), 1.40 (6H, m), 1.60 to 1.70 (6H, three s), 2.20 (2H, m), 2.30 to 2.55 (4H, m), 2.65, 2.92, 3.10 and 3.40 (2H, four td), 3.33 (1H, m), 3.60 (3H, s), 3.90 (2H, t), 4.33 (1H, m), 7.08 to 7.55 (9H, m), 7.68 (3H, m), 7.75 (1H, m), 8.10 (2H, m).

Step 11

4-((1(R)-(3-(2-(7-chloro-2-quinolinyl)ethenyl)phenyl)- 3-(2-(2-hydroxy-2-propyl)phenyl)propyl)thio)- 3,3-dimethylbutanoic acid A solution of the product of Step 10 (10.1 g, 0.015 mol) and pyridinium p-toluenesulfonate (1.12 g, 0.045 mol) in a mixture of MeOH:THF 3:1 (80 mL) was warmed to 60° C. overnight. Most of the MeOH was evaporated and an aqueous solution of $NH_4Cl$ was added. The product was extracted with EtOAc, washed with brine and dried over $Na_2SO_4$. The residual oil was purified by flash chromatography on silica using 1:5 to 1:3 EtOAc:hexane. The product was then dissolved in a mixture of MeOH:THF, 3:1 (70 mL) and the solution was cooled down to 0° C. for the addition of a 1M solution of NaOH in water (35 mL, 0.036 mol). The reaction mixture was stirred 2 days at r.t. Most of the MeOH was evaporated and the solution was acidified with AcOH (acetic acid) to pH ≅5. An aqueous solution of $NH_4Cl$ was added and the acid was extracted with EtOAc. The organic phases were washed with brine and dried over Na$_2$SO$_4$. After evaporation of the solvent, the residual oil was purified by flash chromatography using 1:6 to 1:5 EtOAc:hexane (containing 2% AcOH) to give 7.6 g of the title product (87% yield).

$^1$H NMR (CDCl$_3$) δ 1.05 (6H, two s), 1.60 (6H, two s), 2.25 (2H, m), 2.40 (2H, s), 2.58 (2H, s), 2.92 (1H, m), 3.17 (1H, m), 3.90 (1H, t), 7.08 to 7.68 (13H, m), 8.10 (2H, m).

Step 12

To a solution of the acid of Step 11 in ethanol was added 1.0 equiv of 1N NaOH. The solvent was evaporated and the remaining oil was dissolved in water and freeze-dried to yield the title compound.

Anal. calcd. for C$_{35}$H$_{37}$ClNO$_3$SNa•2H$_2$O: C, 65.05; H, 6.40; N, 2.17; S, 4.96. Found: C, 65.32; H, 6.23; N, 2.14; S, 4.63. MS, m/e (relative intensity) 632 (100, M+Na), 610 (74, M+1)

EXAMPLE 147

2-(2-(3(S)-(3-(2-(7-chloro-2-quinolinyl)ethenyl)phenyl)-3-((5-hydroxy-5-methylhexyl)thio)propyl)phenyl)butanoic acid The title compound was prepared according to Example 138, except that the thiol was replaced by 6-mercapto-2-methyl-2-hexanol. This thiol was prepared by first reacting δ-valerolactone with an excess of methylmagnesium bromide. Selective tosylation of the primary alcohol followed by thiolacetate displacement gave the thiol ester. LiOH saponification gave the free thiol.

EXAMPLE 155

6-(3-(2-(7-chloro-2-quinolinyl)ethenyl)phenyl)-6-((3-hydroxy- 3-methylbutyl)thio)-3,3-dimethylhexanoic acid 3,3-dimethyl-δ-valerolactone was treated with HI in HOAc, followed by diazomethane to give methyl 3,3-dimethyl-5-iodo-pentanoate. This material and the aldehyde from U.S. Pat. No. 4,851,409, Example 24, Step 1 were assembled using Method L. The thiol was from Example 80, Step 4. This compound showed signals at m/e 548 (M+1) and 570 (M+Na) in a fast atom bombardment mass spectrometer (FAB-MS).

EXAMPLE 160

6-(3-(2-(7-chloro-2-quinolinyl)ethenyl)phenyl)-6-((( 2-(2-hydroxy-2-propyl)phenyl)methyl)thio)-3,3-dimethylhexanoic acid This compound was prepared according to Example 155, using 2-(2-(mercaptomethyl)phenyl)-2-propanol as the thiol. This thiol is obtained by first reacting phthalide with excess methylmagnesium bromide to give the diol. Selective monomesylation of the primary alcohol, followed by thiolacetate displacement gave the thiol ester, which was cleaved with hydrazine to free the thiol.

EXAMPLE 161

Sodium 1-(((1(R)-(3-(2-(7-chloro-2-quinolinyl)ethenyl)phenyl)- 3-(2-(2-hydroxy-2-propyl)phenyl)propyl)thio)methyl)cyclopropaneacetate

Step 1

1,1-cyclopropanedimethanol

A solution of lithium aluminum hydride (50 g, 1.32 mol) in 1.6 L of THF was cooled to −18° C. under N$_2$. A solution of diethyl 1,1-cyclopropanedicarboxylate (175 g, 0.94 mol) in 1.2 L of THF was then added dropwise over 50 min, at such a rate that the internal temperature of the reaction remained below 10° C. The cooling bath was then removed, and after 15 min, the temperature had reached 15° C. The reaction was then quenched by careful addition of 50 mL H$_2$O, followed by 50 mL of 15% NaOH, and then 150 mL of H$_2$O. After the mixture turned white, it was filtered through celite, and the bed was washed with 4 L of THF. Evaporation gave an oil which was distilled to give 81 g (0.79 mol, 84%) of the title compound as a colorless oil, b.p. 131°–138° C./15 mm Hg.

$^1$H NMR (CDCl$_3$) δ 0.48 (4H, s), 3.30 (2H, s), 3.58 (4H, s).

Step 2

1-(hydroxymethyl)cyclopropanemethyl benzoate

To a solution of the diol of Step 1 (81 g, 0.79 mol) and pyridine (96 mL, 1.19 mol) in CH$_2$Cl$_2$ (1 L) cooled at 0° C. was added slowly benzoyl chloride (121 mL, 1.03 mol). The reaction mixture was warmed to r.t. overnight and then poured in an aqueous solution of NH$_4$Cl. The products were extracted in CH$_2$Cl$_2$, washed with brine and dried over Na$_2$SO$_4$. The residual oil was purified by flash chromatography with 2:1 hexane:EtOAc and then 1:2 hexane:EtOAc to yield first, 116 g (47% yield) of the diester, then 89 g (547% yield) of the title alcohol.

$^1$H NMR (CDCl$_3$) δ 0.65 (4H, m), 2.20 (1H, t), 3.53 (2H, d), 4.35 (2H, s), 7.45 (2H, m), 7.60 (1H, m), 8.07 (2H, m).

Step 3

1-(benzoyloxymethyl)cyclopropaneacetonitrile

To a solution of the alcohol of Step 2 (80 g, 0.388 mol) and triethylamine (162 mL, 1.16 mol) in CH$_2$Cl$_2$ (1.5 L) cooled at −40° C. was added methanesulfonyl chloride (75 mL, 0.504 mol). The reaction mixture was warmed to −10° C. for 20 min and then poured into an aqueous solution of NaHCO$_3$ and extracted with CH$_2$Cl$_2$. The organic phases were washed with brine and dried over Na$_2$SO$_4$. The residual oil was then dissolved in DMSO (1.5 L) and sodium cyanide was added (86 g, 1.76 mol) portionwise. The reaction mixture was stirred at r.t. for 3 days then poured in an aqueous solution of NaHCO$_3$ and extracted with Et$_2$O. The organic phases were washed with brine and dried over Na$_2$SO$_4$. Evaporation of the solvent afforded the title product.

$^1$H NMR (CDCl$_3$) δ 0.80 (4H, m), 2.62 (2H, s), 4.27 (2H, s), 7.48 (2H, m), 7.60 (1H, m), 8.08 (2H, m).

Step 4

Methyl 1-(hydroxymethyl)cyclopropaneacetate

The nitrile of Step 3 (0.388 mol) was dissolved in ethanol (400 mL), 8N KOH (800 mL) was added and the reaction mixture was heated to reflux overnight. Most of the ethanol was evaporated and ice was added to the mixture. Concentrated HCl was added (600 mL) dropwise at 0° C. (without warming over 10° C. inside the solution) until obtention of pH≡1. The acid was then extracted with EtOAc two times and the organic phases were washed 2 times with brine and dried over Na$_2$SO$_4$. The solvent was evaporated and the solid was dissolved in THF (500 mL). A solution of diazomethane in Et$_2$O (about 1.7 L, 0.85 mol) was added at 0° C. until the yellow color remained and no more acid can be seen by TLC. The solvent was evaporated and the residual oil was purified by flash chromatography using 1:1 to 2:1 EtOAc:hexane to yield 28.2 g, (50% yield) of the title compound.

$^1$H NMR (CDCl$_3$) δ 0.55 (4H, m), 2.45 (2H, s), 2.55 (1H, t), 3.5 (2H, d), 3.70 (3H, s).

Step 5

Methyl 1-(acetylthiomethyl)cyclopropaneacetate

To a solution of the alcohol of Step 4 (28.2 g, 0.20 mol) and triethylamine (82 mL, 0.59 mol) in dichloromethane (1 L) cooled to –40° C. was added methanesulfonyl chloride (43.5 mL, 0.3 mol). The reaction mixture was warmed to –10° C. for 20 min and then an aqueous solution of NaHCO$_3$ was added. The product was extracted with CH$_2$Cl$_2$, washed with brine and dried over Na$_2$SO$_4$. A portion of this mesylate (0.053 mol) was then dissolved in DMF (180 mL) and cooled to 0° C. Freshly prepared cesium thiol acetate (J. Org. Chem., 2, 3664, (1986)) (22 g, 0.11 mol) was added and the mixture was stirred overnight at r.t. The reaction mixture was poured into an aqueous solution of NaHCO$_3$ and extracted with Et$_2$O. The organic phases were washed with brine and dried over Na$_2$SO$_4$. The residual oil was then purified by flash chromatography with 10:1 hexane:EtOAc to yield 7.5 g, 70%, of the title compound.

$^1$H NMR (CDCl$_3$) δ 0.60 (4H, m), 2.30 (2H, s), 2.35 (3H, s), 3.03 (2H, s), 3.70 (3H, s).

Step 6

Using the procedure of Example 146, Steps 10–12, the thiol acetate of Step 5 was used to prepare the title compound.

Anal. calcd for C$_{35}$H$_{35}$ClNO$_3$SNa: C, 67.13; H, 5.96; N, 2.24. Found: C, 67.01; H, 5.95; N, 1.97. MS, m/e (relative intensity) 630 (42, M+Na), 608 (21, M+1).

What is claimed is:

1. A compound of the formula:

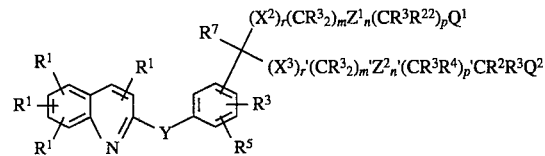

I wherein:

R$^1$ is H, halogen, —CF$_3$, —CN, —NO$_2$, or N$_3$;

R$^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl, substituted or unsubstituted 2-phenethyl, or two R$^2$ groups joined to the same carbon to form a carbocyclic ring of up to 8 members;

R$^3$ is H or R$^2$;

R$^4$ is halogen, —NO$_2$, —CN, —OR$^3$, —SR$^3$, NR$^3$R$^3$, NR$^3$C(O)R$^7$ or R$^3$;

R$^5$ is H, halogen, —NO$_2$, —N$_3$, —CN, —SR$^2$, —NR$^3$R$^3$, —OR$^3$, lower alkyl, or —C(O)R$^3$;

R$^6$ is —(CH$_2$)$_S$—C(R$^7$R$^7$)—(CH$_2$)$_S$—R$^8$ or —CH$_2$C(O)NR$^{12}$R$^{12}$;

R$^7$ is H or C$_1$-C$_4$ alkyl;

R$^8$ is the radical W—R$^9$;

R$^9$ contains up to 20 carbon atoms and is (1) an alkyl group or (2) an alkylcarbonyl group of an organic acyclic or monocyclic carboxylic acid;

R$^{11}$ is lower alkyl, —C(O)R$^{14}$, unsubstituted phenyl, or unsubstituted benzyl;

R$^{12}$ is H, or R$^{11}$;

R$^{13}$ is lower alkyl, lower alkenyl, lower alkynyl, —CF$_3$ or substituted or unsubstituted phenyl, benzyl, or 2-phenethyl;

R$^{14}$ is H or R$^{13}$;

R$^{16}$ is H, C$_1$-C$_4$ alkyl, or OH;

R$^{17}$ is lower alkyl, lower alkenyl, lower alkynyl, or substituted or unsubstituted phenyl, benzyl, or 2-phenethyl;

R$^{18}$ is lower alkyl, lower alkenyl, lower alkynyl, —CF$_3$ or substituted or unsubstituted phenyl, benzyl, or 2-phenethyl;

R$^{19}$ is lower alkyl, lower alkenyl, lower alkynyl, —CF$_3$ or substituted or unsubstituted phenyl, benzyl, or 2-phenethyl;

R$^{21}$ is H or R$^{17}$;

R$^{22}$ is R$^4$, CHR$^7$OR$^3$, or CHR$^7$SR$^2$;

m is 0–8;

m' is 2 or 3;

n and n' are independently 0 or 1, p and p' are independently 0–8;

m+n+p is 1–10 when r is 1 and X$^2$ is O, S, S(O), or S(O)$_2$;

m+n+p is 0–10 when r is 1 and X$^2$ is CR$^3$R$^{16}$;

m+n+p is 0–10 when r is 0;

m'+n'+p' is 2–10;

r and r' are independently 0 or 1;

s is 0–3;

Q$^1$ is —C(O)OR$^3$, 1H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O)NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH;

Q$^2$ is OH;

W is O, S, or NR$^3$;

X$^2$ and X$^3$ are independently O, S, S(O), S(O)$_2$, or CR$^3$R$^{16}$; with the proviso that at least one is S or SO$_2$;

Y is —CR$^3$=CR$^3$—

Z$^1$ and Z$^2$ are independently —HET(—R$^3$—R$^5$)—;

HET is the diradical of a benzene, a pyridine, a furan, or a thiophene;

and the pharmaceutically acceptable salts thereof.

2. A compound of claim 1 wherein:

R$^1$ is H, halogen, CF$_3$ or —CN;

R$^2$ is C$_1$-C$_4$ alkyl, —CF$_3$, —CHF$_2$, —CH$_2$F, or two R$^2$ groups joined to the same carbon to form a ring of up to 6 carbons;

R$^3$ is H or R$^2$;

R$^4$ is —OR$^3$, —SR$^3$, NR$^3$R$^3$, NHC(O)CH$_3$, or R$^3$;

R$^5$ is H or halogen;

R$^6$ is —(CH$_2$)$_S$—C(R$^7$R$^7$)—(CH$_2$)$_S$—R$^8$ or —CH$_2$C(O)NR$^{12}$R$^{12}$;

R$^7$ is H or C$_1$-C$_4$ alkyl;

R$^8$ is the radical W—R$^9$;

83

R⁹ contains up to 20 carbon atoms and is (1) an alkyl group or (2) an alkylcarbonyl group;

R¹¹ is lower alkyl, —C(O)R¹⁴, unsubstituted phenyl, or unsubstituted benzyl;

R¹² is H, or R¹¹;

R¹³ is lower alkyl, —CF₃, or substituted or unsubstituted phenyl, benzyl, or 2-phenethyl;

R¹⁴ is H or R¹³;

R¹⁶ is H, C₁–C₄ alkyl, or OH;

R²² is R⁴, —CH₂OR³, or —CH₂SR²;

m is 0–4;
m' is 2 or 3;
n and n' are independently 0 or 1;
p and p' are independently 0–4;
m+n+p is 1–9 when r is 1 and X² is O or S;
m+n+p is 0–9 when r is 1 and X² is CR³R¹⁶;
m+n+p is 0–9 when r is 0;
m'+n'+p' is 2–9;
r and r' are independently 0 or 1;
s is 0–3;
Q¹ is —C(O)OR³, 1H (or 2H)-tetrazol-5-yl, —C(O)OR⁶, —C(O)NHS(O)₂R¹³, —C(O)NR¹²R¹², —NHS(O)₂R¹³;
Q² is OH;
W is O, S, or NH;
X² and X³ are independently O, S, or CR³R¹⁶; with the proviso that at least one is S;
Y is (E)—CH=CH—;
Z¹ and Z² are independently —HET(—R³—R⁵)—;
HET is the diradical of a benzene, pyridine, furan, or thiophene;

and the pharmaceutically acceptable salts thereof.

3. A compound of claim 1 wherein the R²² α to Q¹ is lower alkyl, CF₃ or substituted or unsubstituted phenyl.

4. A compound of claim 1 of the Formula Ia:

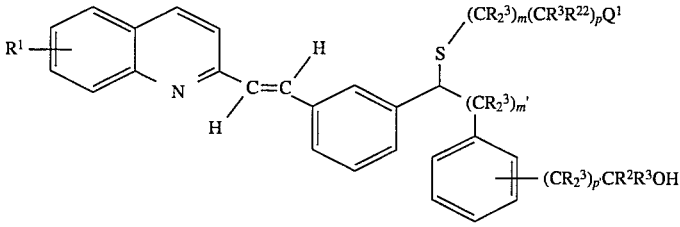

wherein:

84

R¹ is H, halogen, CF₃, or CN;

R²² is R³, —CH₂OR³, or —CH₂SR²;

Q¹ is —C(O)OH, 1H (or 2H)-tetrazol-5-yl, —C(O)NHS(O)₂R¹³, —C(O)NR¹²R¹², or —NHS(O)₂R¹³;

m' is 2 or 3;
p' is 0 or 1;
m+p is 1–5;

and the pharmaceutically acceptable salts thereof.

5. A compound of claim 4 wherein the carbon α to Q¹ is lower alkyl-substituted.

6. A compound of claim 1 of the Formula Ib:

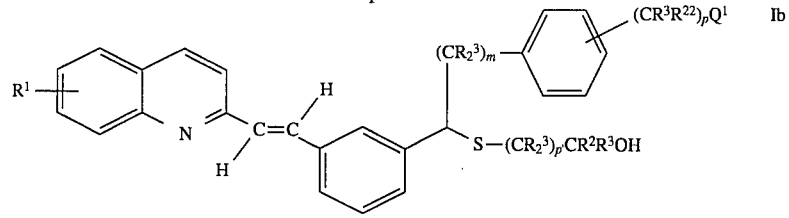

wherein:

R¹ is H, halogen, CF₃, or CN;

R²² is R³, —CH₂OR³, or —CH₂SR²;

Q¹ is —C(O)OH, 1H (or 2H)-tetrazol-5-yl, —C(O)NHS(O)₂ᴿ¹³, —C(O)NR¹²R¹², or —NHS(O)₂R¹³;

m is 0, 2 or 3;
p is 0 or 1;
p' is 2–4;
m+p is 0–4;

and the pharmaceutically acceptable salts thereof.

7. A compound of claim 1 of Formula I'

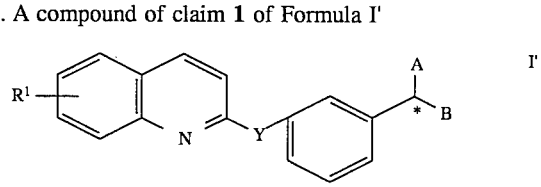

wherein the substituents are as follows:

| *   | R¹    | Y     | A                                      | B                                         |
|-----|-------|-------|----------------------------------------|-------------------------------------------|
| [RS | 7-Cl  | C≡C   | SCH$_2$CHMeCO$_2$H                     | (CH$_2$)$_2$(1,2-phe)CMe$_2$OH]           |
| RS  | 7-Cl  | CH=CH | S(CH$_2$)$_2$CO$_2$H                   | (CH$_2$)$_2$(1,2-phe)C((CH$_2$)$_4$)OH    |
| RS  | 7-Cl  | CH=CH | S(CH$_2$)$_2$CO$_2$H                   | (CH$_2$)$_2$(4-Cl-1,2-phe)CMe$_2$OH       |
| [RS | 7-Cl  | CH=CH | SCH$_2$CHMeCO$_2$H                     | (1,3-phe)CMe$_2$OH]                       |
| RS  | 7-Cl  | CH=CH | S(CH$_2$)$_2$CO$_2$H                   | (CH$_2$)$_2$(1,2-phe)CMe$_2$OH            |
| RS  | 7-Cl  | CH=CH | SCH$_2$CHMeCO$_2$H                     | S(CH$_2$)$_2$(1-c-Pen)OH                  |
| RS  | 7-Cl  | CH=CH | SCH$_2$(R)CHMeCO$_2$H                  | S(CH$_2$)$_2$(1,2-phe)CMe$_2$OH           |
| [S  | 7-Cl  | C≡C   | SCH$_2$(S)CHMeCO$_2$H                  | (CH$_2$)$_2$(1,2-phe)CMe$_2$OH            |
| RS  | 7-Cl  | CH=CH | SCH$_2$CHMeCO$_2$H                     | (1,4-phe)CMe$_2$OH                        |
| RS  | 7-Cl  | C≡C   | SCH$_2$CHEtCO$_2$H                     | (CH$_2$)$_2$(1,2-phe)CMe$_2$OH            |
| RS  | 7-Cl  | CH=CH | SCH$_2$CHEtCO$_2$H                     | (1,3-phe)CMe$_2$OH]                       |
| S   | 7-Cl  | CH=CH | SCH$_2$(S)CHEtCO$_2$H                  | (CH$_2$)$_3$(1,2-phe)CMe$_2$OH            |
| RS  | 7-Cl  | CH=CH | S(CH$_2$)$_2$CHMeCO$_2$H               | (CH$_2$)$_2$(1,2-phe)CMe$_2$OH            |
| [RS | 7-Cl  | C≡C   | S(CH$_2$)$_2$CO$_2$H                   | (CH$_2$)$_2$(1,2-phe)CMe$_2$OH]           |
| RS  | 7-Cl  | CH=CH | SCH$_2$CHMeCO$_2$H                     | (CH$_2$)$_2$(1,2-phe)CMe$_2$OH            |
| S   | 7-Cl  | CH=CH | SCH$_2$(S)CHMeCO$_2$H                  | (CH$_2$)$_2$(1,2-phe)CMe$_2$OH            |
| R   | 7-Cl  | CH=CH | SCH$_2$(S)CHMeCO$_2$H                  | (CH$_2$)$_2$(1,2-phe)CMe$_2$OH            |
| S   | 7-Cl  | CH=CH | S(CH$_2$)$_2$CO$_2$H                   | S(CH$_2$)$_2$CMe$_2$OH                    |
| S   | 7-Cl  | CH=CH | SCH$_2$CHMeCO$_2$H                     | (CH$_2$)$_2$(1,2-phe)C(CF$_3$)$_2$OH      |
| RS  | 7-Cl  | CH=CH | SCH$_2$CHMeCO$_2$H                     | (CH$_2$)$_2$(1,3-phe)C(CF$_3$)$_2$OH      |
| RS  | 7-Cl  | CH=CH | SCH$_2$CHMeCO$_2$H                     | (CH$_2$)$_2$(1,3-phe)CMe$_2$OH            |
| RS  | 7-Cl  | CH=CH | SCH$_2$CHEtCO$_2$H                     | SCH$_2$CMe$_2$CMe$_2$OH                   |
| RS  | 7-Cl  | CH=CH | SCH$_2$CHMeCMe$_2$OH                   | (CH$_2$)$_2$(1,2-phe)CO$_2$H              |
| RS  | 7-Cl  | CH=CH | SCH$_2$CHMeCMe$_2$OH                   | (CH$_2$)$_2$(1,2-phe)CONH$_2$             |
| RS  | 7-Cl  | CH=CH | SCH$_2$CHMeCO$_2$H                     | SCH$_2$(1,2-phe)CMe$_2$OH                 |
| RS  | 7-Cl  | CH=CH | SCH$_2$CHMeCO$_2$H                     | (CH$_2$)$_2$(1,4-phe)CMe$_2$OH            |
| RS  | 7-Cl  | CH=CH | SCH$_2$CHEtCO$_2$H                     | (CH$_2$)$_2$(1,2-phe)CMe$_2$OH            |
| RS  | 7-Cl  | CH=CH | SCH$_2$CH(OMe)CO$_2$H                  | (CH$_2$)$_2$(1,2-phe)CMe$_2$OH            |
| S   | 7-Cl  | CH=CH | SCH$_2$(R)CHEtCO$_2$H                  | (CH$_2$)$_2$(1,2-phe)CMe$_2$OH            |
| RS  | 7-Cl  | CH=CH | S(CH$_2$)$_2$CO$_2$H                   | (CH$_2$)$_2$(1,2-phe)CH(CF$_3$)OH         |
| S   | 7-Cl  | CH=CH | SCH$_2$(R)CHMeCO$_2$H                  | (CH$_2$)$_2$(1,2-phe)CMe$_2$OH            |
| S   | 7-Cl  | CH=CH | SCH$_2$(S)CHEtCO$_2$H                  | (CH$_2$)$_2$(1,2-phe)CMe$_2$OH            |
| RS  | 7-Cl  | CH=CH | SCH$_2$CMe$_2$CO$_2$H                  | (CH$_2$)$_2$(1,2-phe)CMe$_2$OH            |
| R   | 7-Cl  | CH=CH | S(R)CHMeCH$_2$CO$_2$H                  | (CH$_2$)$_2$(1,2-phe)CMe$_2$OH            |
| R   | 7-Cl  | CH=CH | S(S)CHMe(S)CHMeCO$_2$H                 | (CH$_2$)$_2$(1,2-phe)CMe$_2$OH            |
| R   | 7-Cl  | CH=CH | S(R)CHMe(R)CHMeCO$_2$H                 | (CH$_2$)$_2$(1,2-phe)CMe$_2$OH            |
| R   | 7-Cl  | CH=CH | SCHEtCH$_2$CO$_2$H                     | (CH$_2$)$_2$(1,2-phe)CMe$_2$OH            |
| S   | 7-Cl  | CH=CH | S(CH$_2$)$_3$CHMeOH                    | (CH$_2$)$_2$(1,2-phe)CHEtCO$_2$H          |
| [S  | 7-Cl  | CH=CH | SCH$_2$(S)CHMeCO$_2$H                  | (CH$_2$)$_2$(4-OMe-1,2-phe)CMe$_2$CO$_2$H] |
| R   | 7-Cl  | CH=CH | SCHMe$_2$CH$_2$CO$_2$H                 | (CH$_2$)$_2$(1,2-phe)CMe$_2$OH            |
| R   | 7-Cl  | CH=CH | SCH$_2$CHMeCH$_2$CO$_2$H               | (CH$_2$)$_2$(1,2-phe)CMe$_2$OH            |
| R   | 7-CF$_3$ | CH=CH | SCH$_2$CMe$_2$CH$_2$CO$_2$H         | (CH$_2$)$_2$(1,2-phe)CMe$_2$OH            |
| [S  | 7-CN  | CH=CH | SCH$_2$CMe$_2$CH$_2$CO$_2$H            | (CH$_2$)$_2$(1,2-phe)CO$_2$H]             |
| S   | 7-Cl  | CH=CH | S(CH$_2$)$_3$CMe$_2$OH                 | (CH$_2$)$_2$(1,2-phe)(R)CHEtCO$_2$H       |
| S   | 7-Cl  | CH=CH | S(CH$_2$)$_3$CMe$_2$OH                 | (CH$_2$)$_2$(1,2-phe)(S)CHEtCO$_2$H       |
| S   | 7-Cl  | CH=CH | S(CH$_2$)$_3$CMe$_2$OH                 | (CH$_2$)$_2$(4-Cl-1,2-phe)CHEtCO$_2$H     |
| S   | 7-Cl  | CH=CH | S(CH$_2$)$_3$CMe$_2$OH                 | (CH$_2$)$_2$(1,2-phe)CEt$_2$CO$_2$H       |
| S   | 7-Cl  | CH=CH | S(CH$_2$)$_3$CMe$_2$OH                 | (CH$_2$)$_2$(1,2-phe)CH$_2$CO$_2$H        |
| S   | 7-Cl  | CH=CH | S(CH$_2$)$_3$CMe$_2$OH                 | (CH$_2$)$_2$(1,2-phe)CH(OH)CO$_2$H        |
| S   | 7-Cl  | CH=CH | S(CH$_2$)$_3$CMe$_2$OH                 | (CH$_2$)$_2$(1,2-phe)CHEtCO$_2$H          |
| S   | 7-Cl  | CH=CH | S(CH$_2$)$_3$CMe$_2$OH                 | (CH$_2$)$_2$CHMeCH$_2$CO$_2$H             |
| R   | 7-Cl  | CH=CH | SCH$_2$CMe$_2$CH$_2$CO$_2$H            | (CH$_2$)$_2$(1,2-phe)CMe$_2$OH            |
| S   | 7-Cl  | CH=CH | S(CH$_2$)$_4$CMe$_2$OH                 | (CH$_2$)$_2$(1,2-phe)CHEtCO$_2$H          |
| S   | 6-Cl  | CH=CH | S(CH$_2$)$_3$CMe$_2$OH                 | (CH$_2$)$_2$(1,2-phe)CO$_2$H              |
| S   | 8-Cl  | CH=CH | S(CH$_2$)$_3$CMe$_2$OH                 | (CH$_2$)$_2$(1,2-phe)CO$_2$H              |
| S   | 7-F   | CH=CH | S(CH$_2$)$_3$CMe$_2$OH                 | (CH$_2$)$_2$(1,2-phe)CHEtCO$_2$H          |
| S   | 7-Br  | CH=CH | S(CH$_2$)$_3$CMe$_2$OH                 | (CH$_2$)$_2$(1,2-phe)CHMeCO$_2$H          |
| S   | 7-I   | CH=CH | SCH$_2$C(1,1-c-Pr)CH$_2$CO$_2$H        | (CH$_2$)$_2$(1,2-phe)CMe$_2$OH            |
| S   | 7-NO$_2$ | CH=CH | SCH$_2$C)1,1-c-Pr)CH$_2$CO$_2$H     | (CH$_2$)$_2$(1,2-phe)CMe$_2$OH            |
| R   | 7-N$_3$ | CH=CH | SCH$_2$C(1,1-c-Pr)CH$_2$CO$_2$H      | (CH$_2$)$_2$(1,2-phe)CMe$_2$OH            |
| RS  | 7-Cl  | CH=CH | S(CH$_2$)$_2$CMe$_2$OH                 | (CH$_2$)$_2$CMe$_2$CH$_2$CO$_2$H          |
| R   | 7-Cl  | CH=CH | S(1,2-phe)CH$_2$CO$_2$H                | (CH$_2$)$_2$(1,2-phe)CMe$_2$OH            |
| R   | 7-Cl  | CH=CH | S(CH$_2$)$_3$CMe$_2$OH                 | (CH$_2$)$_2$(1,2-phe)CHEtCO$_2$H          |
| S   | 7-Cl  | CH=CH | S(CH$_2$)$_2$CMe$_2$OH                 | (CH$_2$)$_2$(1,2-phe)CHEtCO$_2$H          |
| S   | 7-Cl  | CH=CH | S(CH$_2$)$_3$CMe(4-Cl—Ph)OH            | (CH$_2$)$_2$(1,2-phe)CHEtCO$_2$H          |
| R   | 7-Cl  | CH=CH | SCH$_2$(1,2-phe)CMe$_2$OH              | (CH$_2$)$_2$CMe$_2$CH$_2$CO$_2$H          |
| R   | 7-Cl  | CH=CH | SCH$_2$(1,1-c-Pr)CH$_2$CO$_2$H         | (CH$_2$)$_2$(1,2-phe)CMe$_2$OH            |
| R   | 7-Cl  | CH=CH | SCH$_2$(1,1-c-Bu)CH$_2$CO$_2$H         | (CH$_2$)$_2$(1,2-phe)CMe$_2$OH            |
| R   | 7-Cl  | CH=CH | SCH$_2$CMe$_2$CHMeCO$_2$H              | (CH$_2$)$_2$(1,2-phe)CMe$_2$OH            |
| S   | 7-Cl  | CH=CH | SCH$_2$(1,2-phe)CMe$_2$OH              | (CH$_2$)$_2$CMe$_2$CH$_2$CO$_2$H          |
| R   | 7-Cl  | CH=CH | SCHMeCMe$_2$CH$_2$CO$_2$H              | (CH$_2$)$_2$(1,2-phe)CMe$_2$OH            |
| R   | 7-Cl  | CH=CH | S(1,1-c-Pr)CH$_2$CO$_2$H               | (CH$_2$)$_2$(1,2-phe)CMe$_2$OH            |
| R   | 7-Cl  | CH=CH | S(1,1-c-Pr)CHMeCO$_2$H                 | (CH$_2$)$_2$(1,2-phe)CMe$_2$OH.           |

8. A pharmaceutical composition comprising a therapeutically effective amount of a compound of claim 1 and a pharmaceutically acceptable carrier.

9. The pharmaceutical composition of claim 8 additionally comprising an effective amount of a second active ingredient selected from the group consisting of non-steroidal anti-inflammatory drugs; peripheral analgesic agents; cyclooxygenase inhibitors; leukotriene antagonists; leukotriene bisynthesis inhibitors; $H_2$-receptor antagonists; antihistaminic agents; prostaglandin antagonists; thromboxane antagonists; thromboxane synthetase inhibitors; and ACE antagonists.

| * | $R^1$ | Y | A | B |
|---|---|---|---|---|
| RS | 7-Cl | CH=CH | $SCH_2CHMeCO_2H$ | (1,3-phe)$CMe_2OH$ |
| RS | 7-Cl | CH=CH | $SCH_2CHMeCO_2H$ | (1,4-phe)$CMe_2OH$ |
| RS | 7-Cl | CH=CH | $SCH_2CHEtCO_2H$ | (1,3-phe)$CMe_2OH$ |
| RS | 7-Cl | CH=CH | $SCH_2CHEtCO_2H$ | (1,2-phe)$CMe_2OH$ |
| RS | 7-Cl | C≡C | $SCH_2CHMeCO_2H$ | $(CH_2)_2$(1,2-phe)$CMe_2OH$ |
| S | 7-Cl | C≡C | $SCH_2(S)CHMeCO_2H$ | $(CH_2)_2$(1,2-phe)$CMe_2OH$ |
| RS | 7-Cl | C≡C | $SCH_2CHEtCO_2H$ | $(CH_2)_2$(1,2-phe)$CMe_2OH$ |
| RS | 7-Cl | C≡C | $S(CH_2)_2CO_2H$ | $(CH_2)_2$(1,2-phe)$CMe_2OH$ |
| RS | 7-Cl | CH=CH | $SCH_2CHMeCO_2H$ | $(CH_2)_2$(1,2-phe)$CMe_2NH_2$ |
| RS | 7-Cl | CH=CH | $SCH_2CHEtCO_2H$ | $(CH_2)_2$(1,2-phe)$CMe_2NHMe$ |
| RS | 7-Cl | CH=CH | $SCH_2CHEtCO_2H$ | $(CH_2)_2$(1,2-phe)$CMe_2NMe_2$ |
| RS | 7-Br | C≡C | $SCH_2CHEtCO_2H$ | $(CH_2)_2$(1,2-phe)$CMe_2OH$ |
| S | 7-Cl | CH=CH | $SCH_2CH(CH_2CH=CH_2)CO_2H$ | $(CH_2)_2$(1,2-phe)$CMe_2OH$ |
| S | 7-Cl | CH=CH | $SCH_2CHEtCO_2H$ | $(CH_2)_2$(1,2-phe)$C(CH_2OCH_2)OH$. |

10. A pharmaceutical composition of claim 9, wherein the second active ingredient is a non-steroidal anti-inflammatory drug.

11. A pharmaceutical composition of claim 10, wherein the weight ratio of said compound of claim 1 to said second active ingredient ranges from about 1000:1 to 1:1000.

12. A method of preventing the synthesis, the action, or the release of SRS-A or leukotrienes in a mammal which comprises administering to said mammal an effective amount of a compound of claim 1.

13. The method of claim 12 wherein the mammal is man.

14. A method of treating asthma in a mammal comprising administering to a mammal in need of such treatment a therapeutically effective amount of a compound of claim 1.

15. A method of treating inflammatory deseases of the eye in a mammal which comprises administering to a mammal in need of such treatment a therapeutically effective amount of a compound of claim 1.

16. The method of claim 15 wherein the mammal is man.

17. A compound of Formula I'

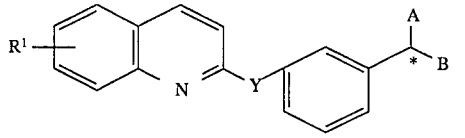

wherein the substituents are as follows:

18. 1-(((1(R)-(3-(2-(7-chloro-2-quinolinyl)ethenyl)phenyl)- 3-(2-(2-hydroxy-2-propyl)phenyl)propyl)thio)methyl) cyclopropaneacetic acid or a pharmaceutically acceptable salt thereof.

19. Sodium 1-(((1(R)-(3-(2-(7-chloro-2-quinolinyl)ethenyl)phenyl)- 3-(2-(2-hydroxy-2-propyl)phenyl)propyl)thio)methyl) cyclopropaneacetate.

20. A pharmaceutical composition comprising a pharmaceutical carrier and dispersed therein a therapeutically effective amount of a compuond of claim 18 and a pharmaceutically acceptable carrier.

21. A method of preventing the action of leukotrienes in a mammal which comprises administering to said mammal an effective amount of a compound of claim 18.

22. A method of treating asthma in a mammal comprising administering to a mammal in need of such treatment a therapeutically effective mount of a compound of claim 18.

23. A method of treating inflammatory diseases in the eye in a mammal which comprises administering to a mammal in need of such treatment a therapeutically effective mount of a compound of claim 18.

* * * * *

UNITED STATES PATENT AND TRADEMARK OFFICE
CERTIFICATE OF CORRECTION

PATENT NO. : 5,565,473

DATED : 10/15/96

INVENTOR(S) : M. Belley, et al

It is certified that error appears in the above-identified patent and that said Letters Patent is hereby corrected as shown below:

On the cover page, please add the notice: -- The term of this patent shall not extend beyond the expiration date of Pat. No. 5,266,568.--

Signed and Sealed this

Twenty-fifth Day of November, 1997

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,565,473

DATED : 10/15/96

INVENTOR(S) : Belley, et al

It is certified that error appears in the above-identified patent and that said Letters Patent is hereby corrected as shown below:

Claim 7 in the Table spanning columns 85 and 86, please delete the following entries:

| *   | $R^1$ | Y      | A                                          | B                                          |
|-----|-------|--------|--------------------------------------------|--------------------------------------------|
| [RS | 7-Cl  | C≡C    | $SCH_2CHMeCO_2H$                           | $(CH_2)_2(1,2\text{-phe})CMe_2OH]$         |
| [RS | 7-Cl  | CH=CH  | $SCH_2CHMeCO_2H$                           | $(1,3\text{-phe})CMe_2OH]$                 |
| [S  | 7-Cl  | C≡C    | $SCH_2(S)CHMeCO_2H$                        | $(CH_2)_2(1,2\text{-phe})CMe_2OH$          |
| RS  | 7-Cl  | CH=CH  | $SCH_2CHMeCO_2H$                           | $(1,4\text{-phe})CMe_2OH$                  |
| RS  | 7-Cl  | C≡C    | $SCH_2CHEtCO_2H$                           | $(CH_2)_2(1,2\text{-phe})CMe_2OH$          |
| RS  | 7-Cl  | CH=CH  | $SCH_2CHEtCO_2H$                           | $(1,3\text{-phe})CMe_2OH]$                 |
| [RS | 7-Cl  | C≡C    | $S(CH_2)_2CO_2H$                           | $(CH_2)_2(1,2\text{-phe})CMe_2OH]$         |
| [S  | 7-Cl  | CH=CH  | $SCH_2(S)CHMeCO_2H$                        | $(CH_2)_2(4\text{-OMe-1,2-phe})CMe_2CO_2H]$ |
| [S  | 7-CN  | CH=CH  | $SCH_2CMe_2CH_2CO_2H$                      | $(CH_2)_2(1,2\text{-phe})CO_2H]$           |

Signed and Sealed this

Ninth Day of June, 1998

*Attest:*

BRUCE LEHMAN

*Attesting Officer*    Commissioner of Patents and Trademarks

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 5,565,473 |
| ISSUED | : | October 15, 1996 |
| INVENTOR(S) | : | Michel L. Belley, et al. |
| PATENT OWNER | : | Merck Frosst Canada, Inc. |
| PRODUCT | : | SINGULAIR® (montelukast sodium) |

This is to certify that an application under 35 U.S.C. § 156 has been filed in the U.S. Patent and Trademark Office, requesting extension of the term of U.S. Patent No. 5,565,473 based upon the regulatory review of the product SINGULAIR® by the Food and Drug Administration. Since it appears that the requirements of the law have been met, this certificate extends the term of the patent for the period of 430 days from November 30, 2010, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

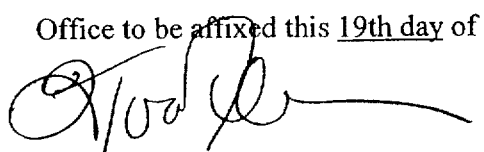

Q. Todd Dickinson
Under Secretary of Commerce for Intellectual Property and Director of the United States Patent and Trademark Office

(12) EX PARTE REEXAMINATION CERTIFICATE (7402nd)
United States Patent
Belley et al.

(10) Number: US 5,565,473 C1
(45) Certificate Issued: *Mar. 16, 2010

(54) UNSATURATED HYDROXYALKYLQUINOLINE ACIDS AS LEUKOTRIENE ANTAGONISTS

(75) Inventors: Michel L. Belley, Pierrefonds (CA); Serge Leger, Dollard des Ormeaux (CA); Marc Labelle, Ville d'Ile Perrot (CA); Patrick Roy, Pierrefonds (CA); Yi B. Xiang, Pierrefonds (CA); Daniel Guay, Montreal (CA)

(73) Assignee: Merck Sharp & Dohme Pharmaceuticals SRL, Bridgetown (BB)

Reexamination Request:
No. 90/009,432, Apr. 27, 2009

Reexamination Certificate for:
Patent No.: 5,565,473
Issued: Oct. 15, 1996
Appl. No.: 08/392,592
Filed: Feb. 23, 1995

(*) Notice: This patent is subject to a terminal disclaimer.

Certificate of Correction issued Nov. 25, 1997.

Certificate of Correction issued Jun. 9, 1998.

Related U.S. Application Data

(63) Continuation of application No. 07/774,414, filed on Oct. 10, 1991, now abandoned, which is a continuation-in-part of application No. 07/741,888, filed on Aug. 8, 1991, now abandoned, which is a continuation-in-part of application No. 07/596,887, filed on Oct. 12, 1990, now abandoned.

(51) Int. Cl.
C07D 215/18 (2006.01)
C07D 215/00 (2006.01)
C07D 215/12 (2006.01)

(52) U.S. Cl. .................. 514/313; 514/314; 514/826; 514/924; 546/162; 546/167; 546/171; 546/172; 546/174; 546/175; 546/176

(58) Field of Classification Search ............... None
See application file for complete search history.

(56) References Cited

U.S. PATENT DOCUMENTS

| | | | |
|---|---|---|---|
| 4,609,744 A | 9/1986 | Young et al. |
| 4,617,407 A | 10/1986 | Young et al. |
| 4,666,928 A | 5/1987 | Young et al. |
| 4,683,325 A | 7/1987 | Frenette et al. |
| 4,761,425 A | 8/1988 | Girard et al. |
| 4,820,867 A | 4/1989 | Belanger et al. |
| 4,845,108 A | 7/1989 | Young et al. |
| 4,851,409 A | 7/1989 | Young et al. |
| 4,857,659 A | 8/1989 | Frenette et al. |
| 4,920,132 A | 4/1990 | Huang et al. |
| 4,929,626 A | 5/1990 | Mohrs et al. |
| 4,962,203 A | 10/1990 | Young et al. |
| 4,970,215 A | 11/1990 | Mohrs et al. |
| 4,983,628 A | 1/1991 | Frenette et al. |
| 4,990,526 A | 2/1991 | Young et al. |
| 5,104,882 A | 4/1992 | Young et al. |
| 5,143,931 A | 9/1992 | Gleason et al. |
| 5,204,358 A | 4/1993 | Young et al. |
| 5,266,568 A | 11/1993 | Belley et al. |
| 5,270,324 A | 12/1993 | Zamboni et al. |
| 5,428,033 A | 6/1995 | Belley et al. |

FOREIGN PATENT DOCUMENTS

| | | |
|---|---|---|
| EP | 0 206 751 | 12/1986 |
| EP | 0 233 763 | 8/1987 |
| EP | 0 271 287 | 6/1988 |
| EP | 0 318 093 | 5/1989 |
| EP | 0 399 818 | 11/1990 |
| JP | 62-258362 | 11/1987 |
| JP | 2-138259 | 5/1990 |
| WO | WO 89/12629 | 12/1989 |
| WO | WO 92/05156 | 4/1992 |

OTHER PUBLICATIONS

Young, "The Development of New Anti–Leukotriene Drugs: L–648,051 and L–649,923, Specific Leukotriene $D_4$ Antagonists," Drugs of the Future, 1988, vol. 13, pp. 745–759.

Young, "Structural Analysis of Sulfido–Peptide Leukotrienes: Application to the Design of Potent and Specific Antagonists of Leukotriene $D_4$," Advances in Prostaglandin, Thromboxane, and Leukotriene Research, 1989, vol. 19, pp. 643–646.

Testa and Peter Jenner, "Drug Metabolism: Chemical and Biological Aspects," Chapter 1.1 Phase I Reactions, Section 1.1.1 Oxidative Reactions, pp. 1–116, 1976, Marcel Dekker, Inc., New York.

Rokach, et al. Leukotrienes and Lipoxygenases: Chemical, Biological and Clinical Aspects, Bioactive Molecules vol. II, pp. 490–491, Elsevier, 1989.

Ku, et al. "Synthesis and $LTD_4$ Antagonist Activity of 2–Norleukotriene Analogs," J. Med. Chem., 1985, 28 (12), 1847–1853.

(Continued)

Primary Examiner—Evelyn Huang

(57) ABSTRACT

Compounds having the formula I;

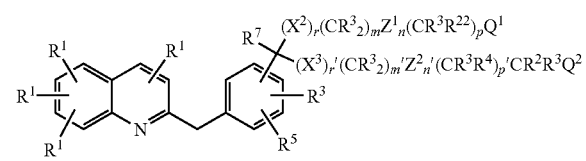

are leukotriene antagonists and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

OTHER PUBLICATIONS

Wood, et al. "Cyclopropane Fatty Acid Metabolism: Physical and Chemical Identification of Propane Ring Metabolic Products in the Adipose Tissue," J. Am. Oil Chemists' Soc., 1965, vol. 42, pp. 315–320 (1965).

B. Samuelssen et al. *Prostaglandins,* vol. 19, No. 5, 645–648 (1980).

Abraham Mazur & Benjamin Harrow, *Textbook of Biochemistry (10th Ed.),* W.B. Saunders Company, 338–346 (1971).

H. C. Bray et al., *Kinetic Studies of the Metabolism of Foreign Organic Compounds,* Biochem J., vol. 48, 88–96 (1951).

D. Robinson et al., *Studies in Detoxication, The Metabolism of Alkylbenzenes, isopropylbenzene(cumene) and Derivatives of Hydratopic Acid,* Biochemical J., vol. 59, 153–159 (1955).

Robert Thornton Morrison & Robert Neilson Boyd, *Organic Chemistry,* Allyn and Bacon,, Inc., 321–333 (1959).

Ernest L. Eliel, *Stereochemistry of the Carbon Compounds,* McGraw–Hill, 329–335 (1962).

A. L. McClellan, *Tables of Experimental Dipole Moments,* W.H. Freeman & Co., 24–25, 124–125, 184–185, 240–241, 254–255, 296–297, 579–581 (1963).

D. E. Green & D. W. Allmann, *Metabolic Pathways, vol. II: Lipids, Steroids and Carotenoids,* Academic Press, 30–31 (1968).

Arnold J. Gordon & Richard A. Ford, *The Chemist's Companion,* John Wiley & Sons, Inc., 2–17 (1972).

Paul B. Lazarow & Christian De Duve, *A fatty acyl–CoA oxidizing system in rat liver peroxisomes; enhancement by clofibrate, a hypolipidemic drug,* Proc. Nat. Acad. Sci. USA, vol. 73, No. 6, 2043–2046 (1976).

David E. Moody & Janardan K. Reddy, *Morphometric Analysis of the Ultrastructural Changes in Rat Liver Induced by The Peroxisome SaH 42–348,* The Journal of Cell Biology, vol. 71, 768–780 (1976).

Witold Senczuk & Barbara Litewka, *Absorption of cumene through the respiratory tract and excretion of diemthylphenylcarbinol,* Br. J. Indust. Med., vol. 33, No. 2, 100–105 (1976).

Miguel A. Ondetti et al., *Design of Specific Inhibitors of Angiotensin–Converting Enzyme: New Class of Orally Active Antihypertensive Agents,* Science, vol. 196, 441–444 (Apr. 22, 1977).

R. A. Appleton et al., *Antagonists of Slow Reacting Substance of Anaphylaxis. Synthesis of a Series of Chromone–2–carboxylic Acids,* J. Med. Chem., vol. 20, No. 3, 371–379 (1977).

Timothy Jen et al., *Synthesis and Potential beta–Adrenergic Agonist Activity of Some Meta–Substituted p–Hydroxyphenethanolamines Related to Salbutamol,* J. Med. Chem, vol. 20, No. 8, 1029–1035 (1977).

C. W. Thornber, *Isosterism and Molecular Modification in Drug Design,* Chem. Soc. Rev., 563–580 (1979).

John Caldwell, *Concepts in Drug Metabolism, Part A—Chapter 4: Conjugation Reactions,* Marcel Dekker, Inc., 211–250 (1980).

Peter Jenner & Bernard Testa, *Concepts in Drug Metabolism, Part A—Chapter 2: Structural Approach to Selectivity in Drug Metabolism and Disposition,* Marcel Dekker, Inc., 53–152 (1980).

Theodora W. Greene, *Protective Groups in Organic Synthesis,* John Wiley & Sons, 128–141 (1981).

Yasuko Koshishara et al., *Selective inhibition of 5–lipoxygenase by 5,6–methanoleukotriene Ad, a stable analogue of leukotriene A4,* FEBS Lett., vol. 143, No. 1, 13–16 (Jun. 1982).

Reddy et al., *Hepatic and Renal Effects of Peroxisome Proliferators: Biological Implications,* Annals New York Academy of Sciences, vol. 386, 81–110 (1982).

K. C. Nicolaou et al., *Ethanoarachidonic Acids. A New Class of Arachidonic Acid Cascade Modulators. 1. Monoethano Compounds,* J. Org. Chem., vol. 48, No. 26, 5400–5403 (1983).

K. C. Nicolaou et al., *Ethanoarachidonic Acids. A New Class of Arachidonic Acid Cascade Modulators. 2. Polyethano Compounds,* J. Org. Chem., vol. 48, 5403–5404 (1983).

Jurg R. Pfister & D. V. Krishna Murthy, *Synthesis of Three Potential Inhibitors of Leukotriene Biosynthesis,* J. Med. Chem., vol. 26, No. 8, 1099–1103 (1983).

Carl D. Perchonock et al., *Dimethyleicosatrienoic acids: Inhibitors of the 5–lipoxygenase enzyme,* Tet. Lett., vol. 24, No. 24, 2457–2460 (1983).

Yoshinobu Arai et al., *Synthesis and 5–Lipoxygenase Inhibitory Activities of Eicosanoid Compounds,* J. Med. Chem., vol. 26, No. 1, 72–78 (1983).

Patrick I. Eacho et al., *Characterization of Liver Enlargement Induced by Compound LY171883 in Rats,* Fundamental and Applied Toxicology, vol. 5, 794–803 (1985).

Slobodzian et al., *High–performance liquid chromatographic determination of hydroxymethyl–dibenzo[b,g]thiepin 5,5–dioxide and its acid metabolite in human plasma and urine,* J. Chrom., vol. 338, No. 1, 253–258 (Feb. 27, 1985).

Carl D. Perchonock, et al., *Synthesis and LTD4–Antagonist Activity of Desamino–2–Nor–Leukotriene Analogs,* Prostaglandins, vol. 29, No. 1, 75–81 (Jan. 1985).

Carl D. Perchonock et al., *Synthesis and Pharmacological Characterization of 5–(2–Dodecylphenyl)–4, 6–dithianonanedioic acid and 5–[2–(8–Phenyloctyl)phenyl] 4,6–dithianonanedioic Acid: Prototypes of a Novel Class of Leukotriene Antagonists,* J. Med. Chem., vol. 28, No. 9, 1145–1147 (Sep. 1985).

C.K. Buckner et al., *Pharmacological evidence that human inralobar airways do not contain different receptors that mediate contractions to leukotriene C4 and leukotriene D4,* J. Pharmacol. Exp. Thera., vol. 237, No. 2, 558–562 (1986).

R.N. Young et al., *Design and Synthesis of Sodium($\beta R^*$, $\gamma S^*$)–4–[[3–(4–Acetyl–3–hydroxy–2–propyl–phenoxy)-propyl]thio]–γ–hydroxy–β–methylbenzenebutanoate:A Novel Selective, and Orally Active Receptor Antagonist of Leukotriene D4,* J. Med. Chem., vol. 29, No. 9, 1573–1576 (Sep. 1986).

R.N. Young et al., *L–649,923, sodium (beta $S^*$, gamma $R^*$–4–(3–(4–acetyl–3–hydroxy–2–propylphenoxy)propylthio)–gamma–hydroxy–betamethylbenzenebutanoate. A selective, orally active leukotriene D4 receptor antagonist,* Advances in Prostaglandin, Thromboxane, and Leukotriene Research, vol. 16, 37–45 (1986).

John G. Gleason et al., *High–Affinity Leukotriene Receptor Antagonists. Synthesis and Pharmacological Characterization of 2–Hydroxy–3–[(2–carboxyethyl)thio]–3–[2–(8–phenyloctyl)phenyl]propanoic Acid,* J. Med. Chem., vol. 30, No. 6, 959–961 (Jun. 1987).

John H. Musser et al., *Substituted Arylmethyl Phenyl Ethers. 1. A Novel Series of 5–Lipoxygenase Inhibitors and Leukotriene Antagonists*, J. Med. Chem., vol. 30, No. 1, 96–104 (1987).

T. Hashimoto, *Comparison of Enzymes of Lipid B–Oxidation in Peroxisomes and Mitochondria*, Peroxisomes in Biology and Medicine, Springer Verlag, 97–104 (1987).

Edwin C. Friedrich, *Solvolysis of cyclopropyl–substituted derivatives, The Chemistry of the Cyclopropyl Group, Part 1*, John Wiley & Sons, 633–700 (1987).

Hung–Wen Liu & Christopher T. Walsh, *Biochemistry of the Cyclopropyl Group*, The Chemistry of the Cyclopropyl Group, Part 2, John Wiley & Sons, 959–1025 (1987).

R.A. Lewis et al., *Identification of the C(6)–S–Conjugate of Leukotriene A with Cysteine as Naturally occurring Slow Reacting Substance of Anaphylaxis (SRS–A). Importance of the II–CIS–Geometry for Biological Activity*, Biochem. Biophys. Res. Commun., vol. 96, 271–277 (Sep. 16, 1980).

John F. Newton et. al.,*In Vivo Metabolism of the Leukotriene Receptor Antagonist, 5–(2–Dodecylphenyl)–4, 6–Dithianoanedioic Acid (DK&F 102,081)in the Guinea Pig*, Drug Meta. Dispos., vol. 15, No. 2, 168–176 (1987).

John F. Newton et al., *In Vitro Microsomal Metabolism of the Leukotriene Receptor Antagonist, 5(2–Dodecylphenyl)–4, 6–Dithioanoanedioic Acid (DK&F 102,081)*, Drug Metal. and Dispos., vol. 15, No. 2, 161–167 (1987).

T. R. Jones et. al., *Pharmacology of L–660,711 (MK–571: a novel potent and selective leukotriene D4 receptor antagonist*, Canadian J. Physiol. and Pharmacology, vol. 67, No. 1, 17–28 (Jan. 1989).

R. N. Young, Abstract No. 98: *Structural Analysis of Sulfido–Peptide Leukotrienes Application to the Design of Potent and Specific Receptor Antagonists of Leukotriene D4*, Book of Abstracts, The Third Chemical Congress of North America, Jun. 5–10, 1988, Toronto, Ontario, Canada (1988).

Marc Lebel et al., *Benzyl Alcohol Metabolism and Elimination in Neonates*, Dev. Pharmacol. and Ther., vol. 11, 347–356 (Nov. 6, 1988).

Hisao Nakai et al., *New Potent Antagonists of Leukotrienes C4 and D4. I. Synthesis and Structure–Activity Relationships*, J. Med. Chem., vol. 31, No. 1, 84–91 (1988).

W. T. Stott, *Chemically Induced Proliferation of Peroxisomes: Implications for Risk Assessment*,Regulatory, Toxicology, and Pharmacology, vol. 8, 125–159 (1988).

Daniel S. Marsman et al., *Relationship of Hepatic Peroxisome Proliferation and Replicative DNA Synthesis to the Hepatocarcinogenicity of the Peroxisome Proliferators Di(ethylhexyl)phthalate and [4–chloro–6–(2, 3–xylidino)–2–pyrimidinylthio]acetic Acid (Wy–14,643)in Rats*, Cancer Research, vol. 48, 6739–6744 (Dec. 1, 1988).

Robert Young, *Developing Drugs Against Leukotrienes*, Canadian Chemical News, 7–16 (1988).

D.R. Hawkins, *Biotransformations*, Royal Society of Chemistry, Cambridge, vol. 2, 85 (1989).

M. Belley & R. Zamboni, *Addition of Thiols to Styrenes: Formation of Benzylic Thioethers*, J. Org. Chem., vol. 54, No. 5, 1230–1232 (Mar. 3, 1989).

R.N. Young et al., *L–660,711, a Potent Selective and Orally Active Antagonist of Leukotriene D4*, New Trends in Lipid Mediators Research, vol. 3, 62–66 (1989).

P. I. Eacho, et al., *Induction of Peroxisomal B–Oxidation in the Rat Liver in Vivo and in Vivo by Tetrazole–Substituted Acetophenones: Structure–Activity Relationships*, Toxicology and Applied Pharmacology, vol. 100, No. 1, 177–184 (Aug. 1989).

Brian J. Fitzsimmons & Joshua Rokach, Chapter 6: *Enzyme Inhibitors and Leukotriene Receptor Antagonists*, Bioactive Molecules, vol. 11, Leukotrienes and Lipoxygenases: Chemical, Biological and Clinical Aspects, 427–502 (1989).

A. W. Ford–Hutchinson, *The Use of Leukotriene D4 Receptor Antagonists and 5–Lipoxygenase Inhibitors to Define a Role for Leukotrienes in Allergic Reactions*, Advances in Prostglandin, Thromboxane, and Leukotriene Research, vol. 19, 507–510 (1989).

Cheuk K. Lau et al., *Chemistry of the Leukotrienes and other Lipoxygenase Products*, Bioactive Molecules, vol. 11, Leukotrienes and Lipoxygenases, 64–66 (1989).

John H. Musser et al., *N–[(Arylmethoxyp)phenyl and N–[(Arylmethoxy)naphthyl Sulfonamides: Potent Orally Active Leukotriene D4 Antagonists of Novel Structure*, J. Med. Chem., vol. 32, No. 6, 1176–1183 (Jun. 1989).

Rolf Kristian Berge et al., *Alkylthio Acetic Acids (3–Thia Fatty Acids)—A New Group of Non–β–Oxidizable Peroxisome–Inducing Fatty Acid Analogues–II*, Biochemical Pharmacology, vol. 38, No. 22, 3969–3979 (Nov. 15, 1989).

Rolf Kristian Berge et al., *Alkylthioacetic acid (3–thia fatty acids)—a new group of non–β–oxidizable peroxisome–inducing fatty acid analogues. I. A study on the structural requirements for proliferation of peroxisomes and mitochondria in rat liver*, Biochimica et Biophysica Acta, vol. 1004, No. 3, 345–356 (1989).

R.N. Young et al., Abstract, *Studies on the Characterization of the Leukotriene D4 Receptor*, for presentation at the Pacific Basin Societies 1989 International Chemical Congress, Honolulu, Hawaii, Dec. 17–22 (1989).

J. Y. Gauthier et al., *Stereospecific Synthesis, Assignment of Absolute Configuration, and Biological Activity of the Enantiomers of 3–[[[3–[2–(7–Chloroquinolin–2–yl)–(E)–ethenyl][[3–(dimethylamino)–3–oxopropyl]thio]methyl] thio]propionic Acid, A Potent and Specific Leukotriene D4 Receptor Antagonist*, J. Med. Chem., vol. 33, No. 10, 2841–2845 (1990).

M.E. Fitzsimmons & M.W Anders, *Fatty Acid B–Oxidation–Dependent Bioactivation of 5,6–Dichloro–4–Thia–5–Hexenoate and Analogs in Isolated Rat Hepatocytes*, Biological Reactive Intermediates IV, 281–284 (1990).

Victor G. Matassa et al., *Evolution of a Series of Peptidoleukotriene Antagonists: Synthesis and Structure/Activity Relationships of 1,3,5–Substituted Indoles and Indazoles*, J. Med. Chem., vol. 33, No. 6, 1781–1790 (Jun. 1990).

Jennifer B. Dressman et al., *Delivery System Technology*, Comprehensive Medicinal Chemistry, vol. 5, 615–660 (1990).

William Kingsbury et al., *Leukotriene Receptors*, Comprehensive Medicinal Chemistry, vol. 3, 763–796 (1990).

D. M. Hoover et al., *Effects of Chronic Treatment with the Leukotriene D4 Antagonist Compound LY171883 on Fischer 344 Rats and Rheus Monkeys*, Fundamental and Applied Toxicology, vol. 14, 123–130 (1990).

Raymond D. Youssefyeh et al., *Development of a Novel Series of (2–Qinolinylmethoxy)phenyl–Containing Compound as High–Affinity Leukotriene Receptor Antagonists. 1. Initial Structure–Activity Relationships*, J. Med. Chem., vol. 33, No. 4, 1186–1194 (Apr. 1990).

R.N. Young, Abstract, *Conformational Analysis and Molecular Modelling of Leukotriene Agonists and Antagonist: Application to the Design of Novel Anti–Asthma Drugs*, for presentation at the Canadian 73rd Chemical Conference and Exhibition, Nova Scotia, Jul. 15–21 (1990).

R.N. Young et al., *Conformational Analysis of Leukotrienes and Related Compounds for Mapping the Leukotriene D4 Receptor: Application to the Design of Novel Anti–Asthma Drugs*, Bioorganic Chemistry in Healthcare and Technology, vol. 207, 303–307 (1991).

I. Wahedna et al., *Effect of RG–12525, an oral leukotriene D4 antagonists, on the airway response to inhaled leukotriene D4 in subjects with mild asthma*, Br. J. Clin. Pharmac., vol. 32, 512–515 (Oct. 1991).

Robert N. Young, *Development of Novel Leukotriene–Based Anti–Asthma Drugs: MK–886 and MK–571*, New Drugs for Asthma Therapy, AAS 34, 179–187 (1991).

Theodora W. Greene & Peter G. M. Wutts, *Protective Groups in Organic Synthesis*, John Wiley & Sons, Inc., 198–210 (1991).

A. Shaw & R. D. Krell, *Peptide Leukotrienes: Current Status of Research*, J. Med. Chem., vol. 34, No. 4, 1235–1242 (Apr. 1991).

Anthony Ford–Hutchinson et al., *Leukotriene Blockers, Novel Therapeutic Strategies for the Treatment of Asthma*, Drug News & Perspectives, vol. 4, No. 5, 264–271 (Jun. 1991).

D. W. P. Hay et al. *Pharmacologic and Pharmacokinetic Profile of SK&F S–106203, a Potent, Orally Active Peptidoleukotriene Receptor Antagonist, in Guinea–pig*, Pulmonary Pharmacology, vol. 4, No. 3, 177–189 (1991).

T.R. Jones et al., *Pharmacology of the leukotriene antagonist verlukast: The (R)–enantiomer of MK–571*, Canadian Journal of Physiol. Pharmacology, vol. 69, 1847–1854 (1991).

Hiroko Kozuka et al., *Characteristics of Induction of Peroxisomal Fatty Acid Oxidation–related Enzymes in Rat Liver by Drugs*, Biochem Pharmacol., vol. 41, No. 4, 617–623 (Feb. 15, 1991).

J. Rokach, ed., *Leukotrienes and Lipoxygenases*, Elsevier, Amsterdam (1989).

P.F. Fitzpatrick and J.J. Villafranca, *Mechanism–Based Inhibitors of Dopamine β–Hydroxylase Containing Acetylenic or Cyclopropyl Groups*, J. Am. Chem. Soc., vol. 107, No. 17, 5022–5023 (Aug. 21, 1985).

Augstein et al., *Selective Inhibitor of Slow Reacting Substance of Anaphylaxis*, Nature New Biology, vol. 245, No. 146, 215–217 (Oct. 17, 1973).

Turnbull et al., *Slow reacting substance as a preformed mediator from human lung*, Immunology, vol. 31, No. 5, 813–820 (Nov. 1976).

Jakschik et al., *Precursor role of arachidonic acid in release of slow reacting substance from rat basophilic leukemia cells*, Proc. Natl. Acad. Sci. USA, vol. 74, No. 10, 4577–4581 (Oct. 1977).

Farmer et al., *Mediators of Passive Lung Anaphylaxis in the Rat*, Br. J. Pharmac, vol. 55, 57–64 (Sep. 1975).

Burka et al., *A Possible Modulatory Role for Prostacyclin (PG12) in IgGa—Induced Release of Slow–Reacting Substance of Anaphylaxis in Rats*, Br. J. Pharmac, vol. 61, 697–699 (1976).

Chand et al., *The Pharmacology of Anaphylaxis in the Chicken Intestine*, Br. J. Pharmac, vol. 57, 399–408 (Jul. 1976).

Engineer et al., *Release of Mediator of Anaphylaxis: Inhibition of Prostaglandin Synthesis and the Modification of Release of Slow Reacting Substance of Anaphylaxis and Histamine*, Br. J. Pharmac, vol. 62, 61–66 (Jan. 1978).

Örning et al., *Leukotriene D: A slow reacting substance from rat basophilic leukemia cells*, Proc. Natl. Acad. Sci. USA, vol. 77, No. 4, 2014–2017 (Apr. 1980).

Ahmed et al., *Abnormal Mucociliary Transport in Allergic Patients with Antigeninduced Bronchospasm: Role of Slow Reacting Substance of Anaphylaxis*, American Review of Respiratory Disease, vol. 124, No. 2, 110–114 (Aug. 1981).

MacGlashan et al., *Generation of Leukotrienes by Purified Human Lung Mast Cells*, J. Clin. Invest., vol. 70, 747–751 (Oct. 1982).

Murphy et al., *Leukotriene C: A slow–reacting substance from murine mastocytoma cells*, Proc. Natl. Acad. Sci. USA, vol. 76, No. 9, 4275–4279 (Sep. 1979).

Pong et al., *Characterization of a leukotriene D4 receptor in guinea pig lung*, Proc. Natl. Acad. Sci .USA, vol. 80, 7415–7419 (Dec. 1983).

Lewis, R, et al., *Contractile Activities of Structural Analogs of Leukotrienes C and D: Role of Polar Substituents*, Proc. Natl. Acad. Sci., USA, vol. 78, No. 7, 4579–4583 (Jul. 1981).

Buckner et al., *Analysis of Leukotriene Receptor Antagonists on Isolated Human Intralobar Airways*, Annals New York Academy of Sciences, vol. 524, Biology of the Leukotrienes, 181–186 (1988).

Aharony et al., *Kinetic and Pharmacologic Analysis of [3H] Leukotriene E4 Binding to Receptors on Guinea Pig Lung Membranes: Evidence for Selective Binding to a Subset of Leukotriene D4 Receptors*, The Journal of Pharmacology and Experimental Therapeutics, vol. 248, No. 2, 581–588 (Feb. 1989).

Buckner et al., *An Examination of the Influence of the Epithelium on Contractile Responses to Peptidoleukotrienes and Blockade by ICI 204,219 in Isolated Guinea Pig Trachea and Human Intralobar Airways*, The Journal of Pharmacology and Experimental Therapeutics, vol. 252, No. 1, 77–85 (1990).

Dahlén et al., *Inhibition of Allergic Bronchoconstriction in Asthmatics by The Leukotriene–Antagonist ICI 204,219*, Advances in Prostaglandin, Thromboxane, and Leukotriene Research, vol. 21A, 461–464 (1991).

Krell et al., *The Preclinical Pharmacology of ICI 204,219, A Peptide Leukotriene Antagonist*, American Review of Respiratory Disease, vol. 14, No. 4, Part 1, 978–987 (Apr. 1990).

Cheng & Prusoff, *Relationship between the inhibition constant ($k_1$) and the concentration of inhibitor which causes 50 per cent inhibition (I50)of an enzymatic reaction*, Biochem. Pharmacol., vol. 22, No. 23, 3099–3108 (1973).

Bernstein et al., *The effect of oral leukotriene antagonist, ICI 204,219 on leukotriene D4 and histamine–induced cutaneous vascular reactions in man*, J. Allergy.Clin. Immunol., vol. 87, No. 1, Part 1, 93–98 (Jan. 1991).

Malcolm et al., *Uniparental paternal disomy in Angelman's syndrome*, The Lancet, vol. 337, 694–697 (Mar. 23, 1991).

Hui et al., *Lung function improvement in asthma with a cysteinyl–leukotriene receptor antagonist*, The Lancet, vol. 337, 1062–1063 (May 4, 1991).

Taylor et al.,*Effect of cysteinyl–leukotriene receptor antagonist ICI 204.219 on allergen–induced bronchoconstriction and airway hyperreactivity in atopic subjects*, The Lancet, vol. 337, No. 8743, 690–694 (Mar. 23, 1991).

Mitchell Glass, *Initial Results with Oral Administration of ICI 204,219*, Annals of the New York Academy of Sciences, vol. 629, 143–147 (1991).

A. Bondi, *Van der Walls Volumes and Rad*ii, J. Phys. Chem., vol. 68, No. 3, 441–451 (Mar. 16, 1964).

Boot et al., *The pharmacological evaluation of LY170680, a novel leukotriene D4 and E4 antagonist in the guinea–pig*, Br. J. Pharmacol., vol. 98(1), 259–267 (Sep. 1989).

Hock et al., *Protective Effects of a New LTD4 Antagonist (LY–171883)in Traumatic Shock*, Circulatory Shock, vol. 17, No. 4, 263–272 (1985).

Keppler et al., *Endogenous leukotriene D4 formation during anaphylactic shock in the guinea pig*, Proc. Natl. Acad. Sci. USA, vol. 84, No. 16, 5903–5907 (Aug. 1987).

*LY171883,1–(2–Hydroxy–3–Propyl–4–(4–(1H–Tetrazol–5–yl)Butoxy)phenyl))Ethanone, an Orally Active Leukotriene D4 Antagonist*, The Journal of Pharmacology and Experimental Therapeutics, vol. 233, No. 1, 148–157 (Jun. 1985).

Phillips et al., *Dose–Related Antagonism of Leukotriene D4–Induced Bronchoconstriction by p.o. Administration of LY–171883 in Nonasthmatic Subjects*, The Journal of Pharmacology and Experimental Therapeutics, vol. 246, No. 2, 732–738 (Aug. 1988).

Krausz et al., *Effect of the Leukotriene Receptor antagonist LY–171883 on Endotoxemia in Awake Sheep*, Circulatory Shock, vol. 26, No. 4, 431–441 (1988).

Cloud et al., *A Specific LTD4/LTE4–receptor antagonist Improves Pulmonary Function in Patients with Mild, Chronic Asthma*, American Review of Respiratory Disease, vol. 140, No. 5, 1336–1339 (Nov. 1989).

Diaz et al., *Leucocytes and Mediators in Bronchoalveolar Lavage During Allergen–Induced late–Phase Asthmatic Reactions*, American Review of Respiratory Disease, vol. 139, No. 6, 1383–1390 (Jun. 1989).

Skoner et al., *Plasma Elevations of a Histamine and a Prostaglandin Metabolite in Acute Asthma*, American Review of Respiratory Disease, vol. 137, No. 5, 1009–1014 (May 1988).

Cloud et al., *Efficacy and Safety of LY171883 in Patients with Mild Chronic Asthma*, The Journal of Allergy and Clinical Immunology, vol. 79 No. 1, 256 (Jan. 1987).

O'Hickey et al.,*Leukotrienes C4, D4, and E4 Enhance Histamine Responsiveness in Asthmatic Airways*, Am. Review of Respiratory Disease, vol. 144, No. 5, 1053–1057 (Nov. 1991).

Cannon et al., *Interaction of LY171883 and other peroxisome proliferators with fatty–acid–binding protein isolated from rat liver*, Biochem. J., vol. 280, Part 2, 387–391 (Dec. 1, 1991).

Fleisch et al., *A Brief Review of Preclinical and Clinical Studies with LY171883 and Some Comments on Newer Cysteinyl Leukotriene Receptor Antagonists*, Annals New York Academy of Sciences, vol. 524, 356–368 (1988).

Obata et al., *New Antagonists of Leukotrienes: ONO–RS–411 and ONO–RS–347*, Advances in Prostaglandin, Thromboxane, and Leukotriene Research, vol. 15, 229–231 (1985).

Adaikan et al., *Effects of Two New Leukotriene Antagonists ONO–RS–347 and ONO–RS–411 (ONO–1078)on the Guinea Pig and Human Respiratory and Other Systems*, Advances in Prostaglandin, Thromboxane, and Leukotriene Research, vol. 17A, 549–553 (1987).

Nishiye et al., *Some effects of leukotriene D4 on the mechanical properties of the guinea–pig basilar artery*, Br. J. Pharmacol., vol. 93(3), 591–600 (Mar. 1988).

Wasserman et al., *Pharmacologic Profile of SK&F 104353, A Novel, Highly Potent and Selective Peptidoleukotriene Antagonist*, Advances in Prostaglandin, Thromboxane, and Leukotriene Research, vol. 17A, 532–535 (1987).

Sarau et al.,*Identification and Characterization of Leukotriene D4 Receptors and Signal Transduction Processes in Rat Basophilic Leukemia Cells*, The Journal of Biological Chemistry, vol. 262, No. 9, 4034–4041 (Mar. 25, 1987).

Mong et al., *SKF 104353, a High Affinity Antagonist for Human and Guinea Pig Lung Leukotriene D4 Receptor, Blocked Phosphatidylinositol Metabolism and Thromboxane synthesis Induced by Leukotriene D4*, Molecular Pharmacology, vol. 32, No. 2, 223–229 (Aug. 1987).

Hay et al., *Pharmacologic Profile of SK&F 104353: A Novel, Potent and Selective Peptidoleukotriene Receptor Antagonist in Guinea Pig and Human Airways*, The Journal of Pharmacology and Experimental Therapeutics, vol. 243, No. 2, 474–481 (Nov. 1987).

Xuan et al., *Effects of SK&F 104353, a leukotriene receptor antagonist, on the bronchial responses to histamine in subjects with asthma: A comparative study with terfenadine*, J. Allergy Clin. Immunol., vol. 85, No. 5, 865–871 (May 1990).

Mattern et al., *Transient activation of topoisomerase I in leukotriene D4 signal transduction in human cells*, Biochem. J., vol. 265, No. 1, 101–107 (Jan. 1990).

Christie et al., *The effect of inhalation of the leukotriene receptor antagonist, SK&F 104353, on leukotriene C4– and leukotriene E4–induced bronchoconstriction in subjects with asthma*, J. Allergy Clin. Immunol., vol. 88, No. 2, 193–198 (Aug. 1991).

Joos et al., *The Effect of Aerosolized SK&F 104353–Z2 on the Bronchoconstrictor Effect of Leukotriene D4 in Asthmatics*, Pulmonary Pharmacology, vol. 4, No. 1, 37–42 (1991).

Terao, S., *Quinone Derivatives: Synthesis and Structure–Activity Relations of a Novel Class of Eicosanoid Antagonists, AA–2414 and its Analogs*, Advances in Prostaglandin, Thromboxane, and Leukotriene Research, vol. 19, 651–654 (1989).

Ashida et al., *A Novel Anti–Asthmatic Quinone Derivative, AA–2414 with a Potent Antagonistic Activity Against a Variety of Spasmogenic Prostanoids*, Prostaglandins, vol. 38, No. 1, 91–112 (Jul. 1989).

Shiraishi et al., *Quinones. 4. Novel Eicosanoid Antagonists: Synthesis and Pharmacological Evaluation*, J. Med. Chem., vol. 32, No. 9, 2214–2221 (Sep. 1989).

Akira Ishii et al., *AntiIgE–Induced Asthma in Guinea Pigs; A New Model for Asthma*, Japanese Journal of Allergology, vol. 39, No. 6, 502–508 (Jun. 1990).

Imura et al., *The Role of Thromboxane(TX) A2 in Rabbit Arterial Thrombosis Induced by Endothelial Damage*, Thrombosis Research, vol. 59, No. 1, 195–205 (Jul. 1990).

Imura et al., *Antagonistic Action of AA–2414 on Thromboxane A2/Prostaglandin Endoperoxide Receptor in Platelets and Blood Vessels*, Japan. J. Pharmacol., vol. 52, No. 1, 35–43 (Jan. 1990).

Fujimura et al., *Effect of a thromboxane A2 receptor antagonist (AA–2414) on bronchial hyperresponsiveness to methacholine in subjects with asthma*, J. Allergy Clin. Immunol., vol. 87, No. 1, Part 1, 23–27 (Jan. 1991).

Von Sprecher et al., *Novel Leukotriene Antagonists: Structure Activity of Analogs of LTD4 Replacement of the 1–Carboxylic Group by a Methyl Group("Methyl Principle") Results in Leukotriene Antagonists and Phospholipase Inhibitors*, Advances in Prostaglandin, Thromboxane, and Leukotriene Research, vol. 17A, 519–525 (1987).

Von Sprecher et al., *Leukotriene D4 (LTD4) Antagonists: Structure Activity Relationships of Stable Phenylsubstituted Leukotriene Analogs*, Advances in prostaglandin, Thromboxane, and Leukotriene Research, vol. 19, 647–650 (1989).

Piper et al., *Leukotrienes and Inflammatory Lung Disease*, Annals New York Academy of Sciences, vol. 629, 112–119 (1991).

Barnes et al., *Studies of Leukotriene Antagonists and Synthesis Inhibitors in Man*, Mechanisms in Asthma: Pharmacology, Physiology, and Management, 393–403 (1988).

Jones et al., *Antigen–induced contraction of guinea–pig isolated trachea: studies with novel inhibitors and antagonists of arachidonic acid metabolites*, Br. J. Pharmacol., vol. 95(1), 309–321 (Sep. 1988).

Yee et al., *A Novel Series of Selective Leukotriene Antagonist: Exploration and Optimization of the Acidic Region in 1,6–Disubstituted Indoles and Indazoles*, J. Med. Chem., vol. 33, No. 9, 2437–2451 (Sep. 1990).

R.A. Lewis, et al., *Slow reacting substances of anaphylaxis: Identification of leukotrienes C–1 and D from human and rat sources*, Proc. Natl. Acad. Sci., USA, vol. 77, No. 6, 3710–3714 (Jun. 1980).

*Merck Sharp & Dohme Pharmaceuticals, SRL v. Teva Pharmaceuticals USA, Inc. et al.,* Teva's Proposed Statement of Fact, Filed Mar. 18, 2009.

*Merck Sharp & Dohme Pharmaceuticals, SRL v. Teva Pharmaceuticals USA, Inc. et al.,* Joint Statement of Law Regarding Inequitable Conduct, Filed Mar. 18, 2009.

*Merck Sharp & Dohme Pharmaceuticals, SRL v. Teva Pharmaceuticals USA, Inc. et al.,* Merck Sharp & Dohme Pharmaceuticals, SRL's Proposed Findings of Facts, filed Mar. 18, 2009.

*Merck Sharp & Dohme Pharmaceuticals, SRL v. Teva Pharmaceuticals USA, Inc. et al.,* Teva's Notice of Disclosure of Prior Art Pursuant to 35 U.S.C. §0 282, Filed Jan. 22, 2009.

Certified translation of file history of Japanese Patent Application No.1 H03–331110, *Unsaturated Hydroxyalkylquinolinic Acid as Leukotriene Antagonistic Agent*, application date Oct. 14, 1991.

File History for EP91309306.8–2101 0480717.

File History for Canadian Patent No. 2,053,209.

File History for Australian Patent No. 639610.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 7 and 18-22 is confirmed.

Claims 2–6, 8–17 and 23 were not reexamined.

\* \* \* \* \*